US007582304B2

(12) United States Patent
Dattwyler et al.

(10) Patent No.: US 7,582,304 B2
(45) Date of Patent: *Sep. 1, 2009

(54) **GROUPS OF *BORRELIA BURGDORFERI* AND *BORRELIA AFZELII* THAT CAUSE LYME DISEASE IN HUMANS**

(75) Inventors: Raymond J. Dattwyler, Setauket, NY (US); Gerald Seinost, Graz (AU); Daniel Dykhuizen, St. James, NY (US); Benjamin J. Luft, Setauket, NY (US); Maria J. C. Gomes-Solecki, New York, NY (US)

(73) Assignees: Research Foundation of the State University of New York, Stony Brook, NY (US); Brook Biotechnologies, Inc., Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/371,564

(22) Filed: Mar. 9, 2006

(65) Prior Publication Data
US 2006/0182756 A1 Aug. 17, 2006
US 2009/0060932 A2 Mar. 5, 2009

Related U.S. Application Data

(62) Division of application No. 09/596,746, filed on Jun. 19, 2000, now Pat. No. 7,060,281.

(60) Provisional application No. 60/140,042, filed on Jun. 18, 1999.

(51) Int. Cl.
*A61K 39/02* (2006.01)
*A61K 39/00* (2006.01)
*C12N 15/00* (2006.01)
*C07K 17/00* (2006.01)
*C07K 1/00* (2006.01)

(52) U.S. Cl. .............. 424/234.1; 424/184.1; 424/185.1; 424/190.1; 424/192.1; 424/200.1; 424/203.1; 435/320.1; 530/300; 530/350; 536/23.1; 536/23.7

(58) Field of Classification Search .............. 424/184.1, 424/185.1, 190.1, 192.1, 200.1, 203.1, 234.1; 435/320.1; 530/300, 350; 536/23.1, 23.7
See application file for complete search history.

(56) References Cited

U.S. PATENT DOCUMENTS 6,221,363 B1 4/2001 Livey et al.
7,060,281 B1 6/2006 Dattwyler et al.

FOREIGN PATENT DOCUMENTS

| WO | WO 94/19697 | 9/1994 |
| WO | WO 94/25596 | 11/1994 |
| WO | WO 95/12676 | 5/1995 |
| WO | WO 96/40290 | 12/1996 |
| WO | WO 97/42221 | 11/1997 |
| WO | WO 99/14345 | 3/1999 |
| WO | WO 00/06745 | 2/2000 |
| WO | WO 00/78966 AL | 12/2000 |

OTHER PUBLICATIONS

Wang, Ing-Nang et al., "Genetic Diversity of *ospC* in a Local Population of *Borrelia burgdorferi sensu stricto*," *Genetics*, 151:15-30 (1999).
de Silva, Aravinda M. et al., "Perspectives Series: Host/Pathogen Interactions, Arthropod- and Host-specific Gene Expression by *Borrelia burgdorferi*," *J. Clin. Invest.*, 99(3):377-379 (1997).
Fingerle, Volker et al., "Expression of outer surface proteins A and C of *Borrelia burgdorferi* in *Ixodes ricinus* ticks removed from humans," *Med. Microbiol. Immunol.*, 187:121-126 (1998).
Gilmore, Robert D. et al., "Outer Surface Protein C (OspC), but Not P39, Is a Protective Immunogen against a Tick-Transmitted *Borrelia burgdorferi* Challenge: Evidence for a Conformational Protective Epitope in OspC," *Infection and Immunity*, 64(6):2234-2239 (1996).
Montgomery, Ruth R. et al., "Direct Demonstration of Antigenic Substitution of *Borrelia burgdorferi* Ex Vivo: Exploration of the Paradox of the Early Immune Response to Outer Surface Proteins A and C in Lyme Disease," *J. Exp. Med.*, 183:261-269 (1996).
Probert, William Scott et al., "Immunization with Outer Surface Protein (Osp) A, but Not OspC, Provides Cross-Protection of Mice Challenged with North American Isolates of *Borrelia burgdorferi*," *The J. of Infectious Disease*, 175:400-405 (1997).
Probert, William Scott et al., "Protection of C3H/HeN Mice from Challenge with *Borrelia burgdorferi* through Active Immunization with OspA, OspB, or OspC, but Not with OspD or the 83-Kilodalton Antigen," *Infection and Immunity*, 62(5):1920-1926 (1994).
Schwan, Tom G. et al., "Induction of an outer surface protein on *Borrelia burgdorferi* during tick feeding," *Proc. Natl. Acad. Sci., USA*, 92:2909-2913 (1995).
Simon, Markus M. et al., "Lyme Disease: Pathogenesis and Vaccine Development," *Zent.bl. Bakteriol*, 289:690-695 (1999).
Steigbigel, Roy T. et al., "Immunization against Lyme Disease—An Important First Step," *NEJM*, 339(4):263-264 (1998).

(Continued)

*Primary Examiner*—Rodney P. Swartz
(74) *Attorney, Agent, or Firm*—Hamilton, Brook, Smith & Reynolds, P.C.

(57) ABSTRACT

The present invention is drawn to an immunogenic composition comprising OspC polypeptides from Lyme Disease causing *Borrelia*. In one embodiment, the immunogenic composition of the present invention comprises at least one OspC polypeptide or immunogenic fragment thereof from each of *Borrelia burgdorferi* OspC families A, B, I and K. In another embodiment, the immunogenic composition of the present invention comprises at least one OspC polypeptide or immunogenic fragment thereof from each of *Borrelia afzelii* OspC families A and B.

21 Claims, 8 Drawing Sheets

OTHER PUBLICATIONS

Stover, C. K. et al., "Protective Immunity Elicited by rBCG Vaccines," *Dev. Biol. Stand. Basel, Karger,* 82:163-170 (1994).

Wahlberg, Peter, "Vaccination against Lyme borreliosis," *Ann. Med.,* 31:233-235 (1999).

Wilske, Bettina et al., "Immunological and Molecular Polymorphisms of OspC, and Immunodominant Major Outer Surface Protein of *Borrelia burgdorferi*," *Infection and Immunity,* 61(5):2182-2191 (1993).

Wilske, B. et al., "Immunological and Molecular Variability of OspA and OspC. Implications for *Borrelia* Vaccine Development," *Infection,* 24(2):208-212 (1996).

Wilske, Bettina et al., "Diversity of OspA and OspC among cerebrospinal fluid isolates of *Borrelia burgdorferi* sensu lato from patients with neuroborreliosis in Germany," *Med. Microbiol. Immunol.,* 184:195-201 (1996).

Zhong, Weimin et al., " Resolution of experimental and tick-borne *Borrelia burgdorferi* infection in mice by passive, but not active immunization using recombinant OspC," *Eur. J. Immunol.,* 29:946-957 (1999).

Zhong, Weimin et al., "Therapeutic passive vaccination against chronic Lyme disease in mice," *Proc. Natl. Acad. Sci.,* USA, 94:12533-12538 (1997).

| | Early Lyme: #P(total) | | | | Sensitivity | | Potential cross-reactivity: #P(Total Tested) | | | | Specificity | |
|---|---|---|---|---|---|---|---|---|---|---|---|---|
| | EMA | EA | Ac. Dissem. | Ac. Conval. | #P(Total) | (%) | Syphilis | SLE &RA | Normals End. | Normals NonEnd. | #P(Total) | (%) |
| C1 (clut1) | 6(10) | ND | 4(10) | 8(8) | 18(28) | 64% | 1(10) | 1(10) | 2(10) | 0(8) | 4(38) | 11% |
| C2 (clut2) | 4(10) | ND | 5(10) | 8(8) | 17(28) | 61% | 0(10) | 2(10) | 2(10) | 0(8) | 4(38) | 11% |
| C1C10 (clut3) | 7(10) | ND | 4(10) | 5(8) | 16(28) | 57% | 4(10) | 1(10) | 2(10) | 0(10) | 7(30) | 18% |
| C1C12 (clut4) | 2(10) | ND | 3(10) | 5(8) | 10(28) | 36% | 2(10) | 0(10) | 0(10) | ND | 2(30) | 7% |
| B31C10 (clut5) | 8(10) | ND | 6(10) | 5(8) | 19(28) | 68% | 2(10) | 2(10) | 4(10) | 0(8) | 8(38) | 21% |
| B31C12 (clut6) | 7(10) | ND | 6(10) | 6(8) | 19(28) | 68% | 1(10) | 1(10) | 1(10) | 0(8) | 3(38) | 8% |
| C2C7 (clut7) | 5(10) | 6(8) | 3(10) | 4(7) | 18(35) | 51% | 1(11) | 0(10) | 1(20) | 0(8) | 2(49) | 4% |
| C2C10 (clut8) | 4(10) | 7(8) | 5(10) | 4(7) | 20(35) | 57% | 0(11) | 0(10) | 1(20) | 0(8) | 1(49) | 2% |
| C2C12 (clut9) | 5(10) | 7(8) | 6(10) | 4(7) | 22(35) | 63% | 0(11) | 1(10) | 3(20) | 0(8) | 4(49) | 8% |
| C5C7 (clut10) | 7(10) | ND | 4(10) | 5(8) | 16(28) | 57% | 2(10) | 2(10) | 0(10) | ND | 4(30) | 13% |
| C5C10 (clut11) | 6(10) | ND | 4(10) | 5(8) | 15(28) | 54% | 0(10) | 0(10) | 0(10) | ND | 0(30) | 0% |
| C5C12 (clut12) | 8(10) | ND | 8(10) | 6(8) | 22(28) | 79% | 5(10) | 3(10) | 3(10) | 0(8) | 11(38) | 29% |

EMA = Erythema Migrans Acute
EA = Acute
Ac. Dissem. = Acute Disseminated
Ac. Conval. = Acute Convalescent
P = Number of positives
SLE = Systemic Lupus Erythematosus
RA = Rheumatoid Arthritis
End. = Endemic Field Workers
NonEnd. = Non Endemic

Fig. 8

SEQUENCE LISTING

<160> NUMBER OF SEQ ID NOS: 86

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
aaagaataca ttaagtgcga tatt                                    24

<210> SEQ ID NO 2
<211> LENGTH: 27
<212> TYPE: DNA
<213> ORGANISM: Artificial Sequence
<220> FEATURE:

```
<223> OTHER INFORMATION: Primer

<400> SEQUENCE: 2
caatccactt aattttgtg ttattag                                      27

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ttgttagcag gagcttatgc aatatc                                      26

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gggcttgtaa gctctttaac tg                                          22

<210> SEQ ID NO 5
<211> LENGTH: 573
<212> TYPE: DNA
<213> ORGANISM: borrelia burgdorferi
<220> FEATURE:
<221> NAME/KEY: CDS
<222> LOCATION: (1)...(573)

<400> SEQUENCE: 5
```

| | | | | | | | | | | | | | | | | |
|---|---|---|---|---|---|---|---|---|---|---|---|---|---|---|---|---|
| atg | gct | tgt | aat | aat | tca | ggg | aaa | gat | ggg | aat | aca | tct | gca | aat | tct | 48 |
| Met | Ala | Cys | Asn | Asn | Ser | Gly | Lys | Asp | Gly | Asn | Thr | Ser | Ala | Asn | Ser | |
| 1 | | | | 5 | | | | | 10 | | | | | 15 | | |
| gct | gat | gag | tct | gtt | aaa | ggg | cct | aat | ctt | aca | gaa | ata | agt | aaa | aaa | 96 |
| Ala | Asp | Glu | Ser | Val | Lys | Gly | Pro | Asn | Leu | Thr | Glu | Ile | Ser | Lys | Lys | |
| | | | 20 | | | | | 25 | | | | | 30 | | | |
| att | acg | gat | tct | aat | gcg | gtt | tta | ctt | gct | gtg | aaa | gag | gtt | gaa | gcg | 144 |
| Ile | Thr | Asp | Ser | Asn | Ala | Val | Leu | Leu | Ala | Val | Lys | Glu | Val | Glu | Ala | |
| | 35 | | | | | 40 | | | | | 45 | | | | | |
| ttg | ctg | tca | tct | ata | gat | gag | ctt | gct | aaa | gct | att | ggt | aaa | aaa | ata | 192 |
| Leu | Leu | Ser | Ser | Ile | Asp | Glu | Leu | Ala | Lys | Ala | Ile | Gly | Lys | Lys | Ile | |
| 50 | | | | | 55 | | | | | 60 | | | | | | |
| aaa | aac | gat | ggt | agt | tta | gat | aat | gaa | gca | aat | cgc | aac | gag | tca | ttg | 240 |
| Lys | Asn | Asp | Gly | Ser | Leu | Asp | Asn | Glu | Ala | Asn | Arg | Asn | Glu | Ser | Leu | |
| 65 | | | | 70 | | | | | 75 | | | | | 80 | | |
| tta | gca | gga | gct | tat | aca | ata | tca | acc | tta | ata | aca | caa | aaa | tta | agt | 288 |
| Leu | Ala | Gly | Ala | Tyr | Thr | Ile | Ser | Thr | Leu | Ile | Thr | Gln | Lys | Leu | Ser | |
| | | | | 85 | | | | | 90 | | | | | 95 | | |
| aaa | tta | aac | gga | tca | gaa | ggt | tta | aag | gaa | aag | att | gcc | gca | gct | aag | 336 |
| Lys | Leu | Asn | Gly | Ser | Glu | Gly | Leu | Lys | Glu | Lys | Ile | Ala | Ala | Ala | Lys | |
| | | | 100 | | | | | 105 | | | | | 110 | | | |
| aaa | tgc | tct | gaa | gag | ttt | agt | act | aaa | cta | aaa | gat | aat | cat | gca | cag | 384 |
| Lys | Cys | Ser | Glu | Glu | Phe | Ser | Thr | Lys | Leu | Lys | Asp | Asn | His | Ala | Gln | |
| | 115 | | | | | 120 | | | | | 125 | | | | | |
| ctt | ggt | ata | cag | ggc | gtt | act | gat | gaa | aat | gca | aaa | gct | att | tta | | 432 |
| Leu | Gly | Ile | Gln | Gly | Val | Thr | Asp | Glu | Asn | Ala | Lys | Ala | Ile | Leu | | |
| 130 | | | | | 135 | | | | | 140 | | | | | | |
| aaa | gca | aat | gca | gcg | ggt | aaa | gat | aag | ggc | gtt | gaa | gaa | ctt | gaa | aag | 480 |
| Lys | Ala | Asn | Ala | Ala | Gly | Lys | Asp | Lys | Gly | Val | Glu | Glu | Leu | Glu | Lys | |

```
                                                    -continued 145                 150                 155                 160
ttg tcc gga tca tta gaa agc tta tca aaa gca gct aaa gag atg ctt         528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat gga tcc             573
Ala Asn Ser Val Lys Glu Leu Thr Ser Pro Val Val His Gly Ser
            180                 185                 190

<210> SEQ ID NO 6
<211> LENGTH: 191
<212> TYPE: PRT
<213> ORGANISM: borrelia burgdorferi

<400> SEQUENCE: 6

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Ser
            180                 185                 190

<210> SEQ ID NO 7
<211> LENGTH: 557
<212> TYPE: DNA
<213> ORGANISM: Borrelia burgdorferi
<220> FEATURE:
<221> NAME/KEY: CDS
<222> LOCATION: (3)...(557)

<400> SEQUENCE: 7 atg gct t

```
       50                  55                  60
ata ggc aat aat ggt tta gag gcc aat cag agt aaa aac aca tca ttg      240
Ile Gly Asn Asn Gly Leu Glu Ala Asn Gln Ser Lys Asn Thr Ser Leu
 65                  70                  75                  80 tta tca gga gct tat gca ata tct gac cta ata gca gaa aaa tta aat      288
Leu Ser Gly Ala Tyr Ala Ile Ser Asp Leu Ile Ala Glu Lys Leu Asn
                 85                  90                  95 gta ttg aaa aat gaa gaa tta aag gaa aag att gat aca gct aag caa      336
Val Leu Lys Asn Glu Glu Leu Lys Glu Lys Ile Asp Thr Ala Lys Gln
            100                 105                 110 tgt tct aca gaa ttt act aat aaa cta aaa agt gaa cat gca gtg ctt      384
Cys Ser Thr Glu Phe Thr Asn Lys Leu Lys Ser Glu His Ala Val Leu
            115                 120                 125 ggt ctg gac aat ctt act gat gat aat gca caa aga gct att tta aaa      432
Gly Leu Asp Asn Leu Thr Asp Asp Asn Ala Gln Arg Ala Ile Leu Lys
        130                 135                 140 aaa cat gca aat aaa gat aag ggt gct gca gaa ctt gaa aag tta ttt      480
Lys His Ala Asn Lys Asp Lys Gly Ala Ala Glu Leu Glu Lys Leu Phe
145                 150                 155                 160 aaa gcg gta gaa aac tta tca aaa gca gct caa gac aca tta aaa aat      528
Lys Ala Val Glu Asn Leu Ser Lys Ala Ala Gln Asp Thr Leu Lys Asn
                165                 170                 175 gct gtt aaa gag ctt aca agt cct att gt                               557
Ala Val Lys Glu Leu Thr Ser Pro Ile
            180                 185

<210> SEQ ID NO 8
<211> LENGTH: 185
<212> TYPE: PRT
<213> ORGANISM: Borrelia burgdorferi

<400> SEQUENCE: 8

Met Ala Cys Asn Asn Ser Gly Lys Asp Gly Asn Ala Ser Ala Asn Ser
 1               5                  10                  15

Ala Asp Glu Ser Val Lys Gly Pro Asn Leu Thr Glu Ile Ser Lys Lys
             20                  25                  30

Ile Thr Glu Ser Asn Ala Val Val Leu Ala Val Lys Glu Val Glu Thr
         35                  40                  45

Leu Leu Ala Ser Ile Asp Glu Leu Ala Thr Lys Ala Ile Gly Lys Lys
     50                  55                  60

Ile Gly Asn Asn Gly Leu Glu Ala Asn Gln Ser Lys Asn Thr Ser Leu
 65                  70                  75                  80

Leu Ser Gly Ala Tyr Ala Ile Ser Asp Leu Ile Ala Glu Lys Leu Asn
                 85                  90                  95

Val Leu Lys Asn Glu Glu Leu Lys Glu Lys Ile Asp Thr Ala Lys Gln
            100                 105                 110

Cys Ser Thr Glu Phe Thr Asn Lys Leu Lys Ser Glu His Ala Val Leu
            115                 120                 125

Gly Leu Asp Asn Leu Thr Asp Asp Asn Ala Gln Arg Ala Ile Leu Lys
        130                 135                 140

Lys His Ala Asn Lys Asp Lys Gly Ala Ala Glu Leu Glu Lys Leu Phe
145                 150                 155                 160

Lys Ala Val Glu Asn Leu Ser Lys Ala Ala Gln Asp Thr Leu Lys Asn
                165                 170                 175

Ala Val Lys Glu Leu Thr Ser Pro Ile
            180                 185
```

```
<210> SEQ ID NO 9
<211> LENGTH: 579
<212> TYPE: DNA
<213> ORGANISM: Borrelia burgdorferi
<220> FEATURE:
<221> NAME/KEY: CDS
<222> LOCATION: (1)...(579)

<400> SEQUENCE: 9 atg act tta ttt tta ttt ata tct tgt aat aat tca ggg aaa gat ggg      48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt      96
Asn Thr Ser Ala Asn Ser Ala Asp Glu Ser Val Lys Gly Pro Asn Leu
             20                  25                  30 aca gaa ata agt aaa aaa att acg gat tct aat gcg gtt tta ctt gct     144
Thr Glu Ile Ser Lys Lys Ile Thr Asp Ser Asn Ala Val Leu Leu Ala
         35                  40                  45 gtg aaa gag gtt gaa gcg ttg ctg tca tct ata gat gaa att gct gct     192
Val Lys Glu Val Glu Ala Leu Leu Ser Ser Ile Asp Glu Ile Ala Ala
 50                  55                  60 aaa gct att ggt aaa aaa ata cac caa aat aat ggt ttg gat acc gaa     240
Lys Ala Ile Gly Lys Lys Ile His Gln Asn Asn Gly Leu Asp Thr Glu
 65                  70                  75                  80 aat aat cac aat gga tca ttg tta gcg gga gct tat gca ata tca acc     288
Asn Asn His Asn Gly Ser Leu Leu Ala Gly Ala Tyr Ala Ile Ser Thr
                 85                  90                  95 cta ata aaa caa aaa tta gat gga ttg aaa aat gaa gga tta aag gaa     336
Leu Ile Lys Gln Lys Leu Asp Gly Leu Lys Asn Glu Gly Leu Lys Glu
            100                 105                 110 aaa att gat gcg gct aag aaa tgt tct gaa aca ttt act aat aaa tta     384
Lys Ile Asp Ala Ala Lys Lys Cys Ser Glu Thr Phe Thr Asn Lys Leu
        115                 120                 125 aaa gaa aaa cac aca gat ctt ggt aaa gaa ggt gtt act gat gct gat     432
Lys Glu Lys His Thr Asp Leu Gly Lys Glu Gly Val Thr Asp Ala Asp
    130                 135                 140 gca aaa gaa gcc att tta aaa aca aat ggt act aaa act aaa ggt gct     480
Ala Lys Glu Ala Ile Leu Lys Thr Asn Gly Thr Lys Thr Lys Gly Ala
145                 150                 155                 160 gaa gaa ctt gga aaa tta ttt gaa tca gta gag gtc ttg tca aaa gca     528
Glu Glu Leu Gly Lys Leu Phe Glu Ser Val Glu Val Leu Ser Lys Ala
                165                 170                 175 gct aaa gag atg ctt gct aat tca gtt aaa gag ctt aca agc cct gtt     576
Ala Lys Glu Met Leu Ala Asn Ser Val Lys Glu Leu Thr Ser Pro Val
            180                 185                 190 gtg                                                                  579
Val

<210> SEQ ID NO 10
<211> LENGTH: 193
<212> TYPE: PRT
<213> ORGANISM: Borrelia burgdorferi

<400> SEQUENCE: 10

Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
             20                  25                  30

Thr Glu Ile Ser Lys Lys Ile Thr Asp Ser Asn Ala Val Leu Leu Ala
         35                  40                  45

Val Lys Glu Val Glu Ala Leu Leu Ser Ser Ile Asp Glu Ile Ala Ala
```

```
                 50                  55                  60
Lys Ala Ile Gly Lys Lys Ile His Gln Asn Asn Gly Leu Asp Thr Glu
 65                  70                  75                  80

Asn Asn His Asn Gly Ser Leu Leu Ala Gly Ala Tyr Ala Ile Ser Thr
                 85                  90                  95

Leu Ile Lys Gln Lys Leu Asp Gly Leu Lys Asn Glu Gly Leu Lys Glu
            100                 105                 110

Lys Ile Asp Ala Ala Lys Lys Cys Ser Glu Thr Phe Thr Asn Lys Leu
        115                 120                 125

Lys Glu Lys His Thr Asp Leu Gly Lys Glu Gly Val Thr Asp Ala Asp
    130                 135                 140

Ala Lys Glu Ala Ile Leu Lys Thr Asn Gly Thr Lys Thr Lys Gly Ala
145                 150                 155                 160

Glu Glu Leu Gly Lys Leu Phe Glu Ser Val Glu Val Leu Ser Lys Ala
                165                 170                 175

Ala Lys Glu Met Leu Ala Asn Ser Val Lys Glu Leu Thr Ser Pro Val
            180                 185                 190

Val

<210> SEQ ID NO 11
<211> LENGTH: 582
<212> TYPE: DNA
<213> ORGANISM: Borrelia brgdorferi
<220> FEATURE:
<221> NAME/KEY: CDS
<222> LOCATION: (1)...(582)

<400> SEQUENCE: 11 atg act tta ttt tta ttt ata tct tgt aat aat tca ggg aaa gat ggg      48
Met Thr Leu Phe Leu Phe Ile Ser Cys Asn Asn Ser Gly Lys Asp Gly
  1               5                  10                  15 aat aca tct gca aat tct gct gat gag tct gtt aaa ggg cct aat ctt     96
Asn Thr Ser Ala Asn Ser Ala Asp Glu Ser Val Lys Gly Pro Asn Leu
             20                  25                  30 aca gaa ata agt aaa aaa att acg gat tct aat gcg gtt tta ctt gct    144
Thr Glu Ile Ser Lys Lys Ile Thr Asp Ser Asn Ala Val Leu Leu Ala
         35                  40                  45 gtg aaa gag gtt gaa gcg ttg ctg tca tct ata gat gag ctt gct aaa    192
Val Lys Glu Val Glu Ala Leu Leu Ser Ser Ile Asp Glu Leu Ala Lys
     50                  55                  60 gct att ggt aaa aaa ata aaa aac gat ggt agt tta gat aat gaa gca    240
Ala Ile Gly Lys Lys Ile Lys Asn Asp Gly Ser Leu Asp Asn Glu Ala
 65                  70                  75                  80 aat cgc aac gag tca ttg tta gca gga gct tat aca ata tca acc tta    288
Asn Arg Asn Glu Ser Leu Leu Ala Gly Ala Tyr Thr Ile Ser Thr Leu
                 85                  90                  95 ata aca caa aaa tta agt aaa tta aac gga tca gaa ggt tta aag gaa    336
Ile Thr Gln Lys Leu Ser Lys Leu Asn Gly Ser Glu Gly Leu Lys Glu
            100                 105                 110 aag att gcc gca gct aag aaa tgc tct gaa gag ttt agt act aaa cta    384
Lys Ile Ala Ala Ala Lys Lys Cys Ser Glu Glu Phe Ser Thr Lys Leu
        115                 120                 125 aaa gat aat cat gca cag ctt ggt ata cag ggc gtt act gat gaa aat    432
Lys Asp Asn His Ala Gln Leu Gly Ile Gln Gly Val Thr Asp Glu Asn
    130                 135                 140 gca aaa aaa gct att tta aaa gca aat gca gcg ggt aaa gat aag ggc    480
Ala Lys Lys Ala Ile Leu Lys Ala Asn Ala Ala Gly Lys Asp Lys Gly
145                 150                 155                 160
```

```
gtt gaa gaa ctt gaa aag ttg tcc gga tca tta gaa agc tta tca aaa    528
Val Glu Glu Leu Glu Lys Leu Ser Gly Ser Leu Glu Ser Leu Ser Lys
            165                 170                 175 gca gct aaa gag atg ctt gct aat tca gtt aaa gag ctt aca agc cct    576
Ala Ala Lys Glu Met Leu Ala Asn Ser Val Lys Glu Leu Thr Ser Pro
        180                 185                 190 gtt gtg                                                            582
Val Val
```

<210> SEQ ID NO 12
<211> LENGTH: 194
<212> TYPE: PRT
<213> ORGANISM: Borrelia brgdorferi

<400> SEQUENCE: 12

```
Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
            20                  25                  30

Thr Glu Ile Ser Lys Lys Ile Thr Asp Ser Asn Ala Val Leu Leu Ala
        35                  40                  45

Val Lys Glu Val Glu Ala Leu Leu Ser Ser Ile Asp Glu Leu Ala Lys
    50                  55                  60

Ala Ile Gly Lys Lys Ile Lys Asn Asp Gly Ser Leu Asp Asn Glu Ala
65                  70                  75                  80

Asn Arg Asn Glu Ser Leu Leu Ala Gly Ala Tyr Thr Ile Ser Thr Leu
                85                  90                  95

Ile Thr Gln Lys Leu Ser Lys Leu Asn Gly Ser Glu Gly Leu Lys Glu
            100                 105                 110

Lys Ile Ala Ala Ala Lys Lys Cys Ser Glu Glu Phe Ser Thr Lys Leu
        115                 120                 125

Lys Asp Asn His Ala Gln Leu Gly Ile Gln Gly Val Thr Asp Glu Asn
    130                 135                 140

Ala Lys Lys Ala Ile Leu Lys Ala Asn Ala Ala Gly Lys Asp Lys Gly
145                 150                 155                 160

Val Glu Glu Leu Glu Lys Leu Ser Gly Ser Leu Glu Ser Leu Ser Lys
                165                 170                 175

Ala Ala Lys Glu Met Leu Ala Asn Ser Val Lys Glu Leu Thr Ser Pro
            180                 185                 190

Val Val
```

<210> SEQ ID NO 13
<211> LENGTH: 576
<212> TYPE: DNA
<213> ORGANISM: Borrelia burgdorferi
<220> FEATURE:
<221> NAME/KEY: CDS
<222> LOCATION: (1)...(576)

<400> SEQUENCE: 13

```
atg act tta ttt tta ttt ata tct tgt aat aat tca gga aaa gat ggg     48
Met Thr Leu Phe Leu Phe Ile Ser Cys Asn Asn Ser Gly Lys Asp Gly
 1               5                  10                  15 aat gca tct gca aat tct gct gat gag tct gtt aaa ggg cct aat ctt     96
Asn Ala Ser Ala Asn Ser Ala Asp Glu Ser Val Lys Gly Pro Asn Leu
            20                  25                  30 aca gaa ata agt aaa aaa att aca gaa tct aac gca gtt gtt ctg gcc    144
Thr Glu Ile Ser Lys Lys Ile Thr Glu Ser Asn Ala Val Val Leu Ala
        35                  40                  45
```

```
gtg aaa gaa gtt gag acc tta ctt gca tct ata gat gaa ctt gct acc        192
Val Lys Glu Val Glu Thr Leu Leu Ala Ser Ile Asp Glu Leu Ala Thr
     50                  55                  60 aaa gct att ggt aaa aaa ata ggc aat aat ggt tta gag gcc aat cag        240
Lys Ala Ile Gly Lys Lys Ile Gly Asn Asn Gly Leu Glu Ala Asn Gln
 65                  70                  75                  80 agt aaa aac aca tca ttg tta tca gga gct tat gca ata tct gac cta        288
Ser Lys Asn Thr Ser Leu Leu Ser Gly Ala Tyr Ala Ile Ser Asp Leu
                 85                  90                  95 ata gca gaa aaa tta aat gta ttg aaa aat gaa gaa tta aag gaa aag        336
Ile Ala Glu Lys Leu Asn Val Leu Lys Asn Glu Glu Leu Lys Glu Lys
            100                 105                 110 att gat aca gct aag caa tgt tct aca gaa ttt act aat aaa cta aaa        384
Ile Asp Thr Ala Lys Gln Cys Ser Thr Glu Phe Thr Asn Lys Leu Lys
            115                 120                 125 agt gaa cat gca gtg ctt ggt ctg gac aat ctt act gat gat aat gca        432
Ser Glu His Ala Val Leu Gly Leu Asp Asn Leu Thr Asp Asp Asn Ala
130                 135                 140 caa aga gct att tta aaa aaa cat gca aat aaa gat aag ggt gct gca        480
Gln Arg Ala Ile Leu Lys Lys His Ala Asn Lys Asp Lys Gly Ala Ala
145                 150                 155                 160 gaa ctt gaa aag tta ttt aaa gcg gta gaa aac tta tca aaa gca gct        528
Glu Leu Glu Lys Leu Phe Lys Ala Val Glu Asn Leu Ser Lys Ala Ala
                165                 170                 175 caa gac aca tta aaa aat gct gtt aaa gag ctt aca agt cct att gtg        576
Gln Asp Thr Leu Lys Asn Ala Val Lys Glu Leu Thr Ser Pro Ile Val
            180                 185                 190

<210> SEQ ID NO 14
<211> LENGTH: 192
<212> TYPE: PRT
<213> ORGANISM: Borrelia burgdorferi

<400> SEQUENCE: 14

Met Thr Leu Phe Leu Phe Ile Ser Cys Asn Asn Ser Gly Lys Asp Gly
 1               5                  10                  15

Asn Ala Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
         35                  40                  45

Val Lys Glu Val Glu Thr Leu Leu Ala Ser Ile Asp Glu Leu Ala Thr
     50                  55                  60

Lys Ala Ile Gly Lys Lys Ile Gly Asn Asn Gly Leu Glu Ala Asn Gln
 65                  70                  75                  80

Ser Lys Asn Thr Ser Leu Leu Ser Gly Ala Tyr Ala Ile Ser Asp Leu
                 85                  90                  95

Ile Ala Glu Lys Leu Asn Val Leu Lys Asn Glu Glu Leu Lys Glu Lys
            100                 105                 110

Ile Asp Thr Ala Lys Gln Cys Ser Thr Glu Phe Thr Asn Lys Leu Lys
            115                 120                 125

Ser Glu His Ala Val Leu Gly Leu Asp Asn Leu Thr Asp Asp Asn Ala
130                 135                 140

Gln Arg Ala Ile Leu Lys Lys His Ala Asn Lys Asp Lys Gly Ala Ala
145                 150                 155                 160

Glu Leu Glu Lys Leu Phe Lys Ala Val Glu Asn Leu Ser Lys Ala Ala
                165                 170                 175

Gln Asp Thr Leu Lys Asn Ala Val Lys Glu Leu Thr Ser Pro Ile Val
```

180             185             190

<210> SEQ ID NO 15
<211> LENGTH: 576
<212> TYPE: DNA
<213> ORGANISM: borrelia burgdorferi
<220> FEATURE:
<221> NAME/KEY: CDS
<222> LOCATION: (1)...(576)

<400> SEQUENCE: 15

```
atg act tta ttt tta ttt ata tct tgt aat aat tca aga aaa gat ggg      48
Met Thr Leu Phe Leu Phe Ile Ser Cys Asn Asn Ser Arg Lys Asp Gly
 1               5                  10                  15 aat gca tct aca aat tct gcc gat gag tct gtt aaa ggg cct aat ctt      96
Asn Ala Ser Thr Asn Ser Ala Asp Glu Ser Val Lys Gly Pro Asn Leu
             20                  25                  30 aca gaa ata agt aaa aaa att aca gaa tct aac gca gtt gtt ctg gcc     144
Thr Glu Ile Ser Lys Lys Ile Thr Glu Ser Asn Ala Val Val Leu Ala
         35                  40                  45 gtg aaa gaa gtt gag acc tta ctt gca tct ata gat gaa ctt gct acc     192
Val Lys Glu Val Glu Thr Leu Leu Ala Ser Ile Asp Glu Leu Ala Thr
     50                  55                  60 aaa gct att ggt aag aaa ata ggc aat aat ggt tta gag gcc aat cag     240
Lys Ala Ile Gly Lys Lys Ile Gly Asn Asn Gly Leu Glu Ala Asn Gln
 65                  70                  75                  80 agt aaa aac aca tca ttg tta tca gga gct tat gca ata tct gac cta     288
Ser Lys Asn Thr Ser Leu Leu Ser Gly Ala Tyr Ala Ile Ser Asp Leu
                 85                  90                  95 ata gca gaa aaa tta aat gta ttg aaa aat gaa gaa tta aag gaa aag     336
Ile Ala Glu Lys Leu Asn Val Leu Lys Asn Glu Glu Leu Lys Glu Lys
            100                 105                 110 att gat aca gct aag caa tgt tct aca gaa ttt act aat aaa cta aaa     384
Ile Asp Thr Ala Lys Gln Cys Ser Thr Glu Phe Thr Asn Lys Leu Lys
        115                 120                 125 agt gaa cat gca gtg ctt ggt ctg gac aat ctt act gat gat aat gca     432
Ser Glu His Ala Val Leu Gly Leu Asp Asn Leu Thr Asp Asp Asn Ala
    130                 135                 140 caa aga gct att tta aaa aaa cat gca aat aaa gat aag ggt gct gca     480
Gln Arg Ala Ile Leu Lys Lys His Ala Asn Lys Asp Lys Gly Ala Ala
145                 150                 155                 160 gaa ctt gaa aag tta ttt aaa gcg gta gaa aac tta tca aaa gca gct     528
Glu Leu Glu Lys Leu Phe Lys Ala Val Glu Asn Leu Ser Lys Ala Ala
                165                 170                 175 caa gac aca tta aaa aat gct gtt aaa gag ctt aca agt cct att gtg     576
Gln Asp Thr Leu Lys Asn Ala Val Lys Glu Leu Thr Ser Pro Ile Val
            180                 185                 190
```

<210> SEQ ID NO 16
<211> LENGTH: 192
<212> TYPE: PRT
<213> ORGANISM: borrelia burgdorferi

<400> SEQUENCE: 16

```
Met Thr Leu Phe Leu Phe Ile Ser Cys Asn Asn Ser Arg Lys Asp Gly
 1               5                  10                  15

Asn Ala Ser Thr Asn Ser Ala Asp Glu Ser Val Lys Gly Pro Asn Leu
             20                  25                  30

Thr Glu Ile Ser Lys Lys Ile Thr Glu Ser Asn Ala Val Val Leu Ala
         35                  40                  45

Val Lys Glu Val Glu Thr Leu Leu Ala Ser Ile Asp Glu Leu Ala Thr
```

```
                 50                  55                  60
Lys Ala Ile Gly Lys Lys Ile Gly Asn Asn Gly Leu Glu Ala Asn Gln
 65                  70                  75                  80

Ser Lys Asn Thr Ser Leu Leu Ser Gly Ala Tyr Ala Ile Ser Asp Leu
                 85                  90                  95

Ile Ala Glu Lys Leu Asn Val Leu Lys Asn Glu Glu Leu Lys Glu Lys
                100                 105                 110

Ile Asp Thr Ala Lys Gln Cys Ser Thr Glu Phe Thr Asn Lys Leu Lys
            115                 120                 125

Ser Glu His Ala Val Leu Gly Leu Asp Asn Leu Thr Asp Asp Asn Ala
        130                 135                 140

Gln Arg Ala Ile Leu Lys Lys His Ala Asn Lys Asp Lys Gly Ala Ala
145                 150                 155                 160

Glu Leu Glu Lys Leu Phe Lys Ala Val Glu Asn Leu Ser Lys Ala Ala
                165                 170                 175

Gln Asp Thr Leu Lys Asn Ala Val Lys Glu Leu Thr Ser Pro Ile Val
            180                 185                 190

<210> SEQ ID NO 17
<211> LENGTH: 573
<212> TYPE: DNA
<213> ORGANISM: Borrelia burgdorferi
<220> FEATURE:
<221> NAME/KEY: CDS
<222> LOCATION: (1)...(573)

<400> SEQUENCE: 17 atg act tta ttt tta ttt ata tct tgt aat aat tca ggg aaa gat ggg      48
Met Thr Leu Phe Leu Phe Ile Ser Cys Asn Asn Ser Gly Lys Asp Gly
  1               5                  10                  15 aat aca tct gca aat tct gct gat gag tct gtt aaa ggg cct aat ctt      96
Asn Thr Ser Ala Asn Ser Ala Asp Glu Ser Val Lys Gly Pro Asn Leu
                 20                  25                  30 aca gaa ata agt aaa aaa att aca gaa tct aac gca gtt gtt ctc gcc     144
Thr Glu Ile Ser Lys Lys Ile Thr Glu Ser Asn Ala Val Val Leu Ala
             35                  40                  45 gtg aaa gaa gtt gaa act ttg ctt aca tct ata gat gag ctt gct aaa     192
Val Lys Glu Val Glu Thr Leu Leu Thr Ser Ile Asp Glu Leu Ala Lys
 50                  55                  60 gct att ggt aaa aaa ata aaa aac gat gtt agt tta gat aat gag gca     240
Ala Ile Gly Lys Lys Ile Lys Asn Asp Val Ser Leu Asp Asn Glu Ala
 65                  70                  75                  80 gat cac aac gga tca tta ata tca gga gca tat tta att tca aac tta     288
Asp His Asn Gly Ser Leu Ile Ser Gly Ala Tyr Leu Ile Ser Asn Leu
                 85                  90                  95 ata aca aaa aaa ata agt gca ata aaa gat tca gga gaa ttg aag gca     336
Ile Thr Lys Lys Ile Ser Ala Ile Lys Asp Ser Gly Glu Leu Lys Ala
            100                 105                 110 gaa att gaa aag gct aag aaa tgt tct gaa gaa ttt act gct aaa tta     384
Glu Ile Glu Lys Ala Lys Lys Cys Ser Glu Glu Phe Thr Ala Lys Leu
        115                 120                 125 aaa ggt gaa cac aca gat ctt ggt aaa gaa ggc gtt act gat gat aat     432
Lys Gly Glu His Thr Asp Leu Gly Lys Glu Gly Val Thr Asp Asp Asn
130                 135                 140 gca aaa aaa gcc att tta aaa aca aat aat gat aaa act aag ggc gct     480
Ala Lys Lys Ala Ile Leu Lys Thr Asn Asn Asp Lys Thr Lys Gly Ala
145                 150                 155                 160 gat gaa ctt gaa aag tta ttt gaa tca gta aaa aac ttg tca aaa gca     528
Asp Glu Leu Glu Lys Leu Phe Glu Ser Val Lys Asn Leu Ser Lys Ala
```

```
                                    165                 170                 175
gct aaa gag atg ctt act aat tca gtt aaa gag ctt aca agc cct           573
Ala Lys Glu Met Leu Thr Asn Ser Val Lys Glu Leu Thr Ser Pro
                180                 185                 190
```

<210> SEQ ID NO 18
<211> LENGTH: 191
<212> TYPE: PRT
<213> ORGANISM: Borrelia burgdorferi

<400> SEQUENCE: 18

```
Met Thr Leu Phe Leu Phe Ile Ser Cys Asn Asn Ser Gly Lys Asp Gly
  1               5                  10                  15

Asn Thr Ser Ala Asn Ser Ala Asp Glu Ser Val Lys Gly Pro Asn Leu
             20                  25                  30

Thr Glu Ile Ser Lys Lys Ile Thr Glu Ser Asn Ala Val Val Leu Ala
         35                  40                  45

Val Lys Glu Val Glu Thr Leu Leu Thr Ser Ile Asp Glu Leu Ala Lys
 50                  55                  60

Ala Ile Gly Lys Lys Ile Lys Asn Asp Val Ser Leu Asp Asn Glu Ala
 65                  70                  75                  80

Asp His Asn Gly Ser Leu Ile Ser Gly Ala Tyr Leu Ile Ser Asn Leu
                 85                  90                  95

Ile Thr Lys Lys Ile Ser Ala Ile Lys Asp Ser Gly Glu Leu Lys Ala
                100                 105                 110

Glu Ile Glu Lys Ala Lys Lys Cys Ser Glu Glu Phe Thr Ala Lys Leu
            115                 120                 125

Lys Gly Glu His Thr Asp Leu Gly Lys Glu Gly Val Thr Asp Asp Asn
130                 135                 140

Ala Lys Lys Ala Ile Leu Lys Thr Asn Asn Asp Lys Thr Lys Gly Ala
145                 150                 155                 160

Asp Glu Leu Glu Lys Leu Phe Glu Ser Val Lys Asn Leu Ser Lys Ala
                165                 170                 175

Ala Lys Glu Met Leu Thr Asn Ser Val Lys Glu Leu Thr Ser Pro
                180                 185                 190
```

<210> SEQ ID NO 19
<211> LENGTH: 553
<212> TYPE: DNA
<213> ORGANISM: Borrelia burgdorferi
<220> FEATURE:
<221> NAME/KEY: CDS
<222> LOCATION: (1)...(553)

<400> SEQUENCE: 19

```
atg act tta ttt tta ttt ata tct tgt aat aat tca gga aaa gat ggg            48
Met Thr Leu Phe Leu Phe Ile Ser Cys Asn Asn Ser Gly Lys Asp Gly
  1               5                  10                  15 aat aca tct gca aat tct gct gat gag tct gtt aaa ggg cct aat ctt           96
Asn Thr Ser Ala Asn Ser Ala Asp Glu Ser Val Lys Gly Pro Asn Leu
             20                  25                  30 aca gaa ata agt aaa aaa att aca gaa tct aac gca gtt gtt ctg gct          144
Thr Glu Ile Ser Lys Lys Ile Thr Glu Ser Asn Ala Val Val Leu Ala
         35                  40                  45 gtg aaa gaa att gaa act ttg ctt gca tct ata gat gaa ctt gct act          192
Val Lys Glu Ile Glu Thr Leu Leu Ala Ser Ile Asp Glu Leu Ala Thr
 50                  55                  60 aaa gct att ggt aaa aaa ata gat aac aat gct ggt ttg ggt gct gaa          240
Lys Ala Ile Gly Lys Lys Ile Asp Asn Asn Ala Gly Leu Gly Ala Glu
```

-continued

```
              65                  70                  75                  80
gtg ggt caa aac gga tca ttg cta gca gga gct tat gca atc tca act         288
Val Gly Gln Asn Gly Ser Leu Leu Ala Gly Ala Tyr Ala Ile Ser Thr
                85                  90                  95 gta ata ata gaa aaa ttg agc aca tta aaa aat gta gaa gaa tta aaa         336
Val Ile Ile Glu Lys Leu Ser Thr Leu Lys Asn Val Glu Glu Leu Lys
            100                 105                 110 gaa aaa att aca aag gct aag gat tgt tct gaa aaa ttc act aaa aaa         384
Glu Lys Ile Thr Lys Ala Lys Asp Cys Ser Glu Lys Phe Thr Lys Lys
            115                 120                 125 tta aaa gat agc cgc gca gag ctt ggt aaa aaa gat gcc agt gat gat         432
Leu Lys Asp Ser Arg Ala Glu Leu Gly Lys Lys Asp Ala Ser Asp Asp
        130                 135                 140 gat gca aaa aaa gct att tta aaa aca aat caa gct aac gat aag ggt         480
Asp Ala Lys Lys Ala Ile Leu Lys Thr Asn Gln Ala Asn Asp Lys Gly
145                 150                 155                 160 gct aaa gaa ctt aaa gag tta ttt gaa gca gta gaa agc ttg tca aaa         528
Ala Lys Glu Leu Lys Glu Leu Phe Glu Ala Val Glu Ser Leu Ser Lys
                165                 170                 175 gcg gct aaa gag atg cta aac aag t                                       553
Ala Ala Lys Glu Met Leu Asn Lys
            180

<210> SEQ ID NO 20
<211> LENGTH: 184
<212> TYPE: PRT
<213> ORGANISM: Borrelia burgdorferi

<400> SEQUENCE: 20

Met Thr Leu Phe Leu Phe Ile Ser Cys Asn Asn Ser Gly Lys Asp Gly
1               5                   10                  15

Asn Thr Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
        35                  40                  45

Val Lys Glu Ile Glu Thr Leu Leu Ala Ser Ile Asp Glu Leu Ala Thr
50                  55                  60

Lys Ala Ile Gly Lys Lys Ile Asp Asn Asn Ala Gly Leu Gly Ala Glu
65                  70                  75                  80

Val Gly Gln Asn Gly Ser Leu Leu Ala Gly Ala Tyr Ala Ile Ser Thr
                85                  90                  95

Val Ile Ile Glu Lys Leu Ser Thr Leu Lys Asn Val Glu Glu Leu Lys
            100                 105                 110

Glu Lys Ile Thr Lys Ala Lys Asp Cys Ser Glu Lys Phe Thr Lys Lys
            115                 120                 125

Leu Lys Asp Ser Arg Ala Glu Leu Gly Lys Lys Asp Ala Ser Asp Asp
        130                 135                 140

Asp Ala Lys Lys Ala Ile Leu Lys Thr Asn Gln Ala Asn Asp Lys Gly
145                 150                 155                 160

Ala Lys Glu Leu Lys Glu Leu Phe Glu Ala Val Glu Ser Leu Ser Lys
                165                 170                 175

Ala Ala Lys Glu Met Leu Asn Lys
            180

<210> SEQ ID NO 21
<211> LENGTH: 582
<212> TYPE: DNA
<213> ORGANISM: Borrelia burgdorferi
```

-continued

```
<220> FEATURE:
<221> NAME/KEY: CDS
<222> LOCATION: (1)...(582)

<400> SEQUENCE: 21 atg act tta ttt tta ttt ata tct tgt aat aat tca gga aaa gat ggg      48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt      96
Asn Thr Ser Ala Asn Ser Ala Asp Glu Ser Val Lys Gly Pro Asn Leu
            20                  25                  30 aca gaa ata agt aaa aaa att aca gaa tct aac gca gtt gtt ctg gct     144
Thr Glu Ile Ser Lys Lys Ile Thr Glu Ser Asn Ala Val Val Leu Ala
        35                  40                  45 gtg aaa gaa att gaa act ttg ctt gca tct ata gat gaa ctt gct act     192
Val Lys Glu Ile Glu Thr Leu Leu Ala Ser Ile Asp Glu Leu Ala Thr
 50                  55                  60 aaa gct att ggt aaa aaa ata caa caa aat ggt ggt tta gct gtc gaa     240
Lys Ala Ile Gly Lys Lys Ile Gln Gln Asn Gly Gly Leu Ala Val Glu
 65                  70                  75                  80 gcg ggg cat aat gga aca ttg tta gca ggt gct tat aca ata tca aaa     288
Ala Gly His Asn Gly Thr Leu Leu Ala Gly Ala Tyr Thr Ile Ser Lys
                85                  90                  95 cta ata aca caa aaa tta gat gga ttg aaa aat tca gaa aaa tta aag     336
Leu Ile Thr Gln Lys Leu Asp Gly Leu Lys Asn Ser Glu Lys Leu Lys
            100                 105                 110 gaa aaa att gaa aat gct aag aaa tgt tct gaa gat ttt act aaa aaa     384
Glu Lys Ile Glu Asn Ala Lys Lys Cys Ser Glu Asp Phe Thr Lys Lys
        115                 120                 125 cta gaa gga gaa cat gcg caa ctt gga att gaa aat gtt act gat gag     432
Leu Glu Gly Glu His Ala Gln Leu Gly Ile Glu Asn Val Thr Asp Glu
    130                 135                 140 aat gca aaa aaa gct att tta ata aca gat gca gct aaa gat aag ggc     480
Asn Ala Lys Lys Ala Ile Leu Ile Thr Asp Ala Ala Lys Asp Lys Gly
145                 150                 155                 160 gct gca gag ctt gaa aag cta ttt aaa gca gta gaa aac ttg gca aaa     528
Ala Ala Glu Leu Glu Lys Leu Phe Lys Ala Val Glu Asn Leu Ala Lys
                165                 170                 175 gca gct aaa gag atg ctt gct aat tca gtt aaa gag ctt aca agt cct     576
Ala Ala Lys Glu Met Leu Ala Asn Ser Val Lys Glu Leu Thr Ser Pro
            180                 185                 190 att gtg                                                             582
Ile Val

<210> SEQ ID NO 22
<211> LENGTH: 194
<212> TYPE: PRT
<213> ORGANISM: Borrelia burgdorferi

<400> SEQUENCE: 22

Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
        35                  40                  45

Val Lys Glu Ile Glu Thr Leu Leu Ala Ser Ile Asp Glu Leu Ala Thr
 50                  55                  60

Lys Ala Ile Gly Lys Lys Ile Gln Gln Asn Gly Gly Leu Ala Val Glu
65                  70                  75                  80
```

```
Ala Gly His Asn Gly Thr Leu Leu Ala Gly Ala Tyr Thr Ile Ser Lys
             85                  90                  95

Leu Ile Thr Gln Lys Leu Asp Gly Leu Lys Asn Ser Glu Lys Leu Lys
            100                 105                 110

Glu Lys Ile Glu Asn Ala Lys Lys Cys Ser Glu Asp Phe Thr Lys Lys
            115                 120                 125

Leu Glu Gly Glu His Ala Gln Leu Gly Ile Glu Asn Val Thr Asp Glu
            130                 135                 140

Asn Ala Lys Lys Ala Ile Leu Ile Thr Asp Ala Ala Lys Asp Lys Gly
145                 150                 155                 160

Ala Ala Glu Leu Glu Lys Leu Phe Lys Ala Val Glu Asn Leu Ala Lys
                165                 170                 175

Ala Ala Lys Glu Met Leu Ala Asn Ser Val Lys Glu Leu Thr Ser Pro
            180                 185                 190

Ile Val

<210> SEQ ID NO 23
<211> LENGTH: 1128
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1128)

<400> SEQUENCE: 23 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
             20                  25                  30 att acg gat tct aat gcg gtt tta ctt gct gtg aaa gag gtt gaa gcg    144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa    192
Leu Leu Ser Ser Ile Asp Glu Ile Ala Ala Lys Ala Ile Gly Lys Lys
     50                  55                  60 ata cac caa aat aat ggt ttg gat acc gaa tat aat cac aat gga tca    240
Ile His Gln Asn Asn Gly Leu Asp Thr Glu Tyr Asn His Asn Gly Ser
 65                  70                  75                  80 ttg tta gcg gga gct tat gca ata tca acc cta ata aaa caa aaa tta    288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag    336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat    384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta    432
Leu Gly Lys Glu Gly Val Thr Asp Ala Asp Ala Lys Glu Ala Ile Leu
            130                 135                 140 aaa aca aat ggt act aaa act aaa ggt gct gaa gaa ctt gga aaa tta    480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct    528
Phe Glu Ser Val Glu Val Leu Ser Lys Ala Ala Lys Glu Met Leu Ala
```

-continued

```
                        165                 170                 175
aat tca gtt aaa gag ctt aca agc cct gtt gtg gca gaa agt cca gcc      576
Asn Ser Val Lys Glu Leu Thr Ser Pro Val Val Ala Glu Ser Pro Ala
            180                 185                 190 atg gta aat aat tca ggg aaa gat ggg aat aca tct gca aat tct gct      624
Met Val Asn Asn Ser Gly Lys Asp Gly Asn Thr Ser Ala Asn Ser Ala
            195                 200                 205 gat gag tct gtt aaa ggg cct aat ctt aca gaa ata agt aaa aaa att      672
Asp Glu Ser Val Lys Gly Pro Asn Leu Thr Glu Ile Ser Lys Lys Ile
    210                 215                 220 aca gaa tct aac gca gtt gtt ctc gcc gtg aaa gaa gtt gaa act ttg      720
Thr Glu Ser Asn Ala Val Val Leu Ala Val Lys Glu Val Glu Thr Leu
225                 230                 235                 240 ctt aca tct ata gat gag ctt gct aaa gct att ggt aaa aaa ata aaa      768
Leu Thr Ser Ile Asp Glu Leu Ala Lys Ala Ile Gly Lys Lys Ile Lys
                245                 250                 255 aac gat gtt agt tta gat aat gag gca gat cac aac gga tca tta ata      816
Asn Asp Val Ser Leu Asp Asn Glu Ala Asp His Asn Gly Ser Leu Ile
            260                 265                 270 tca gga gca tat tta att tca aac tta ata aca aaa aaa ata agt gca      864
Ser Gly Ala Tyr Leu Ile Ser Asn Leu Ile Thr Lys Lys Ile Ser Ala
        275                 280                 285 ata aaa gat tca gga gaa ttg aag gca gaa att gaa aag gct aag aaa      912
Ile Lys Asp Ser Gly Glu Leu Lys Ala Glu Ile Glu Lys Ala Lys Lys
    290                 295                 300 tgt tct gaa gaa ttt act gct aaa tta aaa ggt gaa cac aca gat ctt      960
Cys Ser Glu Glu Phe Thr Ala Lys Leu Lys Gly Glu His Thr Asp Leu
305                 310                 315                 320 ggt aaa gaa ggc gtt act gat gat aat gca aaa aaa gcc att tta aaa     1008
Gly Lys Glu Gly Val Thr Asp Asp Asn Ala Lys Lys Ala Ile Leu Lys
                325                 330                 335 aca aat aat gat aaa act aag ggc gct gat gaa ctt gaa aag tta ttt     1056
Thr Asn Asn Asp Lys Thr Lys Gly Ala Asp Glu Leu Glu Lys Leu Phe
            340                 345                 350 gaa tca gta aaa aac ttg tca aaa gca gct aaa gag atg ctt act aat     1104
Glu Ser Val Lys Asn Leu Ser Lys Ala Ala Lys Glu Met Leu Thr Asn
        355                 360                 365 tca gtt aaa gag ctt aca agc taa                                     1128
Ser Val Lys Glu Leu Thr Ser  *
    370                 375
```

<210> SEQ ID NO 24
<211> LENGTH: 375
<212> TYPE: PRT
<213> ORGANISM: Artificial Sequence
<220> FEATURE:
<223> OTHER INFORMATION: OspC Chimera

<400> SEQUENCE: 24

```
Met Ala Cys Asn Asn Ser Gly Lys Asp Gly Asn Thr Ser Ala Asn Ser
  1               5                  10                  15

Ala Asp Glu Ser Val Lys Gly Pro Asn Leu Thr Glu Ile Ser Lys Lys
             20                  25                  30

Ile Thr Asp Ser Asn Ala Val Leu Leu Ala Val Lys Glu Val Glu Ala
         35                  40                  45

Leu Leu Ser Ser Ile Asp Glu Ile Ala Ala Lys Ala Ile Gly Lys Lys
     50                  55                  60

Ile His Gln Asn Asn Gly Leu Asp Thr Glu Tyr Asn His Asn Gly Ser
 65                  70                  75                  80
```

| | | | | | | | | | | | | |
|---|---|---|---|---|---|---|---|---|---|---|---|---|
|Leu|Leu|Ala|Gly|Ala|Tyr|Ala|Ile|Ser|Thr|Leu|Ile|Lys|Gln|Lys|Leu|
| | | | |85| | | |90| | | |95| | | |
|Asp|Gly|Leu|Lys|Asn|Glu|Gly|Leu|Lys|Glu|Lys|Ile|Asp|Ala|Ala|Lys|
| | | |100| | | | |105| | | |110| | | |
|Lys|Cys|Ser|Glu|Thr|Phe|Thr|Asn|Lys|Leu|Lys|Glu|Lys|His|Thr|Asp|
| | | |115| | | | |120| | | |125| | | |
|Leu|Gly|Lys|Glu|Gly|Val|Thr|Asp|Ala|Asp|Ala|Lys|Glu|Ala|Ile|Leu|
| | | |130| | | | |135| | | |140| | | |
|Lys|Thr|Asn|Gly|Thr|Lys|Thr|Lys|Gly|Ala|Glu|Glu|Leu|Gly|Lys|Leu|
|145| | | |150| | | | |155| | | |160| | |
|Phe|Glu|Ser|Val|Glu|Val|Leu|Ser|Lys|Ala|Ala|Lys|Glu|Met|Leu|Ala|
| | | | |165| | | |170| | | |175| | | |
|Asn|Ser|Val|Lys|Glu|Leu|Thr|Ser|Pro|Val|Val|Ala|Glu|Ser|Pro|Ala|
| | | |180| | | | |185| | | |190| | | |
|Met|Val|Asn|Asn|Ser|Gly|Lys|Asp|Gly|Asn|Thr|Ser|Ala|Asn|Ser|Ala|
| | | |195| | | | |200| | | |205| | | |
|Asp|Glu|Ser|Val|Lys|Gly|Pro|Asn|Leu|Thr|Glu|Ile|Ser|Lys|Lys|Ile|
| | | |210| | | | |215| | | |220| | | |
|Thr|Glu|Ser|Asn|Ala|Val|Val|Leu|Ala|Val|Lys|Glu|Val|Glu|Thr|Leu|
|225| | | |230| | | | |235| | | |240| | |
|Leu|Thr|Ser|Ile|Asp|Glu|Leu|Ala|Lys|Ala|Ile|Gly|Lys|Lys|Ile|Lys|
| | | |245| | | | |250| | | |255| | | |
|Asn|Asp|Val|Ser|Leu|Asp|Asn|Glu|Ala|Asp|His|Asn|Gly|Ser|Leu|Ile|
| | | |260| | | | |265| | | |270| | | |
|Ser|Gly|Ala|Tyr|Leu|Ile|Ser|Asn|Leu|Ile|Thr|Lys|Lys|Ile|Ser|Ala|
| | | |275| | | | |280| | | |285| | | |
|Ile|Lys|Asp|Ser|Gly|Glu|Leu|Lys|Ala|Glu|Ile|Glu|Lys|Ala|Lys|Lys|
| | | |290| | | | |295| | | |300| | | |
|Cys|Ser|Glu|Glu|Phe|Thr|Ala|Lys|Leu|Lys|Gly|Glu|His|Thr|Asp|Leu|
|305| | | |310| | | | |315| | | |320| | |
|Gly|Lys|Glu|Gly|Val|Thr|Asp|Asp|Asn|Ala|Lys|Lys|Ala|Ile|Leu|Lys|
| | | |325| | | | |330| | | |335| | | |
|Thr|Asn|Asn|Asp|Lys|Thr|Lys|Gly|Ala|Asp|Glu|Leu|Glu|Lys|Leu|Phe|
| | | |340| | | | |345| | | |350| | | |
|Glu|Ser|Val|Lys|Asn|Leu|Ser|Lys|Ala|Ala|Lys|Glu|Met|Leu|Thr|Asn|
| | | |355| | | | |360| | | |365| | | |
|Ser|Val|Lys|Glu|Leu|Thr|Ser| | | | | | | | | |
| | | |370| | | |375| | | | | | | | |

```
<210> SEQ ID NO 25
<211> LENGTH: 1124
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1124)

<400> SEQUENCE: 25 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
```

```
                Ile Thr Asp Ser Asn Ala Val Leu Leu Ala Val Lys Glu Val Glu Ala
                         35                  40                  45 ttg ctg tca tct ata gat gaa att gct gct aaa gct att ggt aaa aaa       192
Leu Leu Ser Ser Ile Asp Glu Ile Ala Ala Lys Ala Ile Gly Lys Lys
 50                  55                  60 ata cac caa aat aat ggt ttg gat acc gaa tat aat cac aat gga tca       240
Ile His Gln Asn Asn Gly Leu Asp Thr Glu Tyr Asn His Asn Gly Ser
 65                  70                  75                  80 ttg tta gcg gga gct tat gca ata tca acc cta ata aaa caa aaa tta       288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag       336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat       384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta       432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta       480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct       528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca gcc       576
Asn Ser Val Lys Glu Leu Thr Ser Pro Val Val Ala Glu Ser Pro Ala
            180                 185                 190 atg gta aat aat tca gga aaa gat ggg aat aca tct gca aat tct gct       624
Met Val Asn Asn Ser Gly Lys Asp Gly Asn Thr Ser Ala Asn Ser Ala
        195                 200                 205 gat gag tct gtt aaa ggg cct aat ctt aca gaa ata agt aaa aaa att       672
Asp Glu Ser Val Lys Gly Pro Asn Leu Thr Glu Ile Ser Lys Lys Ile
    210                 215                 220 aca gaa tct aac gca gtt gtt ctg gct gtg aaa gaa att gaa act ttg       720
Thr Glu Ser Asn Ala Val Val Leu Ala Val Lys Glu Ile Glu Thr Leu
225                 230                 235                 240 ctt gca tct ata gat gaa ctt gct act aaa gct att ggt aaa aaa ata       768
Leu Ala Ser Ile Asp Glu Leu Ala Thr Lys Ala Ile Gly Lys Lys Ile
                245                 250                 255 caa caa aat ggt ggt tta gct gtc gaa gcg ggg cat aat gga aca ttg       816
Gln Gln Asn Gly Gly Leu Ala Val Glu Ala Gly His Asn Gly Thr Leu
            260                 265                 270 tta gca ggt gct tat aca ata tca aaa cta ata aca caa aaa tta gat       864
Leu Ala Gly Ala Tyr Thr Ile Ser Lys Leu Ile Thr Gln Lys Leu Asp
        275                 280                 285 gga ttg aaa aat tca gaa aaa tta aag gaa aaa att gaa aat gct aag       912
Gly Leu Lys Asn Ser Glu Lys Leu Lys Glu Lys Ile Glu Asn Ala Lys
    290                 295                 300 aaa tgt tct gaa gat ttt act aaa aaa cta gaa gga gaa cat gcg caa       960
Lys Cys Ser Glu Asp Phe Thr Lys Lys Leu Glu Gly Glu His Ala Gln
305                 310                 315                 320 ctt gga att gaa aat gtt act gat gag aat gca aaa aaa gct att tta      1008
Leu Gly Ile Glu Asn Val Thr Asp Glu Asn Ala Lys Lys Ala Ile Leu
                325                 330                 335 ata aca gat gca gct aaa gat aag ggc gct gca gag ctt gaa aag cta      1056
Ile Thr Asp Ala Ala Lys Asp Lys Gly Ala Ala Glu Leu Glu Lys Leu
            340                 345                 350
```

```
ttt aaa gca gta gaa aac ttg gca aaa gca gct aaa gag atg ctt gct    1104
Phe Lys Ala Val Glu Asn Leu Ala Lys Ala Ala Lys Glu Met Leu Ala
        355                 360                 365 aat tca gtt aaa gag ctt ac                                          1124
Asn Ser Val Lys Glu Leu
    370

<210> SEQ ID NO 26
<211> LENGTH: 374
<212> TYPE: PRT
<213> ORGANISM: Artificial Sequence
<220> FEATURE:
<223> OTHER INFORMATION: OspC Chimera

<400> SEQUENCE: 26

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25

```
                325                 330                 335
Ile Thr Asp Ala Ala Lys Asp Lys Gly Ala Ala Glu Leu Glu Lys Leu
            340                 345                 350

Phe Lys Ala Val Glu Asn Leu Ala Lys Ala Ala Lys Glu Met Leu Ala
        355                 360                 365

Asn Ser Val Lys Glu Leu
    370

<210> SEQ ID NO 27
<211> LENGTH: 1137
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1137)

<400> SEQUENCE: 27 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
             20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
     50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta     480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa     576
Asn Ser Val Lys Glu Leu Thr Ser Pro Val Val Ala Glu Ser Pro Lys
            180                 185                 190 aaa cct tcc atg gta aat aat tca ggg aaa gat ggg aat aca tct gca     624
Lys Pro Ser Met Val Asn Asn Ser Gly Lys Asp Gly Asn Thr Ser Ala
        195                 200                 205 aat tct gct gat gag tct gtt aaa ggg cct aat ctt aca gaa ata agt     672
Asn Ser Ala Asp Glu Ser Val Lys Gly Pro Asn Leu Thr Glu Ile Ser
    210                 215                 220
```

```
aaa aaa att aca gaa tct aac gca gtt gtt ctc gcc gtg aaa gaa gtt      720
Lys Lys Ile Thr Glu Ser Asn Ala Val Val Leu Ala Val Lys Glu Val
225                 230                 235                 240 gaa act ttg ctt aca tct ata gat gag ctt gct aaa gct att ggt aaa      768
Glu Thr Leu Leu Thr Ser Ile Asp Glu Leu Ala Lys Ala Ile Gly Lys
                245                 250                 255 aaa ata aaa aac gat gtt agt tta gat aat gag gca gat cac aac gga      816
Lys Ile Lys Asn Asp Val Ser Leu Asp Asn Glu Ala Asp His Asn Gly
            260                 265                 270 tca tta ata tca gga gca tat tta att tca aac tta ata aca aaa aaa      864
Ser Leu Ile Ser Gly Ala Tyr Leu Ile Ser Asn Leu Ile Thr Lys Lys
        275                 280                 285 ata agt gca ata aaa gat tca gga gaa ttg aag gca gaa att gaa aag      912
Ile Ser Ala Ile Lys Asp Ser Gly Glu Leu Lys Ala Glu Ile Glu Lys
    290                 295                 300 gct aag aaa tgt tct gaa gaa ttt act gct aaa tta aaa ggt gaa cac      960
Ala Lys Lys Cys Ser Glu Glu Phe Thr Ala Lys Leu Lys Gly Glu His
305                 310                 315                 320 aca gat ctt ggt aaa gaa ggc gtt act gat gat aat gca aaa aaa gcc     1008
Thr Asp Leu Gly Lys Glu Gly Val Thr Asp Asp Asn Ala Lys Lys Ala
                325                 330                 335 att tta aaa aca aat aat gat aaa act aag ggc gct gat gaa ctt gaa     1056
Ile Leu Lys Thr Asn Asn Asp Lys Thr Lys Gly Ala Asp Glu Leu Glu
            340                 345                 350 aag tta ttt gaa tca gta aaa aac ttg tca aaa gca gct aaa gag atg     1104
Lys Leu Phe Glu Ser Val Lys Asn Leu Ser Lys Ala Ala Lys Glu Met
        355                 360                 365 ctt act aat tca gtt aaa gag ctt aca agc taa                         1137
Leu Thr Asn Ser Val Lys Glu Leu Thr Ser *
    370                 375

<210> SEQ ID NO 28
<211> LENGTH: 378
<212> TYPE: PRT
<213> ORGANISM: Artificial Sequence
<220> FEATURE:
<223> OTHER INFORMATION: OspC Chimera

<400> SEQUENCE: 28

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
                20                  25                  30

Ile Thr Asp Ser Asn Ala Val Leu Leu Ala Val Lys Glu Val Glu Ala
            35                  40                  45

Leu Leu Ser Ser Ile Asp Glu Ile Ala Ala Lys Ala Ile Gly Lys Lys
        50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
```

```
                145                 150                 155                 160
        Phe Glu Ser Val Glu Val Leu Ser Lys Ala Ala Lys Glu Met Leu Ala
                        165                 170                 175

Asn Ser Val Lys Glu Leu Thr Ser Pro Val Val Ala Glu Ser Pro Lys
                        180                 185                 190

Lys Pro Ser Met Val Asn Asn Ser Gly Lys Asp Gly Asn Thr Ser Ala
                        195                 200                 205

Asn Ser Ala Asp Glu Ser Val Lys Gly Pro Asn Leu Thr Glu Ile Ser
                210                 215                 220

Lys Lys Ile Thr Glu Ser Asn Ala Val Leu Ala Val Lys Glu Val
        225                 230                 235                 240

Glu Thr Leu Leu Thr Ser Ile Asp Glu Leu Ala Lys Ala Ile Gly Lys
                        245                 250                 255

Lys Ile Lys Asn Asp Val Ser Leu Asp Asn Glu Ala Asp His Asn Gly
                        260                 265                 270

Ser Leu Ile Ser Gly Ala Tyr Leu Ile Ser Asn Leu Ile Thr Lys Lys
                        275                 280                 285

Ile Ser Ala Ile Lys Asp Ser Gly Glu Leu Lys Ala Glu Ile Glu Lys
                290                 295                 300

Ala Lys Lys Cys Ser Glu Glu Phe Thr Ala Lys Leu Lys Gly Glu His
        305                 310                 315                 320

Thr Asp Leu Gly Lys Glu Gly Val Thr Asp Asp Ala Lys Lys Ala
                        325                 330                 335

Ile Leu Lys Thr Asn Asn Asp Lys Thr Lys Gly Ala Asp Glu Leu Glu
                        340                 345                 350

Lys Leu Phe Glu Ser Val Lys Asn Leu Ser Lys Ala Ala Lys Glu Met
                        355                 360                 365

Leu Thr Asn Ser Val Lys Glu Leu Thr Ser
                        370                 375

<210> SEQ ID NO 29
<211> LENGTH: 1133
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1133)

<400> SEQUENCE: 29 atg gct tgt aat aat tca ggg aaa gat ggg aat aca tct gca aat tct        48
Met Ala Cys Asn Asn Ser Gly Lys Asp Gly Asn Thr Ser Ala Asn Ser
  1               5                  10                  15 gct gat gag tct gtt aaa ggg cct aat ctt aca gaa ata aat aaa aaa        96
Ala Asp Glu Ser Val Lys Gly Pro Asn Leu Thr Glu Ile Asn Lys Lys
                 20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
             35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
         50                  55                  60 ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
```

```
                         85                    90                    95
gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190 aaa cct tcc atg gta aat aat tca gga aaa gat ggg aat aca tct gca      624
Lys Pro Ser Met Val Asn Asn Ser Gly Lys Asp Gly Asn Thr Ser Ala
        195                 200                 205 aat tct gct gat gag tct gtt aaa ggg cct aat ctt aca gaa ata agt      672
Asn Ser Ala Asp Glu Ser Val Lys Gly Pro Asn Leu Thr Glu Ile Ser
    210                 215                 220 aaa aaa att aca gaa tct aac gca gtt gtt ctg gct gtg aaa gaa att      720
Lys Lys Ile Thr Glu Ser Asn Ala Val Val Leu Ala Val Lys Glu Ile
225                 230                 235                 240 gaa act ttg ctt gca tct ata gat gaa ctt gct act aaa gct att ggt      768
Glu Thr Leu Leu Ala Ser Ile Asp Glu Leu Ala Thr Lys Ala Ile Gly
                245                 250                 255 aaa aaa ata caa caa aat ggt ggt tta gct gtc gaa gcg ggg cat aat      816
Lys Lys Ile Gln Gln Asn Gly Gly Leu Ala Val Glu Ala Gly His Asn
            260                 265                 270 gga aca ttg tta gca ggt gct tat aca ata tca aaa cta ata aca caa      864
Gly Thr Leu Leu Ala Gly Ala Tyr Thr Ile Ser Lys Leu Ile Thr Gln
        275                 280                 285 aaa tta gat gga ttg aaa aat tca gaa aaa tta aag gaa aaa att gaa      912
Lys Leu Asp Gly Leu Lys Asn Ser Glu Lys Leu Lys Glu Lys Ile Glu
    290                 295                 300 aat gct aag aaa tgt tct gaa gat ttt act aaa aaa cta gaa gga gaa      960
Asn Ala Lys Lys Cys Ser Glu Asp Phe Thr Lys Lys Leu Glu Gly Glu
305                 310                 315                 320 cat gcg caa ctt gga att gaa aat gtt act gat gag aat gca aaa aaa     1008
His Ala Gln Leu Gly Ile Glu Asn Val Thr Asp Glu Asn Ala Lys Lys
                325                 330                 335 gct att tta ata aca gat gca gct aaa gat aag ggc gct gca gag ctt     1056
Ala Ile Leu Ile Thr Asp Ala Ala Lys Asp Lys Gly Ala Ala Glu Leu
            340                 345                 350 gaa aag cta ttt aaa gca gta gaa aac ttg gca aaa gca gct aaa gag     1104
Glu Lys Leu Phe Lys Ala Val Glu Asn Leu Ala Lys Ala Ala Lys Glu
        355                 360                 365 atg ctt gct aat tca gtt aaa gag ctt ac                              1133
Met Leu Ala Asn Ser Val Lys Glu Leu
    370                 375
```

<210> SEQ ID NO 30
<211> LENGTH: 377
<212> TYPE: PRT
<213> ORGANISM: Artificial Sequence
<220> FEATURE:
<223> OTHER INFORMATION: OspC Chimera

<400> SEQUENCE: 30

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
             20                  25                  30

Ile Thr Asp Ser Asn Ala Val Leu Leu Ala Val Lys Glu Val Glu Ala
         35                  40                  45

Leu Leu Ser Ser

<211> LENGTH: 1112
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1112)

<400> SEQUENCE: 31

| | | | | | | | | | | | | | | | | |
|---|---|---|

```
gca ata tct gac cta ata gca gaa aaa tta aat gta ttg aaa aat gaa      864
Ala Ile Ser Asp Leu Ile Ala Glu Lys Leu Asn Val Leu Lys Asn Glu
    275                 280                 285 gaa tta aag gaa aag att gat aca gct aag caa tgt tct aca gaa ttt      912
Glu Leu Lys Glu Lys Ile Asp Thr Ala Lys Gln Cys Ser Thr Glu Phe
290                 295                 300 act aat aaa cta aaa agt gaa cat gca gtg ctt ggt ctg gac aat ctt      960
Thr Asn Lys Leu Lys Ser Glu His Ala Val Leu Gly Leu Asp Asn Leu
305                 310                 315                 320 act gat gat aat gca caa aga gct att tta aaa aaa cat gca aat aaa     1008
Thr Asp Asp Asn Ala Gln Arg Ala Ile Leu Lys Lys His Ala Asn Lys
                325                 330                 335 gat aag ggt gct gca gaa ctt gaa aag tta ttt aaa gcg gta gaa aac     1056
Asp Lys Gly Ala Ala Glu Leu Glu Lys Leu Phe Lys Ala Val Glu Asn
            340                 345                 350 tta tca aaa gca gct caa gac aca tta aaa aat gct gtt aaa gag ctt     1104
Leu Ser Lys Ala Ala Gln Asp Thr Leu Lys Asn Ala Val Lys Glu Leu
        355                 360                 365 aca agt cc                                                          1112
Thr Ser
    370

<210> SEQ ID NO 32
<211> LENGTH: 370
<212> TYPE: PRT
<213> ORGANISM: Artificial Sequence
<220> FEATURE:
<223> OTHER INFORMATION: OspC Chimera

<400> SEQUENCE: 32

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
             20                  25                  30

Ile Thr Asp Ser Asn Ala Val Leu Leu Ala Val Lys Glu Val Glu Ala
         35                  40                  45

Leu Leu Ser Ser Ile Asp Glu Leu Ala Lys Ala Ile Gly Lys Lys Ile
 50                  55                  60

Lys Asn Asp Gly Ser Leu Asp Asn Gl

```
Ala Val Val Leu Ala Val Lys Glu Val Glu Thr Leu Ala Ser Ile
225                 230                 235                 240

Asp Glu Leu Ala Thr Lys Ala Ile Gly Lys Lys Ile Gly Asn Asn Gly
                245                 250                 255

Leu Glu Ala Asn Gln Ser Lys Asn Thr Ser Leu Leu Ser Gly Ala Tyr
                260                 265                 270

Ala Ile Ser Asp Leu Ile Ala Glu Lys Leu Asn Val Leu Lys Asn Glu
                275                 280                 285

Glu Leu Lys Glu Lys Ile Asp Thr Ala Lys Gln Cys Ser Thr Glu Phe
                290                 295                 300

Thr Asn Lys Leu Lys Ser Glu His Ala Val Leu Gly Leu Asp Asn Leu
305                 310                 315                 320

Thr Asp Asp Asn Ala Gln Arg Ala Ile Leu Lys Lys His Ala Asn Lys
                325                 330                 335

Asp Lys Gly Ala Ala Glu Leu Glu Lys Leu Phe Lys Ala Val Glu Asn
                340                 345                 350

Leu Ser Lys Ala Ala Gln Asp Thr Leu Lys Asn Ala Val Lys Glu Leu
                355                 360                 365

Thr Ser
    370

<210> SEQ ID NO 33
<211> LENGTH: 1113
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1113)

<400> SEQUENCE: 33 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
    50                  55                  60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt     288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag     336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag     384
Lys Cys Ser Glu Glu Phe Ser Thr Lys Leu Lys Asp Asn His Ala Gln
        115                 120                 125 ctt ggt ata cag ggc gtt act gat gaa aat gca aaa aaa gct att tta     432
Leu Gly Ile Gln Gly Val Thr Asp Glu Asn Ala Lys Lys Ala Ile Leu
    130                 135                 140
```

```
aaa gca aat gca gcg ggt aaa gat aag ggc gtt gaa gaa ctt gaa aag       480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt       528
Leu Ser Gly Ser Leu Glu Ser Leu Ser Lys Ala Ala Lys Glu Met Leu
            165                 170                 175 gct aat tca gtt aaa gag ctt aca agc cct gtt gtc cat ggt aat aat       576
Ala Asn Ser Val Lys Glu Leu Thr Ser Pro Val Val His Gly Asn Asn
        180                 185                 190 tca ggg aaa gat ggg aat aca tct gca aat tct gct gat gag tct gtt       624
Ser Gly Lys Asp Gly Asn Thr Ser Ala Asn Ser Ala Asp Glu Ser Val
    195                 200                 205 aaa ggg cct aat ctt aca gaa ata agt aaa aaa att aca gaa tct aac       672
Lys Gly Pro Asn Leu Thr Glu Ile Ser Lys Lys Ile Thr Glu Ser Asn
210                 215                 220 gca gtt gtt ctc gcc gtg aaa gaa gtt gaa act ttg ctt aca tct ata       720
Ala Val Val Leu Ala Val Lys Glu Val Glu Thr Leu Leu Thr Ser Ile
225                 230                 235                 240 gat gag ctt gct aaa gct att ggt aaa aaa ata aaa aac gat gtt agt       768
Asp Glu Leu Ala Lys Ala Ile Gly Lys Lys Ile Lys Asn Asp Val Ser
            245                 250                 255 tta gat aat gag gca gat cac aac gga tca tta ata tca gga gca tat       816
Leu Asp Asn Glu Ala Asp His Asn Gly Ser Leu Ile Ser Gly Ala Tyr
        260                 265                 270 tta att tca aac tta ata aca aaa aaa ata agt gca ata aaa gat tca       864
Leu Ile Ser Asn Leu Ile Thr Lys Lys Ile Ser Ala Ile Lys Asp Ser
    275                 280                 285 gga gaa ttg aag gca gaa att gaa aag gct aag aaa tgt tct gaa gaa       912
Gly Glu Leu Lys Ala Glu Ile Glu Lys Ala Lys Lys Cys Ser Glu Glu
290                 295                 300 ttt act gct aaa tta aaa ggt gaa cac aca gat ctt ggt aaa gaa ggc       960
Phe Thr Ala Lys Leu Lys Gly Glu His Thr Asp Leu Gly Lys Glu Gly
305                 310                 315                 320 gtt act gat gat aat gca aaa aaa gcc att tta aaa aca aat aat gat      1008
Val Thr Asp Asp Asn Ala Lys Lys Ala Ile Leu Lys Thr Asn Asn Asp
            325                 330                 335 aaa act aag ggc gct gat gaa ctt gaa aag tta ttt gaa tca gta aaa      1056
Lys Thr Lys Gly Ala Asp Glu Leu Glu Lys Leu Phe Glu Ser Val Lys
        340                 345                 350 aac ttg tca aaa gca gct aaa gag atg ctt act aat tca gtt aaa gag      1104
Asn Leu Ser Lys Ala Ala Lys Glu Met Leu Thr Asn Ser Val Lys Glu
    355                 360                 365 ctt aca agc                                                          1113
Leu Thr Ser
    370

<210> SEQ ID NO 34
<211> LENGTH: 371
<212> TYPE: PRT
<213> ORGANISM: Artificial Sequence
<220> FEATURE:
<223> OTHER INFORMATION: OspC Chimera

<400> SEQUENCE: 34

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45
```

```
Leu Leu Ser Ser Ile Asp Glu Leu Ala Lys Ala Ile Gly Lys Lys Ile
 50                  55                  60
Lys Asn Asp Gly Ser Leu Asp Asn Glu Ala Asn Arg Asn Glu Ser Leu
 65                  70                  75                  80
Leu Ala Gly Ala Tyr Thr Ile Ser Thr Leu Ile Thr Gln Lys Leu Ser
                 85                  90                  95
Lys Leu Asn Gly Ser Glu Gly Leu Lys Glu Lys Ile Ala Ala Ala Lys
            100                 105                 110
Lys Cys Ser Glu Glu Phe Ser Thr Lys Leu Lys Asp Asn His Ala Gln
            115                 120                 125
Leu Gly Ile Gln Gly Val Thr Asp Glu Asn Ala Lys Lys Ala Ile Leu
        130                 135                 140
Lys Ala Asn Ala Ala Gly Lys Asp Lys Gly Val Glu Glu Leu Glu Lys
145                 150                 155                 160
Leu Ser Gly Ser Leu Glu Ser Leu Ser Lys Ala Lys Glu Met Leu
                165                 170                 175
Ala Asn Ser Val Lys Glu Leu Thr Ser Pro Val Val His Gly Asn Asn
            180                 185                 190
Ser Gly Lys Asp Gly Asn Thr Ser Ala Asn Ser Ala Asp Glu Ser Val
        195                 200                 205
Lys Gly Pro Asn Leu Thr Glu Ile Ser Lys Lys Ile Thr Glu Ser Asn
210                 215                 220
Ala Val Val Leu Ala Val Lys Glu Val Glu Thr Leu Leu Thr Ser Ile
225                 230                 235                 240
Asp Glu Leu Ala Lys Ala Ile Gly Lys Lys Ile Lys Asn Asp Val Ser
                245                 250                 255
Leu Asp Asn Glu Ala Asp His Asn Gly Ser Leu Ile Ser Gly Ala Tyr
            260                 265                 270
Leu Ile Ser Asn Leu Ile Thr Lys Lys Ile Ser Ala Ile Lys Asp Ser
        275                 280                 285
Gly Glu Leu Lys Ala Glu Ile Glu Lys Ala Lys Lys Cys Ser Glu Glu
290                 295                 300
Phe Thr Ala Lys Leu Lys Gly Glu His Thr Asp Leu Gly Lys Glu Gly
305                 310                 315                 320
Val Thr Asp Asp Asn Ala Lys Lys Ala Ile Leu Lys Thr Asn Asn Asp
                325                 330                 335
Lys Thr Lys Gly Ala Asp Glu Leu Glu Lys Leu Phe Glu Ser Val Lys
            340                 345                 350
Asn Leu Ser Lys Ala Ala Lys Glu Met Leu Thr Asn Ser Val Lys Glu
        355                 360                 365
Leu Thr Ser
    370

<210> SEQ ID NO 35
<211> LENGTH: 1112
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1112)

<400> SEQUENCE: 35 atg gct tgt aat aat tca ggg aaa gat ggg aat aca tct gca aat tct    48
Met Ala Cys Asn Asn Ser Gly Lys Asp Gly Asn Thr -continued

```
            1               5              10              15
gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                 20              25              30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
             35              40              45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
         50              55              60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
 65              70              75              80 tta gca gga gct tat aca ata tca acc tta ata aca caa aaa tta agt     288
Leu Ala Gly Ala Tyr Thr Ile Ser Thr Leu Ile Thr Gln Lys Leu Ser
                 85              90              95 aaa tta aac gga tca gaa ggt tta aag gaa aag att gcc gca gct aag     336
Lys Leu Asn Gly Ser Glu Gly Leu Lys Glu Lys Ile Ala Ala Ala Lys
             100             105             110 aaa tgc tct gaa gag ttt agt act aaa cta aaa gat aat cat gca cag     384
Lys Cys Ser Glu Glu Phe Ser Thr Lys Leu Lys Asp Asn His Ala Gln
         115             120             125 ctt ggt ata cag ggc gtt act gat gaa aat gca aaa aaa gct att tta     432
Leu Gly Ile Gln Gly Val Thr Asp Glu Asn Ala Lys Lys Ala Ile Leu
     130             135             140 aaa gca aat gca gcg ggt aaa gat aag ggc gtt gaa gaa ctt gaa aag     480
Lys Ala Asn Ala Ala Gly Lys Asp Lys Gly Val Glu Glu Leu Glu Lys
145             150             155             160 ttg tcc gga tca tta gaa agc tta tca aaa gca gct aaa gag atg ctt     528
Leu Ser Gly Ser Leu Glu Ser Leu Ser Lys Ala Ala Lys Glu Met Leu
                 165             170             175 gct aat tca gtt aaa gag ctt aca agc cct gtt gtc cat ggt aat aat     576
Ala Asn Ser Val Lys Glu Leu Thr Ser Pro Val Val His Gly Asn Asn
             180             185             190 tca gga aaa gat ggg aat aca tct gca aat tct gct gat gag tct gtt     624
Ser Gly Lys Asp Gly Asn Thr Ser Ala Asn Ser Ala Asp Glu Ser Val
         195             200             205 aaa ggg cct aat ctt aca gaa ata agt aaa aaa att aca gaa tct aac     672
Lys Gly Pro Asn Leu Thr Glu Ile Ser Lys Lys Ile Thr Glu Ser Asn
     210             215             220 gca gtt gtt ctg gct gtg aaa gaa att gaa act ttg ctt gca tct ata     720
Ala Val Val Leu Ala Val Lys Glu Ile Glu Thr Leu Leu Ala Ser Ile
225             230             235             240 gat gaa ctt gct act aaa gct att ggt aaa aaa ata caa caa aat ggt     768
Asp Glu Leu Ala Thr Lys Ala Ile Gly Lys Lys Ile Gln Gln Asn Gly
                 245             250             255 ggt tta gct gtc gaa gcg ggg cat aat gga aca ttg tta gca ggt gct     816
Gly Leu Ala Val Glu Ala Gly His Asn Gly Thr Leu Leu Ala Gly Ala
             260             265             270 tat aca ata tca aaa cta ata aca caa aaa tta gat gga ttg aaa aat     864
Tyr Thr Ile Ser Lys Leu Ile Thr Gln Lys Leu Asp Gly Leu Lys Asn
         275             280             285 tca gaa aaa tta aag gaa aaa att gaa aat gct aag aaa tgt tct gaa     912
Ser Glu Lys Leu Lys Glu Lys Ile Glu Asn Ala Lys Lys Cys Ser Glu
     290             295             300 gat ttt act aaa aaa cta gaa gga gaa cat gcg caa ctt gga att gaa     960
Asp Phe Thr Lys Lys Leu Glu Gly Glu His Ala Gln Leu Gly Ile Glu
305             310             315             320 aat gtt act gat gag aat gca aaa aaa gct att tta ata aca gat gca    1008
```

```
Asn Val Thr Asp Glu Asn Ala Lys Lys Ala Ile Leu Ile Thr Asp Ala
                325                 330                 335 gct aaa gat aag ggc gct gca gag ctt gaa aag cta ttt aaa gca gta      1056
Ala Lys Asp Lys Gly Ala Ala Glu Leu Glu Lys Leu Phe Lys Ala Val
            340                 345                 350 gaa aac ttg gca aaa gca gct aaa gag atg ctt gct aat tca gtt aaa      1104
Glu Asn Leu Ala Lys Ala Ala Lys Glu Met Leu Ala Asn Ser Val Lys
            355                 360                 365 gag ctt ac                                                           1112
Glu Leu
    370

<210> SEQ ID NO 36
<211> LENGTH: 370
<212> TYPE: PRT
<213> ORGANISM: Artificial Sequence
<220> FEATURE:
<223> OTHER INFORMATION: OspC Chimera

<400> SEQUENCE: 36

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu

```
Ser Glu Lys Leu Lys Glu Lys Ile Glu Asn Ala Lys Lys Cys Ser Glu
    290                 295                 300

Asp Phe Thr Lys Lys Leu Glu Gly Glu His Ala Gln Leu Gly Ile Glu
305                 310                 315                 320

Asn Val Thr Asp Glu Asn Ala Lys Lys Ala Ile Leu Ile Thr Asp Ala
                325                 330                 335

Ala Lys Asp Lys Gly Ala Ala Glu Leu Glu Lys Leu Phe Lys Ala Val
            340                 345                 350

Glu Asn Leu Ala Lys Ala Ala Lys Glu Met Leu Ala Asn Ser Val Lys
        355                 360                 365

Glu Leu
    370

<210> SEQ ID NO 37
<211> LENGTH: 1106
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1106)

<400> SEQUENCE: 37 atg gct tgt aat aat tca gga aaa gat ggg aat gca tct gca aat tct      48
Met Ala Cys Asn Asn Ser Gly Lys Asp Gly Asn Ala Ser Ala Asn Ser
  1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                 20                  25                  30 att aca gaa tct aac gca gtt gtt ctg gcc gtg aaa gaa gtt gag acc     144
Ile Thr Glu Ser Asn Ala Val Val Leu Ala Val Lys Glu Val Glu Thr
             35                  40                  45 tta ctt gca tct ata gat gaa ctt gct acc aaa gct att ggt aaa aaa     192
Leu Leu Ala Ser Ile Asp Glu Leu Ala Thr Lys Ala Ile Gly Lys Lys
         50                  55                  60 ata ggc aat aat ggt tta gag gcc aat cag agt aaa aac aca tca ttg     240
Ile Gly Asn Asn Gly Leu Glu Ala Asn Gln Ser Lys Asn Thr Ser Leu
 65                  70                  75                  80 tta tca gga gct tat gca ata tct gac cta ata gca gaa aaa tta aat     288
Leu Ser Gly Ala Tyr Ala Ile Ser Asp Leu Ile Ala Glu Lys Leu Asn
                 85                  90                  95 gta ttg aaa aat gaa gaa tta aag gaa aag att gat aca gct aag caa     336
Val Leu Lys Asn Glu Glu Leu Lys Glu Lys Ile Asp Thr Ala Lys Gln
            100                 105                 110 tgt tct aca gaa ttt act aat aaa cta aaa agt gaa cat gca gtg ctt     384
Cys Ser Thr Glu Phe Thr Asn Lys Leu Lys Ser Glu His Ala Val Leu
        115                 120                 125 ggt ctg gac aat ctt act gat gat aat gca caa aga gct att tta aaa     432
Gly Leu Asp Asn Leu Thr Asp Asp Asn Ala Gln Arg Ala Ile Leu Lys
    130                 135                 140 aaa cat gca aat aaa gat aag ggt gct gca gaa ctt gaa aag tta ttt     480
Lys His Ala Asn Lys Asp Lys Gly Ala Ala Glu Leu Glu Lys Leu Phe
145                 150                 155                 160 aaa gcg gta gaa aac tta tca aaa gca gct caa gac aca tta aaa aat     528
Lys Ala Val Glu Asn Leu Ser Lys Ala Ala Gln Asp Thr Leu Lys Asn
                165                 170                 175 gct gtt aaa gag ctt aca agt cct att gtc cat ggt aat aat tca aga     576
Ala Val Lys Glu Leu Thr Ser Pro Ile Val His Gly Asn Asn Ser Arg
            180                 185                 190
```

```
aaa gat ggg aat gca tct aca aat tct gcc gat gag tct gtt aaa ggg      624
Lys Asp Gly Asn Ala Ser Thr Asn Ser Ala Asp Glu Ser Val Lys Gly
            195                 200                 205 cct aat ctt aca gaa ata agt aaa aaa att aca gaa tct aac gca gtt      672
Pro Asn Leu Thr Glu Ile Ser Lys Lys Ile Thr Glu Ser Asn Ala Val
210                 215                 220 gtt ctg gcc gtg aaa gaa gtt gag acc tta ctt gca tct ata gat gaa      720
Val Leu Ala Val Lys Glu Val Glu Thr Leu Leu Ala Ser Ile Asp Glu
225                 230                 235                 240 ctt gct acc aaa gct att ggt aag aaa ata ggc aat aat ggt tta gag      768
Leu Ala Thr Lys Ala Ile Gly Lys Lys Ile Gly Asn Asn Gly Leu Glu
                245                 250                 255 gcc aat cag agt aaa aac aca tca ttg tta tca gga gct tat gca ata      816
Ala Asn Gln Ser Lys Asn Thr Ser Leu Leu Ser Gly Ala Tyr Ala Ile
            260                 265                 270 tct gac cta ata gca gaa aaa tta aat gta ttg aaa aat gaa gaa tta      864
Ser Asp Leu Ile Ala Glu Lys Leu Asn Val Leu Lys Asn Glu Glu Leu
        275                 280                 285 aag gaa aag att gat aca gct aag caa tgt tct aca gaa ttt act aat      912
Lys Glu Lys Ile Asp Thr Ala Lys Gln Cys Ser Thr Glu Phe Thr Asn
290                 295                 300 aaa cta aaa agt gaa cat gca gtg ctt ggt ctg gac aat ctt act gat      960
Lys Leu Lys Ser Glu His Ala Val Leu Gly Leu Asp Asn Leu Thr Asp
305                 310                 315                 320 gat aat gca caa aga gct att tta aaa aaa cat gca aat aaa gat aag     1008
Asp Asn Ala Gln Arg Ala Ile Leu Lys Lys His Ala Asn Lys Asp Lys
                325                 330                 335 ggt gct gca gaa ctt gaa aag tta ttt aaa gcg gta gaa aac tta tca     1056
Gly Ala Ala Glu Leu Glu Lys Leu Phe Lys Ala Val Glu Asn Leu Ser
            340                 345                 350 aaa gca gct caa gac aca tta aaa aat gct gtt aaa gag ctt aca agt     1104
Lys Ala Ala Gln Asp Thr Leu Lys Asn Ala Val Lys Glu Leu Thr Ser
        355                 360                 365 cc                                                                   1106
```

<210> SEQ ID NO 38
<211> LENGTH: 368
<212> TYPE: PRT
<213> ORGANISM: Artificial Sequence
<220> FEATURE:
<223> OTHER INFORMATION: OspC Chimera

<400> SEQUENCE: 38

```
Met Ala Cys Asn Asn Ser Gly Lys Asp Gly Asn Ala Ser Ala Asn Ser
 1               5                  10                  15

Ala Asp Glu Ser Val Lys Gly Pro Asn Leu Thr Glu Ile Ser Lys Lys
            20                  25                  30

```
Gly Leu Asp Asn Leu Thr Asp Asp Asn Ala Gln Arg Ala Ile Leu Lys
    130                 135                 140

Lys His Ala Asn Lys Asp Lys Gly Ala Ala Glu Leu Glu Lys Leu Phe
145                 150                 155                 160

Lys Ala Val Glu Asn Leu Ser Lys Ala Ala Gln Asp Thr Leu Lys Asn
                165                 170                 175

Ala Val Lys Glu Leu Thr Ser Pro Ile Val His Gly Asn Asn Ser Arg
            180                 185                 190

Lys Asp Gly Asn Ala Ser Thr Asn Ser Ala Asp Glu Ser Val Lys Gly
        195                 200                 205

Pro Asn Leu Thr Glu Ile Ser Lys Lys Ile Thr Glu Ser Asn Ala Val
    210                 215                 220

Val Leu Ala Val Lys Glu Val Glu Thr Leu Leu Ala Ser Ile Asp Glu
225                 230                 235                 240

Leu Ala Thr Lys Ala Ile Gly Lys Lys Ile Gly Asn Asn Gly Leu Glu
                245                 250                 255

Ala Asn Gln Ser Lys Asn Thr Ser Leu Leu Ser Gly Ala Tyr Ala Ile
            260                 265                 270

Ser Asp Leu Ile Ala Glu Lys Leu Asn Val Leu Lys Asn Glu Glu Leu
        275                 280                 285

Lys Glu Lys Ile Asp Thr Ala Lys Gln Cys Ser Thr Glu Phe Thr Asn
    290                 295                 300

Lys Leu Lys Ser Glu His Ala Val Leu Gly Leu Asp Asn Leu Thr Asp
305                 310                 315                 320

Asp Asn Ala Gln Arg Ala Ile Leu Lys Lys His Ala Asn Lys Asp Lys
                325                 330                 335

Gly Ala Ala Glu Leu Glu Lys Leu Phe Lys Ala Val Glu Asn Leu Ser
            340                 345                 350

Lys Ala Ala Gln Asp Thr Leu Lys Asn Ala Val Lys Glu Leu Thr Ser
        355                 360                 365

<210> SEQ ID NO 39
<211> LENGTH: 1107
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1107)

<400> SEQUENCE: 39 atg gct tgt aat aat tca gga aaa gat ggg aat gca tct gca aat tct      48
Met Ala Cys Asn Asn Ser Gly Lys Asp Gly Asn Ala Ser Ala Asn Ser
  1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                 20                  25                  30 att aca gaa tct aac gca gtt gtt ctg gcc gtg aaa gaa gtt gag acc     144
Ile Thr Glu Ser Asn Ala Val Val Leu Ala Val Lys Glu Val Glu Thr
             35                  40                  45 tta ctt gca tct ata gat gaa ctt gct acc aaa gct att ggt aaa aaa     192
Leu Leu Ala Ser Ile Asp Glu Leu Ala Thr Lys Ala Ile Gly Lys Lys
         50                  55                  60 ata ggc aat aat ggt tta gag gcc aat cag agt aaa aac aca tca ttg     240
Ile Gly Asn Asn Gly Leu Glu Ala Asn Gln Ser Lys Asn Thr Ser Leu
 65                  70                  75                  80
```

| | | |
|---|---|---|
| tta tca gga gct tat gca ata tct gac cta ata gca gaa aaa tta aat<br>Leu Ser Gly Ala Tyr Ala Ile Ser Asp Leu Ile Ala Glu Lys Leu Asn<br>                    85                         90                    95 | | 288 |
| gta ttg aaa aat gaa gaa tta aag gaa aag att gat aca gct aag caa<br>Val Leu Lys Asn Glu Glu Leu Lys Glu Lys Ile Asp Thr Ala Lys Gln<br>            100                       105                    110 | | 336 |
| tgt tct aca gaa ttt act aat aaa cta aaa agt gaa cat gca gtg ctt<br>Cys Ser Thr Glu Phe Thr Asn Lys Leu Lys Ser Glu His Ala Val Leu<br>            115                       120                    125 | | 384 |
| ggt ctg gac aat ctt act gat gat aat gca caa aga gct att tta aaa<br>Gly Leu Asp Asn Leu Thr Asp Asp Asn Ala Gln Arg Ala Ile Leu Lys<br>130                       135                    140 | | 432 |
| aaa cat gca aat aaa gat aag ggt gct gca gaa ctt gaa aag tta ttt<br>Lys His Ala Asn Lys Asp Lys Gly Ala Ala Glu Leu Glu Lys Leu Phe<br>145                       150                    155                    160 | | 480 |
| aaa gcg gta gaa aac tta tca aaa gca gct caa gac aca tta aaa aat<br>Lys Ala Val Glu Asn Leu Ser Lys Ala Ala Gln Asp Thr Leu Lys Asn<br>            165                       170                    175 | | 528 |
| gct gtt aaa gag ctt aca agt cct att gtc cat ggt aat aat tca ggg<br>Ala Val Lys Glu Leu Thr Ser Pro Ile Val His Gly Asn Asn Ser Gly<br>                 180                       185                    190 | | 576 |
| aaa gat ggg aat aca tct gca aat tct gct gat gag tct gtt aaa ggg<br>Lys Asp Gly Asn Thr Ser Ala Asn Ser Ala Asp Glu Ser Val Lys Gly<br>               195                       200                    205 | | 624 |
| cct aat ctt aca gaa ata agt aaa aaa att aca gaa tct aac gca gtt<br>Pro Asn Leu Thr Glu Ile Ser Lys Lys Ile Thr Glu Ser Asn Ala Val<br>210                       215                    220 | | 672 |
| gtt ctc gcc gtg aaa gaa gtt gaa act ttg ctt aca tct ata gat gag<br>Val Leu Ala Val Lys Glu Val Glu Thr Leu Leu Thr Ser Ile Asp Glu<br>225                       230                    235                    240 | | 720 |
| ctt gct aaa gct att ggt aaa aaa ata aaa aac gat gtt agt tta gat<br>Leu Ala Lys Ala Ile Gly Lys Lys Ile Lys Asn Asp Val Ser Leu Asp<br>               245                       250                    255 | | 768 |
| aat gag gca gat cac aac gga tca tta ata tca gga gca tat tta att<br>Asn Glu Ala Asp His Asn Gly Ser Leu Ile Ser Gly Ala Tyr Leu Ile<br>            260                       265                    270 | | 816 |
| tca aac tta ata aca aaa aaa ata agt gca ata aaa gat tca gga gaa<br>Ser Asn Leu Ile Thr Lys Lys Ile Ser Ala Ile Lys Asp Ser Gly Glu<br>               275                       280                    285 | | 864 |
| ttg aag gca gaa att gaa aag gct aag aaa tgt tct gaa gaa ttt act<br>Leu Lys Ala Glu Ile Glu Lys Ala Lys Lys Cys Ser Glu Glu Phe Thr<br>            290                       295                    300 | | 912 |
| gct aaa tta aaa ggt gaa cac aca gat ctt ggt aaa gaa ggc gtt act<br>Ala Lys Leu Lys Gly Glu His Thr Asp Leu Gly Lys Glu Gly Val Thr<br>305                       310                    315                    320 | | 960 |
| gat gat aat gca aaa aaa gcc att tta aaa aca aat aat gat aaa act<br>Asp Asp Asn Ala Lys Lys Ala Ile Leu Lys Thr Asn Asn Asp Lys Thr<br>                   325                       330                    335 | | 1008 |
| aag ggc gct gat gaa ctt gaa aag tta ttt gaa tca gta aaa aac ttg<br>Lys Gly Ala Asp Glu Leu Glu Lys Leu Phe Glu Ser Val Lys Asn Leu<br>            340                       345                    350 | | 1056 |
| tca aaa gca gct aaa gag atg ctt act aat tca gtt aaa gag ctt aca<br>Ser Lys Ala Ala Lys Glu Met Leu Thr Asn Ser Val Lys Glu Leu Thr<br>                 355                       360                    365 | | 1104 |
| agc<br>Ser | | 1107 |

<210> SEQ ID NO 40
<211> LENGTH: 369
<212> TYPE: PRT

-continued

<213> ORGANISM: Artificial Sequence
<220> FEATURE:
<223> OTHER INFORMATION: OspC Chimera

<400> SEQUENCE:

<211> LENGTH: 1106
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1106)

<400> SEQUENCE: 41

```
atg gct tgt aat aat tca gga aaa gat ggg aat gca tct gca aat tct      48
Met Ala Cys Asn Asn Ser Gly Lys Asp Gly Asn Ala Ser Ala Asn

```
ata tca aaa cta ata aca caa aaa tta gat gga ttg aaa aat tca gaa    864
Ile Ser Lys Leu Ile Thr Gln Lys Leu Asp Gly Leu Lys Asn Ser Glu
        275                 280                 285 aaa tta aag gaa aaa att gaa aat gct aag aaa tgt tct gaa gat ttt    912
Lys Leu Lys Glu Lys Ile Glu Asn Ala Lys Lys Cys Ser Glu Asp Phe
    290                 295                 300 act aaa aaa cta gaa gga gaa cat gcg caa ctt gga att gaa aat gtt    960
Thr Lys Lys Leu Glu Gly Glu His Ala Gln Leu Gly Ile Glu Asn Val
305                 310                 315                 320 act gat gag aat gca aaa aaa gct att tta ata aca gat gca gct aaa   1008
Thr Asp Glu Asn Ala Lys Lys Ala Ile Leu Ile Thr Asp Ala Ala Lys
            325                 330                 335 gat aag ggc gct gca gag ctt gaa aag cta ttt aaa gca gta gaa aac   1056
Asp Lys Gly Ala Ala Glu Leu Glu Lys Leu Phe Lys Ala Val Glu Asn
        340                 345                 350 ttg gca aaa gca gct aaa gag atg ctt gct aat tca gtt aaa gag ctt   1104
Leu Ala Lys Ala Ala Lys Glu Met Leu Ala Asn Ser Val Lys Glu Leu
            355                 360                 365 ac                                                                 1106

<210> SEQ ID NO 42
<211> LENGTH: 368
<212> TYPE: PRT
<213> ORGANISM: Artificial Sequence
<220> FEATURE:
<223> OTHER INFORMATION: OspC Chimera

<400> SEQUENCE: 42

Met Ala Cys Asn Asn Ser Gly Lys Asp Gly Asn Ala Ser Ala Asn Ser
 1               5                  10                  15

Ala Asp Glu Ser Val Lys Gly Pro Asn Leu Thr Glu Ile Ser Lys Lys
            20                  25                  30

Ile Thr Glu Ser Asn Ala Val Val Leu Ala Val Lys Glu Val Glu Thr
        35                  40                  45

Leu Leu Ala Ser Ile Asp Glu Leu Ala Thr Lys Ala Ile Gly Lys Lys
    50                  55                  60

Ile Gly Asn Asn Gly Leu Glu Ala Asn Gln Ser Lys Asn Thr Ser Leu
65                  70                  75                  80

Leu Ser Gly Ala Tyr Ala Ile Ser Asp Leu Ile Ala Glu Lys Leu Asn
                85                  90                  95

Val Leu Lys Asn Glu Glu Leu Lys Glu Lys Ile Asp Thr Ala Lys Gln
            100                 105                 110

Cys Ser Thr Glu Phe Thr Asn Lys Leu Lys Ser Glu His Ala Val Leu
        115                 120                 125

Gly Leu Asp Asn Leu Thr Asp Asp Asn Ala Gln Arg Ala Ile Leu Lys
    130                 135                 140

Lys His Ala Asn Lys Asp Lys Gly Ala Ala Glu Leu Glu Lys Leu Phe
145                 150                 155                 160

Lys Ala Val Glu Asn Leu Ser Lys Ala Ala Gln Asp Thr Leu Lys Asn
                165                 170                 175

Ala Val Lys Glu Leu Thr Ser Pro Ile Val His Gly Asn Asn Ser Gly
            180                 185                 190

Lys Asp Gly Asn Thr Ser Ala Asn Ser Ala Asp Glu Ser Val Lys Gly
        195                 200                 205

Pro Asn Leu Thr Glu Ile Ser Lys Lys Ile Thr Glu Ser Asn Ala Val
    210                 215                 220

Val Leu Ala Val Lys Glu Ile Glu Thr Leu Leu Ala Ser Ile Asp Glu
```

```
                225                 230                 235                 240
Leu Ala Thr Lys Ala Ile Gly Lys Lys Ile Gln Gln Asn Gly Gly Leu
                245                 250                 255

Ala Val Glu Ala Gly His Asn Gly Thr Leu Leu Ala Gly Ala Tyr Thr
                260                 265                 270

Ile Ser Lys Leu Ile Thr Gln Lys Leu Asp Gly Leu Lys Asn Ser Glu
                275                 280                 285

Lys Leu Lys Glu Lys Ile Glu Asn Ala Lys Lys Cys Ser Glu Asp Phe
            290                 295                 300

Thr Lys Lys Leu Glu Gly Glu His Ala Gln Leu Gly Ile Glu Asn Val
305                 310                 315                 320

Thr Asp Glu Asn Ala Lys Lys Ala Ile Leu Ile Thr Asp Ala Ala Lys
                325                 330                 335

Asp Lys Gly Ala Ala Glu Leu Glu Lys Leu Phe Lys Ala Val Glu Asn
                340                 345                 350

Leu Ala Lys Ala Ala Lys Glu Met Leu Ala Asn Ser Val Lys Glu Leu
                355                 360                 365

<210> SEQ ID NO 43
<211> LENGTH: 633
<212> TYPE: DNA
<213> ORGANISM: Borrelia burgdorferi
<220> FEATURE:
<221> NAME/KEY: CDS
<222> LOCATION: (1)...(633)

<400> SEQUENCE: 43 atg aaa aag aat aca tta agt gcg ata tta atg act tta ttt tta ttt       48
Met Lys Lys Asn Thr Leu Ser Ala Ile Leu Met Thr Leu Phe Leu Phe
 1               5                  10                  15 ata tct tgt aat aat tca ggg aaa gat ggg aat aca tct gca aat tct       96
Ile Ser Cys Asn Asn Ser Gly Lys Asp Gly Asn Thr Ser Ala Asn Ser
                20                  25                  30 gct gat gag tct gtt aaa ggg cct aat ctt aca gaa ata aat aaa aaa      144
Ala Asp Glu Ser Val Lys Gly Pro Asn Leu Thr Glu Ile Asn Lys Lys
            35                  40                  45 att acg gat tct aat gcg gtt tta ctt gct gtg aaa gag gtt gaa gcg      192
Ile Thr Asp Ser Asn Ala Val Leu Leu Ala Val Lys Glu Val Glu Ala
        50                  55                  60 ttg ctg tca tct ata gat gaa att gct gct aaa gct att ggt aaa aaa      240
Leu Leu Ser Ser Ile Asp Glu Ile Ala Ala Lys Ala Ile Gly Lys Lys
65                  70                  75                  80 ata cac caa aat aat ggt ttg gat acc gaa aat aat cac aat gga tca      288
Ile His Gln Asn Asn Gly Leu Asp Thr Glu Asn Asn His Asn Gly Ser
                85                  90                  95 ttg tta gcg gga gct tat gca ata tca acc cta ata aaa caa aaa tta      336
Leu Leu Ala Gly Ala Tyr Ala Ile Ser Thr Leu Ile Lys Gln Lys Leu
                100                 105                 110 gat gga ttg aaa aat gaa gga tta aag gaa aaa att gat gcg gct aag      384
Asp Gly Leu Lys Asn Glu Gly Leu Lys Glu Lys Ile Asp Ala Ala Lys
            115                 120                 125 aaa tgt tct gaa aca ttt act aat aaa tta aaa gaa aaa cac aca gat      432
Lys Cys Ser Glu Thr Phe Thr Asn Lys Leu Lys Glu Lys His Thr Asp
        130                 135                 140 ctt ggt aaa gaa ggt gtt act gat gct gat gca aaa gaa gcc att tta      480
Leu Gly Lys Glu Gly Val Thr Asp Ala Asp Ala Lys Glu Ala Ile Leu
145                 150                 155                 160 aaa gca aat ggt act aaa act aaa ggt gct gaa gaa ctt gga aaa tta      528
Lys Ala Asn Gly Thr Lys Thr Lys Gly Ala Glu Glu Leu Gly Lys Leu
```

```
                    165            170            175
ttt gaa tca gta gag gtc ttg tca aaa gca gct aaa gag atg ctt gct   576
Phe Glu Ser Val Glu Val Leu Ser Lys Ala Ala Lys Glu Met Leu Ala
            180            185            190 aat tca gtt aaa gag ctt aca agc cct gtt gtg gca gaa agt cca aaa   624
Asn Ser Val Lys Glu Leu Thr Ser Pro Val Val Ala Glu Ser Pro Lys
        195            200            205 aaa cct taa                                                        633
Lys Pro *
    210
```

<210> SEQ ID NO 44
<211> LENGTH: 210
<212> TYPE: PRT
<213> ORGANISM: Borrelia burgdorferi

<400> SEQUENCE: 44

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Asn Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Ala Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro
    210

<210> SEQ ID NO 45
<211> LENGTH: 580
<212> TYPE: DNA
<213> ORGANISM: Borrelia burgdorferi
<220> FEATURE:
<221> NAME/KEY: CDS
<222> LOCATION: (1)...(580)

<400> SEQUENCE: 45

```
atg gct tgt aat aat tca ggg aaa gat ggg aat aca tct gca aat tct   48
Met Ala Cys Asn Asn Ser Gly Lys Asp Gly Asn Thr Ser Ala Asn Ser
1               5                   10                  15
```

```
gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
         20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
     35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
 50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
             100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
         115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
     130                 135                 140 aaa gca aat ggt act aaa act aaa ggt gct gaa gaa ctt gga aaa tta     480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                 165                 170                 175 aat tca gtt aaa gag ctt aca agc cct gtt gtg gca gaa agt cca tcc     576
Asn Ser Val Lys Glu Leu Thr Ser Pro Val Val Ala Glu Ser Pro Ser
             180                 185                 190 atg g                                                               580
Met

<210> SEQ ID NO 46
<211> LENGTH: 193
<212> TYPE: PRT
<213> ORGANISM: Borrelia burgdorferi

<400> SEQUENCE: 46

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
             20                  25                  30

Ile Thr Asp Ser Asn Ala Val Leu Leu Ala Val Lys Glu Val Glu Ala
         35                  40                  45

Leu Leu Ser Ser Ile Asp Glu Ile Ala Ala Lys Ala Ile Gly Lys Lys
     50                  55                  60

Ile His Gln Asn Asn Gly Leu Asp Thr Glu Asn Asn His Asn Gly Ser
 65                  70                  75                  80

Leu Leu Ala Gly Ala Tyr Ala Ile Ser Thr Leu Ile Lys Gln Lys Leu
                 85                  90                  95

Asp Gly Leu Lys Asn Glu Gly Leu Lys Glu Lys Ile Asp Ala Ala Lys
             100                 105                 110

Lys Cys Ser Glu Thr Phe Thr Asn Lys Leu Lys Glu Lys His Thr Asp
         115                 120                 125
```

```
Leu Gly Lys Glu Gly Val Thr Asp Ala Asp Ala Lys Glu Ala Ile Leu
            130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Ser
            180                 185                 190

Met

<210> SEQ ID NO 47
<211> LENGTH: 639
<212> TYPE: DNA
<213> ORGANISM: Borrelia garinii
<220> FEATURE:
<221> NAME/KEY: CDS
<222> LOCATION: (1)...(639)

<400> SEQUENCE: 47 atg aaa aag aat aca tta agt gcg ata tta atg act tta ttt tta ttt      48
Met Lys Lys Asn Thr Leu Ser Ala Ile Leu Met Thr Leu Phe Leu Phe
 1               5                  10                  15 ata tct tgt agt aat tca ggg aaa ggt ggg gat tct gca tct act aat      96
Ile Ser Cys Ser Asn Ser Gly Lys Gly Gly Asp Ser Ala Ser Thr Asn
                20                  25                  30 cct gct gac gag tct gcg aaa ggg cct aat ctt aca gaa ata agc aaa     144
Pro Ala Asp Glu Ser Ala Lys Gly Pro Asn Leu Thr Glu Ile Ser Lys
            35                  40                  45 aaa att aca gat tct aat gca ttt gta ctt gct gtt aaa gaa gtt gag     192
Lys Ile Thr Asp Ser Asn Ala Phe Val Leu Ala Val Lys Glu Val Glu
 50                  55                  60 act ttg gtt tta tct ata gat gaa ctt gct aag aaa gct att ggt caa     240
Thr Leu Val Leu Ser Ile Asp Glu Leu Ala Lys Lys Ala Ile Gly Gln
 65                  70                  75                  80 aaa ata gac aat aat aat ggt tta gct gct tta aat aat cag aat gga     288
Lys Ile Asp Asn Asn Asn Gly Leu Ala Ala Leu Asn Asn Gln Asn Gly
                85                  90                  95 tcg ttg tta gca gga gcc tat gca ata tca acc cta ata aca gaa aaa     336
Ser Leu Leu Ala Gly Ala Tyr Ala Ile Ser Thr Leu Ile Thr Glu Lys
            100                 105                 110 ttg agt aaa ttg aaa aat tta gaa gaa tta aag aca gaa att gca aag     384
Leu Ser Lys Leu Lys Asn Leu Glu Glu Leu Lys Thr Glu Ile Ala Lys
        115                 120                 125 gct aag aaa tgt tcc gaa gaa ttt act aat aaa cta aaa agt ggt cat     432
Ala Lys Lys Cys Ser Glu Glu Phe Thr Asn Lys Leu Lys Ser Gly His
130                 135                 140 gca gat ctt ggc aaa cag gat gct acc gat gat cat gca aaa gca gct     480
Ala Asp Leu Gly Lys Gln Asp Ala Thr Asp Asp His Ala Lys Ala Ala
145                 150                 155                 160 att tta aaa aca cat gca act acc gat aaa ggt gct aaa gaa ttt aaa     528
Ile Leu Lys Thr His Ala Thr Thr Asp Lys Gly Ala Lys Glu Phe Lys
                165                 170                 175 gat tta ttt gaa tca gta gaa ggt ttg tta aaa gca gct caa gta gca     576
Asp Leu Phe Glu Ser Val Glu Gly Leu Leu Lys Ala Ala Gln Val Ala
            180                 185                 190 cta act aat tca gtt aaa gaa ctt aca agt cct gtt gta gca gaa agt     624
Leu Thr Asn Ser Val Lys Glu Leu Thr Ser Pro Val Val Ala Glu Ser
        195                 200                 205 cca aaa aaa cct taa                                                  639
Pro Lys Lys Pro *
```

<210> SEQ ID NO 48
<211> LENGTH: 212
<212> TYPE: PRT
<213> ORGANISM: Borrelia garinii

<400> SEQUENCE: 48

Met Lys Lys Asn Thr Leu Ser Ala Ile Leu Met Thr Leu Phe Leu Phe
1               5                   10                  15

Ile Ser Cys Ser Asn Ser Gly Lys Gly Gly Asp Ser Ala Ser Thr Asn
            20                  25                  30

Pro Ala Asp Glu Ser Ala Lys Gly Pro Asn Leu Thr Glu Ile Ser Lys
        35                  40                  45

Lys Ile Thr Asp Ser Asn Ala Phe Val Leu Ala Val Lys Glu Val Glu
    50                  55                  60

Thr Leu Val Leu Ser Ile Asp Glu Leu Ala Lys Lys Ala Ile Gly Gln
65                  70                  75                  80

Lys Ile Asp Asn Asn Asn Gly Leu Ala Ala Leu Asn Asn Gln Asn Gly
                85                  90                  95

Ser Leu Leu Ala Gly Ala Tyr Ala Ile Ser Thr Leu Ile Thr Glu Lys
            100                 105                 110

Leu Ser Lys Leu Lys Asn Leu Glu Glu Leu Lys Thr Glu Ile Ala Lys
        115                 120                 125

Ala Lys Lys Cys Ser Glu Glu Phe Thr Asn Lys Leu Lys Ser Gly His
    130                 135                 140

Ala Asp Leu Gly Lys Gln Asp Ala Thr Asp Asp His Ala Lys Ala Ala
145                 150                 155                 160

Ile Leu Lys Thr His Ala Thr Thr Asp Lys Gly Ala Lys Glu Phe Lys
                165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Val Ala Glu Ser
        195                 200                 205

Pro Lys Lys Pro
    210

<210> SEQ ID NO 49
<211> LENGTH: 624
<212> TYPE: DNA
<213> ORGANISM: Borrelia afzelii
<220> FEATURE:
<221> NAME/KEY: CDS
<222> LOCATION: (1)...(624)

<400> SEQUENCE: 49 atg aaa aag aat aca tta agt gcg ata tta atg act tta ttt tta ttt     48
Met Lys Lys Asn Thr Leu Ser Ala Ile Leu Met Thr Leu Phe Leu Phe
1               5                   10                  15 ata tct tgt aat aat tca ggt ggg gat tct gca tct act aat cct gat     96
Ile Ser Cys Asn Asn Ser Gly Gly Asp Ser Ala Ser Thr Asn Pro Asp
            20                  25                  30 gag tct gca aaa gga cct aat ctt acc gta ata agc aaa aaa att aca    144
Glu Ser Ala Lys Gly Pro Asn Leu Thr Val Ile Ser Lys Lys Ile Thr
        35                  40                  45 gat tct aat gca ttt tta ctg gct gtg aaa gaa gtt gag gct ttg ctt    192
Asp Ser Asn Ala Phe Leu Leu Ala Val Lys Glu Val Glu Ala Leu Leu
    50                  55                  60

```
tca tct ata gat gaa ctt tct aaa gct att ggt aaa aaa ata aaa aat     240
Ser Ser Ile Asp Glu Leu Ser Lys Ala Ile Gly Lys Lys Ile Lys Asn
 65                  70                  75                  80 gat ggt act tta gat aac gaa gca aat cga aac gaa tca ttg ata gca     288
Asp Gly Thr Leu Asp Asn Glu Ala Asn Arg Asn Glu Ser Leu Ile Ala
                 85                  90                  95 gga gct tat gaa ata tca aaa cta ata aca caa aaa tta agt gta ttg     336
Gly Ala Tyr Glu Ile Ser Lys Leu Ile Thr Gln Lys Leu Ser Val Leu
            100                 105                 110 aat tca gaa gaa tta aag aaa aaa att aaa gag gct aag gat tgt tcc     384
Asn Ser Glu Glu Leu Lys Lys Lys Ile Lys Glu Ala Lys Asp Cys Ser
        115                 120                 125 caa aaa ttt act act aag cta aaa gat agt cat gca gag ctt ggt ata     432
Gln Lys Phe Thr Thr Lys Leu Lys Asp Ser His Ala Glu Leu Gly Ile
    130                 135                 140 caa agc gtt cag gat gat aat gca aaa aaa gct att tta aaa aca cat     480
Gln Ser Val Gln Asp Asp Asn Ala Lys Lys Ala Ile Leu Lys Thr His
145                 150                 155                 160 gga act aaa gac aag ggt gct aaa gaa ctt gaa gag tta ttt aaa tca     528
Gly Thr Lys Asp Lys Gly Ala Lys Glu Leu Glu Glu Leu Phe Lys Ser
                165                 170                 175 cta gaa agc ttg tca aaa gca gcg caa gca gca tta act aat tca gtt     576
Leu Glu Ser Leu Ser Lys Ala Ala Gln Ala Ala Leu Thr Asn Ser Val
            180                 185                 190 aaa gag ctt aca aat cct gtt gtg gca gaa agt cca aaa aaa cct taa    624
Lys Glu Leu Thr Asn Pro Val Val Ala Glu Ser Pro Lys Lys Pro *
        195                 200                 205

<210> SEQ ID NO 50
<211> LENGTH: 207
<212> TYPE: PRT
<213> ORGANISM: Borrelia afzelii

<400> SEQUENCE: 50

Met Lys Lys Asn Thr Leu Ser Ala Ile Leu Met Thr Leu Phe Leu Phe
  1               5                  10                  15

Ile Ser Cys Asn Asn Ser Gly Gly Asp Ser Ala Ser Thr Asn Pro Asp
             20                  25                  30

Glu Ser Ala Lys Gly Pro Asn Leu Thr Val Ile Ser Lys Lys Ile Thr
         35                  40                  45

Asp Ser Asn Ala Phe Leu Leu Ala Val Lys Glu Val Glu Ala Leu Leu
     50                  55                  60

Ser Ser Ile Asp Glu Leu Ser Lys Ala Ile Gly Lys Lys Ile Lys Asn
 65                  70                  75                  80

Asp Gly Thr Leu Asp Asn Glu Ala Asn Arg Asn Glu Ser Leu Ile Ala
                 85                  90                  95

Gly Ala Tyr Glu Ile Ser Lys Leu Ile Thr Gln Lys Leu Ser Val Leu
            100                 105                 110

Asn Ser Glu Glu Leu Lys Lys Lys Ile Lys Glu Ala Lys Asp Cys Ser
        115                 120                 125

Gln Lys Phe Thr Thr Lys Leu Lys Asp Ser His Ala Glu Leu Gly Ile
    130                 135                 140

Gln Ser Val Gln Asp Asp Asn Ala Lys Lys Ala Ile Leu Lys Thr His
145                 150                 155                 160

Gly Thr Lys Asp Lys Gly Ala Lys Glu Leu Glu Glu Leu Phe Lys Ser
                165                 170                 175

Leu Glu Ser Leu Ser Lys Ala Ala Gln Ala Ala Leu Thr Asn Ser Val
            180                 185                 190
```

```
                    Lys Glu Leu Thr Asn Pro Val Val Ala Glu Ser Pro Lys Lys Pro
                            195                 200                 205

<210> SEQ ID NO 51
<211> LENGTH: 1680
<212> TYPE: DNA
<213> ORGANISM: ospC Chimera
<220> FEATURE:
<221> NAME/KEY: CDS
<222> LOCATION: (1)...(1680)

<400> SEQUENCE: 51 atg gct tgt aat aat tca ggg aaa gat ggg aat aca tct gca aat tct       48
Met Ala Cys Asn Asn Ser Gly Lys Asp Gly Asn Thr Ser Ala Asn Ser
1               5                  10                  15 gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
                20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
            35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
        50                  55                  60 ata cac caa aat aat ggt ttg gat acc gaa tat aat cac aat gga tca      240
Ile His Gln Asn Asn Gly Leu Asp Thr Glu Tyr Asn His Asn Gly Ser
65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
                100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
        130                 135                 140 aaa aca aat ggt act aaa act aaa ggt gct gaa gaa ctt gga aaa tta      480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca gcc      576
Asn Ser Val Lys Glu Leu Thr Ser Pro Val Val Ala Glu Ser Pro Ala
                180                 185                 190 atg ggt agt aat tca ggg aaa ggt ggg gat tct gca tct act aat cct      624
Met Gly Ser Asn Ser Gly Lys Gly Gly Asp Ser Ala Ser Thr Asn Pro
            195                 200                 205 gct gac gag tct gcg aaa ggg cct aat ctt aca gaa ata agc aaa aaa      672
Ala Asp Glu Ser Ala Lys Gly Pro Asn Leu Thr Glu Ile Ser Lys Lys
        210                 215                 220 att aca gat tct aat gca ttt gta ctt gct gtt aaa gaa gtt gag act      720
Ile Thr Asp Ser Asn Ala Phe Val Leu Ala Val Lys Glu Val Glu Thr
225                 230                 235                 240 ttg gtt tta tct ata gat gaa ctt gct aag aaa gct att ggt caa aaa      768
Leu Val Leu Ser Ile Asp Glu Leu Ala Lys Lys Ala Ile Gly Gln Lys
                245                 250                 255
```

```
ata gac aat aat aat ggt tta gct gct tta aat aat cag aat gga tcg        816
Ile Asp Asn Asn Asn Gly Leu Ala Ala Leu Asn Asn Gln Asn Gly Ser
            260                 265                 270 ttg tta gca gga gcc tat gca ata tca acc cta ata aca gaa aaa ttg        864
Leu Leu Ala Gly Ala Tyr Ala Ile Ser Thr Leu Ile Thr Glu Lys Leu
        275                 280                 285 agt aaa ttg aaa aat tta gaa gaa tta aag aca gaa att gca aag gct        912
Ser Lys Leu Lys Asn Leu Glu Glu Leu Lys Thr Glu Ile Ala Lys Ala
    290                 295                 300 aag aaa tgt tcc gaa gaa ttt act aat aaa cta aaa agt ggt cat gca        960
Lys Lys Cys Ser Glu Glu Phe Thr Asn Lys Leu Lys Ser Gly His Ala
305                 310                 315                 320 gat ctt ggc aaa cag gat gct acc gat gat cat gca aaa gca gct att       1008
Asp Leu Gly Lys Gln Asp Ala Thr Asp Asp His Ala Lys Ala Ala Ile
                325                 330                 335 tta aaa aca cat gca act acc gat aaa ggt gct aaa gaa ttt aaa gat       1056
Leu Lys Thr His Ala Thr Thr Asp Lys Gly Ala Lys Glu Phe Lys Asp
            340                 345                 350 tta ttt gaa tca gta gaa ggt ttg tta aaa gca gct caa gta gca cta       1104
Leu Phe Glu Ser Val Glu Gly Leu Leu Lys Ala Ala Gln Val Ala Leu
        355                 360                 365 act aat tca gtt aaa gaa ctt ggt cac cgt aat aat tca ggt ggg gat       1152
Thr Asn Ser Val Lys Glu Leu Gly His Arg Asn Asn Ser Gly Gly Asp
    370                 375                 380 tct gca tct act aat cct gat gag tct gca aaa gga cct aat ctt acc       1200
Ser Ala Ser Thr Asn Pro Asp Glu Ser Ala Lys Gly Pro Asn Leu Thr
385                 390                 395                 400 gta ata agc aaa aaa att aca gat tct aat gca ttt tta ctg gct gtg       1248
Val Ile Ser Lys Lys Ile Thr Asp Ser Asn Ala Phe Leu Leu Ala Val
                405                 410                 415 aaa gaa gtt gag gct ttg ctt tca tct ata gat gaa ctt tct aaa gct       1296
Lys Glu Val Glu Ala Leu Leu Ser Ser Ile Asp Glu Leu Ser Lys Ala
            420                 425                 430 att ggt aaa aaa ata aaa aat gat ggt act tta gat aac gaa gca aat       1344
Ile Gly Lys Lys Ile Lys Asn Asp Gly Thr Leu Asp Asn Glu Ala Asn
        435                 440                 445 cga aac gaa tca ttg ata gca gga gct tat gaa ata tca aaa cta ata       1392
Arg Asn Glu Ser Leu Ile Ala Gly Ala Tyr Glu Ile Ser Lys Leu Ile
    450                 455                 460 aca caa aaa tta agt gta ttg aat tca gaa gaa tta aag aaa aaa att       1440
Thr Gln Lys Leu Ser Val Leu Asn Ser Glu Glu Leu Lys Lys Lys Ile
465                 470                 475                 480 aaa gag gct aag gat tgt tcc caa aaa ttt act act aag cta aaa gat       1488
Lys Glu Ala Lys Asp Cys Ser Gln Lys Phe Thr Thr Lys Leu Lys Asp
                485                 490                 495 agt cat gca gag ctt ggt ata caa agc gtt cag gat gat aat gca aaa       1536
Ser His Ala Glu Leu Gly Ile Gln Ser Val Gln Asp Asp Asn Ala Lys
            500                 505                 510 aaa gct att tta aaa aca cat gga act aaa gac aag ggt gct aaa gaa       1584
Lys Ala Ile Leu Lys Thr His Gly Thr Lys Asp Lys Gly Ala Lys Glu
        515                 520                 525 ctt gaa gag tta ttt aaa tca cta gaa agc ttg tca aaa gca gcg caa       1632
Leu Glu Glu Leu Phe Lys Ser Leu Glu Ser Leu Ser Lys Ala Ala Gln
    530                 535                 540 gca gca tta act aat tca gtt aaa gag ctt aca aat cct gtt gtg gca       1680
Ala Ala Leu Thr Asn Ser Val Lys Glu Leu Thr Asn Pro Val Val Ala
545                 550                 555                 560

<210> SEQ ID NO 52
<211> LENGTH: 560
```

<212> TYPE: PRT
<213> ORGANISM: ospC Chimera

<400> SEQUENCE: 52

```
Met

```
Val Ile Ser Lys Lys Ile Thr Asp Ser Asn Ala Phe Leu Leu Ala Val
                405                 410                 415

Lys Glu Val Glu Ala Leu Leu Ser Ser Ile Asp Glu Leu Ser Lys Ala
            420                 425                 430

Ile Gly Lys Lys Ile Lys Asn Asp Gly Thr Leu Asp Asn Glu Ala Asn
        435                 440                 445

Arg Asn Glu Ser Leu Ile Ala Gly Ala Tyr Glu Ile Ser Lys Leu Ile
    450                 455                 460

Thr Gln Lys Leu Ser Val Leu Asn Ser Glu Glu Leu Lys Lys Lys Ile
465                 470                 475                 480

Lys Glu Ala Lys Asp Cys Ser Gln Lys Phe Thr Thr Lys Leu Lys Asp
                485                 490                 495

Ser His Ala Glu Leu Gly Ile Gln Ser Val Gln Asp Asp Asn Ala Lys
            500                 505                 510

Lys Ala Ile Leu Lys Thr His Gly Thr Lys Asp Lys Gly Ala Lys Glu
        515                 520                 525

Leu Glu Glu Leu Phe Lys Ser Leu Glu Ser Leu Ser Lys Ala Ala Gln
    530                 535                 540

Ala Ala Leu Thr Asn Ser Val Lys Glu Leu Thr Asn Pro Val Val Ala
545                 550                 555                 560

<210> SEQ ID NO 53
<211> LENGTH: 1137
<212> TYPE: DNA
<213> ORGANISM: ospC Chimera
<220> FEATURE:
<221> NAME/KEY: CDS
<222> LOCATION: (1)...(1137)

<400> SEQUENCE: 53 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1

| | | | | | | | | | | | | | | | | |
|---|---|---|---|---|---|---|---|---|---|---|---|---|---|---|---|---|
| Lys | Ala | Asn | Ala | Ala | Gly | Lys | Asp | Lys | Gly | Val | Glu | Glu | Leu | Glu | Lys | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ttg | tcc | gga | tca | tta | gaa | agc | tta | tca | aaa | gca | gct | aaa | gag | atg | ctt | 528 |
| Leu | Ser | Gly | Ser | Leu | Glu | Ser | Leu | Ser | Lys | Ala | Ala | Lys | Glu | Met | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gct | aat | tca | gtt | aaa | gag | ctt | aca | agc | cct | gtt | gtc | cat | ggt | aat | aat | 576 |
| Ala | Asn | Ser | Val | Lys | Glu | Leu | Thr | Ser | Pro | Val | Val | His | Gly | Asn | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| tca | ggt | ggg | gat | tct | gca | tct | act | aat | cct | gat | gag | tct | gca | aaa | gga | 624 |
| Ser | Gly | Gly | Asp | Ser | Ala | Ser | Thr | Asn | Pro | Asp | Glu | Ser | Ala | Lys | Gly | |
| | | | 195 | | | | | 200 | | | | | 205 | | | |

| | | | | | | | | | | | | | | | | |
|---|---|---|---|---|---|---|---|---|---|---|---|---|---|---|---|---|
| cct | aat | ctt | acc | gta | ata | agc | aaa | aaa | att | aca | gat | tct | aat | gca | ttt | 672 |
| Pro | Asn | Leu | Thr | Val | Ile | Ser | Lys | Lys | Ile | Thr | Asp | Ser | Asn | Ala | Phe | |
| 210 | | | | | 215 | | | | | 220 | | | | | | |

| | | | | | | | | | | | | | | | | |
|---|---|---|---|---|---|---|---|---|---|---|---|---|---|---|---|---|
| tta | ctg | gct | gtg | aaa | gaa | gtt | gag | gct | ttg | ctt | tca | tct | ata | gat | gaa | 720 |
| Leu | Leu | Ala | Val | Lys | Glu | Val | Glu | Ala | Leu | Leu | Ser | Ser | Ile | Asp | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctt | tct | aaa | gct | att | ggt | aaa | aaa | ata | aaa | aat | gat | ggt | act | tta | gat | 768 |
| Leu | Ser | Lys | Ala | Ile | Gly | Lys | Lys | Ile | Lys | Asn | Asp | Gly | Thr | Leu | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| aac | gaa | gca | aat | cga | aac | gaa | tca | ttg | ata | gca | gga | gct | tat | gaa | ata | 816 |
| Asn | Glu | Ala | Asn | Arg | Asn | Glu | Ser | Leu | Ile | Ala | Gly | Ala | Tyr | Glu | Ile | |
| | | | 260 | | | | | 265 | | | | | 270 | | | |

| | | | | | | | | | | | | | | | | |
|---|---|---|---|---|---|---|---|---|---|---|---|---|---|---|---|---|
| tca | aaa | cta | ata | aca | caa | aaa | tta | agt | gta | ttg | aat | tca | gaa | gaa | tta | 864 |
| Ser | Lys | Leu | Ile | Thr | Gln | Lys | Leu | Ser | Val | Leu | Asn | Ser | Glu | Glu | Leu | |
| | | | 275 | | | | | 280 | | | | | 285 | | | |

| | | | | | | | | | | | | | | | | |
|---|---|---|---|---|---|---|---|---|---|---|---|---|---|---|---|---|
| aag | aaa | aaa | att | aaa | gag | gct | aag | gat | tgt | tcc | caa | aaa | ttt | act | act | 912 |
| Lys | Lys | Lys | Ile | Lys | Glu | Ala | Lys | Asp | Cys | Ser | Gln | Lys | Phe | Thr | Thr | |
| | | 290 | | | | | 295 | | | | | 300 | | | | |

| | | | | | | | | | | | | | | | | |
|---|---|---|---|---|---|---|---|---|---|---|---|---|---|---|---|---|
| aag | cta | aaa | gat | agt | cat | gca | gag | ctt | ggt | ata | caa | agc | gtt | cag | gat | 960 |
| Lys | Leu | Lys | Asp | Ser | His | Ala | Glu | Leu | Gly | Ile | Gln | Ser | Val | Gln | Asp | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| gat | aat | gca | aaa | aaa | gct | att | tta | aaa | aca | cat | gga | act | aaa | gac | aag | 1008 |
| Asp | Asn | Ala | Lys | Lys | Ala | Ile | Leu | Lys | Thr | His | Gly | Thr | Lys | Asp | Lys | |
| | | | | 325 | | | | | 330 | | | | | 335 | | |

| | | | | | | | | | | | | | | | | |
|---|---|---|---|---|---|---|---|---|---|---|---|---|---|---|---|---|
| ggt | gct | aaa | gaa | ctt | gaa | gag | tta | ttt | aaa | tca | cta | gaa | agc | ttg | tca | 1056 |
| Gly | Ala | Lys | Glu | Leu | Glu | Glu | Leu | Phe | Lys | Ser | Leu | Glu | Ser | Leu | Ser | |
| | | | 340 | | | | | 345 | | | | | 350 | | | |

| | | | | | | | | | | | | | | | | |
|---|---|---|---|---|---|---|---|---|---|---|---|---|---|---|---|---|
| aaa | gca | gcg | caa | gca | gca | tta | act | aat | tca | gtt | aaa | gag | ctt | aca | aat | 1104 |
| Lys | Ala | Ala | Gln | Ala | Ala | Leu | Thr | Asn | Ser | Val | Lys | Glu | Leu | Thr | Asn | |
| | | | 355 | | | | | 360 | | | | | 365 | | | |

| | | | | | | | | | |
|---|---|---|---|---|---|---|---|---|---|
| cct | gtt | gtg | gca | gaa | agt | cca | aaa | aaa | cct | taa | 1137 |
| Pro | Val | Val | Ala | Glu | Ser | Pro | Lys | Lys | Pro | * | |
| 370 | | | | | 375 | | | | | | |

<210> SEQ ID NO 54
<211> LENGTH: 378
<212> TYPE: PRT
<213> ORGANISM: ospC Chimera

<400> SEQUENCE: 54

| | | | | | | | | | | | | | | |
|---|---|---|---|---|---|---|---|---|---|---|---|---|---|---|
| Met | Ala | Cys | Asn | Asn | Ser | Gly | Lys | Asp | Gly | Asn | Thr | Ser | Ala | Asn | Ser |
| 1 | | | | 5 | | | | | 10 | | | | | 15 | |

| | | | | | | | | | | | | | | |
|---|---|---|---|---|---|---|---|---|---|---|---|---|---|---|
| Ala | Asp | Glu | Ser | Val | Lys | Gly | Pro | Asn | Leu | Thr | Glu | Ile | Ser | Lys | Lys |
| | | | 20 | | | | | 25 | | | | | 30 | | |

| | | | | | | | | | | | | | | |
|---|---|---|---|---|---|---|---|---|---|---|---|---|---|---|
| Ile | Thr | Asp | Ser | Asn | Ala | Val | Leu | Leu | Ala | Val | Lys | Glu | Val | Glu | Ala |
| | | 35 | | | | | 40 | | | | | 45 | | | |

| | | | | | | | | | | | | | | |
|---|---|---|---|---|---|---|---|---|---|---|---|---|---|---|
| Leu | Leu | Ser | Ser | Ile | Asp | Glu | Leu | Ala | Lys | Ala | Ile | Gly | Lys | Lys | Ile |
| 50 | | | | | 55 | | | | | 60 | | | | | |

-continued

```
Lys Asn Asp Gly Ser Leu Asp Asn Glu Ala Asn Arg Asn Glu Ser Leu
 65                  70                  75                  80

Leu Ala Gly Ala Tyr Thr Ile Ser Thr Leu Ile Thr Gln Lys Leu Ser
                 85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Asn Asn
            180                 185                 190

Ser Gly Gly Asp Ser Ala Ser Thr Asn Pro Asp Glu Ser Ala Lys Gly
        195                 200                 205

Pro Asn Leu Thr Val Ile Ser Lys Lys Ile Thr Asp Ser Asn Ala Phe
    210                 215                 220

Leu Leu Ala Val Lys Glu Val Glu Ala Leu Leu Ser Ser Ile Asp Glu
225                 230                 235                 240

Leu Ser Lys Ala Ile Gly Lys Lys Ile Lys Asn Asp Gly Thr Leu Asp
                245                 250                 255

Asn Glu Ala Asn Arg Asn Glu Ser Leu Ile Ala Gly Ala Tyr Glu Ile
            260                 265                 270

Ser Lys Leu Ile Thr Gln Lys Leu Ser Val Leu Asn Ser Glu Glu Leu
        275                 280                 285

Lys Lys Lys Ile Lys Glu Ala Lys Asp Cys Ser Gln Lys Phe Thr Thr
    290                 295                 300

Lys Leu Lys Asp Ser His Ala Glu Leu Gly Ile Gln Ser Val Gln Asp
305                 310                 315                 320

Asp Asn Ala Lys Lys Ala Ile Leu Lys Thr His Gly Thr Lys Asp Lys
                325                 330                 335

Gly Ala Lys Glu Leu Glu Glu Leu Phe Lys Ser Leu Glu Ser Leu Ser
            340                 345                 350

Lys Ala Ala Gln Ala Ala Leu Thr Asn Ser Val Lys Glu Leu Thr Asn
        355                 360                 365

Pro Val Val Ala Glu Ser Pro Lys Lys Pro
    370                 375
```

<210> SEQ ID NO 55
<211> LENGTH: 1158
<212> TYPE: DNA
<213> ORGANISM: ospC Chimera
<220> FEATURE:
<221> NAME/KEY: CDS
<222> LOCATION: (1)...(1158)

<400> SEQUENCE: 55

```
atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30
```

```
att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
 50                  55                  60 ata cac caa aat aat ggt ttg gat acc gaa tat aat cac aat gga tca     240
Ile His Gln Asn Asn Gly Leu Asp Thr Glu Tyr Asn His Asn Gly Ser
 65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
130                 135                 140 aaa aca aat ggt act aaa act aaa ggt gct gaa gaa ctt gga aaa tta     480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa     576
Asn Ser Val Lys Glu Leu Thr Ser Pro Val Val Ala Glu Ser Pro Lys
            180                 185                 190 aaa cct ttc cat ggt aat aat tca ggt ggg gat tct gca tct act aat     624
Lys Pro Phe His Gly Asn Asn Ser Gly Gly Asp Ser Ala Ser Thr Asn
        195                 200                 205 cct gat gag tct gca aaa gga cct aat ctt acc gta ata agc aaa aaa     672
Pro Asp Glu Ser Ala Lys Gly Pro Asn Leu Thr Val Ile Ser Lys Lys
210                 215                 220 att aca gat tct aat gca ttt tta ctg gct gtg aaa gaa gtt gag gct     720
Ile Thr Asp Ser Asn Ala Phe Leu Leu Ala Val Lys Glu Val Glu Ala
225                 230                 235                 240 ttg ctt tca tct ata gat gaa ctt tct aaa gct att ggt aaa aaa ata     768
Leu Leu Ser Ser Ile Asp Glu Leu Ser Lys Ala Ile Gly Lys Lys Ile
                245                 250                 255 aaa aat gat ggt act tta gat aac gaa gca aat cga aac gaa tca ttg     816
Lys Asn Asp Gly Thr Leu Asp Asn Glu Ala Asn Arg Asn Glu Ser Leu
            260                 265                 270 ata gca gga gct tat gaa ata tca aaa cta ata aca caa aaa tta agt     864
Ile Ala Gly Ala Tyr Glu Ile Ser Lys Leu Ile Thr Gln Lys Leu Ser
        275                 280                 285 gta ttg aat tca gaa gaa tta aag aaa aaa att aaa gag gct aag gat     912
Val Leu Asn Ser Glu Glu Leu Lys Lys Lys Ile Lys Glu Ala Lys Asp
290                 295                 300 tgt tcc caa aaa ttt act act aag cta aaa gat agt cat gca gag ctt     960
Cys Ser Gln Lys Phe Thr Thr Lys Leu Lys Asp Ser His Ala Glu Leu
305                 310                 315                 320 ggt ata caa agc gtt cag gat gat aat gca aaa aaa gct att tta aaa    1008
Gly Ile Gln Ser Val Gln Asp Asp Asn Ala Lys Lys Ala Ile Leu Lys
                325                 330                 335 aca cat gga act aaa gac aag ggt gct aaa gaa ctt gaa gag tta ttt    1056
Thr His Gly Thr Lys Asp Lys Gly Ala Lys Glu Leu Glu Glu Leu Phe
            340                 345                 350
```

```
aaa tca cta gaa agc ttg tca aaa gca gcg caa gca gca tta act aat      1104
Lys Ser Leu Glu Ser Leu Ser Lys Ala Ala Gln Ala Ala Leu Thr Asn
        355                 360                 365 tca gtt aaa gag ctt aca aat cct gtt gtg gca gaa agt cca aaa aaa      1152
Ser Val Lys Glu Leu Thr Asn Pro Val Val Ala Glu Ser Pro Lys Lys
370                 375                 380 cct taa                                                              1158
Pro *
385

<210> SEQ ID NO 56
<211> LENGTH: 385
<212> TYPE: PRT
<213> ORGANISM: ospC Chimera

<400> SEQUENCE: 56
```

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
             20                  25                  30

Ile Thr Asp Ser Asn Ala Val Leu Leu Ala Val Lys Glu Val Glu Ala
         35                  40                  45

Leu Leu Ser Ser Ile Asp Glu Ile Ala Ala Lys Ala Ile Gly Lys Lys
     50                  55                  60

Ile His Gln Asn Asn Gly Leu Asp Thr Glu Tyr Asn His Asn Gly Ser
 65                  70                  75                  80

Leu Leu Ala Gly Ala Tyr Ala Ile Ser Thr Leu Ile Lys Gln Lys Leu
                 85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Phe His Gly Asn Asn Ser Gly Gly Asp Ser Ala Ser Thr Asn
        195                 200                 205

Pro Asp Glu Ser Ala Lys Gly Pro Asn Leu Thr Val Ile Ser Lys Lys
    210                 215                 220

Ile Thr Asp Ser Asn Ala Phe Leu Leu Ala Val Lys Glu Val Glu Ala
225                 230                 235                 240

Leu Leu Ser Ser Ile Asp Glu Leu Ser Lys Ala Ile Gly Lys Lys Ile
                245                 250                 255

Lys Asn Asp Gly Thr Leu Asp Asn Glu Ala Asn Arg Asn Glu Ser Leu
            260                 265                 270

Ile Ala Gly Ala Tyr Glu Ile Ser Lys Leu Ile Thr Gln Lys Leu Ser
        275                 280                 285

Val Leu Asn Ser Glu Glu Leu Lys Lys Ile Lys Glu Ala Lys Asp
    290                 295                 300

Cys Ser Gln Lys Phe Thr Thr Lys Leu Lys Asp Ser His Ala Glu Leu

```
                305                 310                 315                 320
Gly Ile Gln Ser Val Gln Asp Asp Asn Ala Lys Lys Ala Ile Leu Lys
                        325                 330                 335

Thr His Gly Thr Lys Asp Lys Gly Ala Lys Glu Leu Glu Glu Leu Phe
                    340                 345                 350

Lys Ser Leu Glu Ser Leu Ser Lys Ala Ala Gln Ala Ala Leu Thr Asn
                355                 360                 365

Ser Val Lys Glu Leu Thr Asn Pro Val Val Ala Glu Ser Pro Lys Lys
        370                 375                 380

Pro
385

<210> SEQ ID NO 57
<211> LENGTH: 1161
<212> TYPE: DNA
<213> ORGANISM: ospC Chimera
<220> FEATURE:
<221> NAME/KEY: CDS
<222> LOCATION: (1)...(1161)

<400> SEQUENCE: 57 atg tgt agt aat tca ggg aaa ggt ggg gat tct gca tct act aat cct      48
Met Cys Ser Asn Ser Gly Lys Gly Gly Asp Ser Ala Ser Thr Asn Pro
 1               5                  10                  15 gct gac gag tct gcg aaa ggg cct aat ctt aca gaa ata agc aaa aaa      96
Ala Asp Glu Ser Ala Lys Gly Pro Asn Leu Thr Glu Ile Ser Lys Lys
                20                  25                  30 att aca gat tct aat gca ttt gta ctt gct gtt aaa gaa gtt gag act     144
Ile Thr Asp Ser Asn Ala Phe Val Leu Ala Val Lys Glu Val Glu Thr
            35                  40                  45 ttg gtt tta tct ata gat gaa ctt gct aag aaa gct att ggt caa aaa     192
Leu Val Leu Ser Ile Asp Glu Leu Ala Lys Lys Ala Ile Gly Gln Lys
        50                  55                  60 ata gac aat aat aat ggt tta gct gct tta aat aat cag aat gga tcg     240
Ile Asp Asn Asn Asn Gly Leu Ala Ala Leu Asn Asn Gln Asn Gly Ser
 65                 70                  75                  80 ttg tta gca gga gcc tat gca ata tca acc cta ata aca gaa aaa ttg     288
Leu Leu Ala Gly Ala Tyr Ala Ile Ser Thr Leu Ile Thr Glu Lys Leu
                85                  90                  95 agt aaa ttg aaa aat tta gaa gaa tta aag aca gaa att gca aag gct     336
Ser Lys Leu Lys Asn Leu Glu Glu Leu Lys Thr Glu Ile Ala Lys Ala
            100                 105                 110 aag aaa tgt tcc gaa gaa ttt act aat aaa cta aaa agt ggt cat gca     384
Lys Lys Cys Ser Glu Glu Phe Thr Asn Lys Leu Lys Ser Gly His Ala
        115                 120                 125 gat ctt ggc aaa cag gat gct acc gat gat cat gca aaa gca gct att     432
Asp Leu Gly Lys Gln Asp Ala Thr Asp Asp His Ala Lys Ala Ala Ile
130                 135                 140 tta aaa aca cat gca act acc gat aaa ggt gct aaa gaa ttt aaa gat     480
Leu Lys Thr His Ala Thr Thr Asp Lys Gly Ala Lys Glu Phe Lys Asp
145                 150                 155                 160 tta ttt gaa tca gta gaa ggt ttg tta aaa gca gct caa gta gca cta     528
Leu Phe Glu Ser Val Glu Gly Leu Leu Lys Ala Ala Gln Val Ala Leu
                165                 170                 175 act aat tca gtt aaa gaa ctt aca agt cct gtt gta gca gaa agt cca     576
Thr Asn Ser Val Lys Glu Leu Thr Ser Pro Val Val Ala Glu Ser Pro
            180                 185                 190 aaa aaa cct cat atg gct aat aat tca ggt ggg gat tct gca tct act     624
Lys Lys Pro His Met Ala Asn Asn Ser Gly Gly Asp Ser Ala Ser Thr
        195                 200                 205
```

```
aat cct gat gag tct gca aaa gga cct aat ctt acc gta ata agc aaa      672
Asn Pro Asp Glu Ser Ala Lys Gly Pro Asn Leu Thr Val Ile Ser Lys
    210                 215                 220 aaa att aca gat tct aat gca ttt tta ctg gct gtg aaa gaa gtt gag      720
Lys Ile Thr Asp Ser Asn Ala Phe Leu Leu Ala Val Lys Glu Val Glu
225                 230                 235                 240 gct ttg ctt tca tct ata gat gaa ctt tct aaa gct att ggt aaa aaa      768
Ala Leu Leu Ser Ser Ile Asp Glu Leu Ser Lys Ala Ile Gly Lys Lys
                245                 250                 255 ata aaa aat gat ggt act tta gat aac gaa gca aat cga aac gaa tca      816
Ile Lys Asn Asp Gly Thr Leu Asp Asn Glu Ala Asn Arg Asn Glu Ser
            260                 265                 270 ttg ata gca gga gct tat gaa ata tca aaa cta ata aca caa aaa tta      864
Leu Ile Ala Gly Ala Tyr Glu Ile Ser Lys Leu Ile Thr Gln Lys Leu
        275                 280                 285 agt gta ttg aat tca gaa gaa tta aag aaa aaa att aaa gag gct aag      912
Ser Val Leu Asn Ser Glu Glu Leu Lys Lys Lys Ile Lys Glu Ala Lys
    290                 295                 300 gat tgt tcc caa aaa ttt act act aag cta aaa gat agt cat gca gag      960
Asp Cys Ser Gln Lys Phe Thr Thr Lys Leu Lys Asp Ser His Ala Glu
305                 310                 315                 320 ctt ggt ata caa agc gtt cag gat gat aat gca aaa aaa gct att tta     1008
Leu Gly Ile Gln Ser Val Gln Asp Asp Asn Ala Lys Lys Ala Ile Leu
                325                 330                 335 aaa aca cat gga act aaa gac aag ggt gct aaa gaa ctt gaa gag tta     1056
Lys Thr His Gly Thr Lys Asp Lys Gly Ala Lys Glu Leu Glu Glu Leu
            340                 345                 350 ttt aaa tca cta gaa agc ttg tca aaa gca gcg caa gca gca tta act     1104
Phe Lys Ser Leu Glu Ser Leu Ser Lys Ala Ala Gln Ala Ala Leu Thr
        355                 360                 365 aat tca gtt aaa gag ctt aca aat cct gtt gtg gca gaa agt cca aaa     1152
Asn Ser Val Lys Glu Leu Thr Asn Pro Val Val Ala Glu Ser Pro Lys
    370                 375                 380 aaa cct taa                                                          1161
Lys Pro  *
385

<210> SEQ ID NO 58
<211> LENGTH: 386
<212> TYPE: PRT
<213> ORGANISM: ospC Chimera

<400> SEQUENCE:

```
                115                 120                 125
Asp Leu Gly Lys Gln Asp Ala Thr Asp His Ala Lys Ala Ala Ile
    130                 135                 140

Leu Lys Thr His Ala Thr Thr Asp Lys Gly Ala Lys Glu Phe Lys Asp
145                 150                 155                 160

Leu Phe Glu Ser Val Glu Gly Leu Leu Lys Ala Ala Gln Val Ala Leu
                165                 170                 175

Thr Asn Ser Val Lys Glu Leu Thr Ser Pro Val Val Ala Glu Ser Pro
            180                 185                 190

Lys Lys Pro His Met Ala Asn Asn Ser Gly Gly Asp Ser Ala Ser Thr
        195                 200                 205

Asn Pro Asp Glu Ser Ala Lys Gly Pro Asn Leu Thr Val Ile Ser Lys
    210                 215                 220

Lys Ile Thr Asp Ser Asn Ala Phe Leu Leu Ala Val Lys Glu Val Glu
225                 230                 235                 240

Ala Leu Leu Ser Ser Ile Asp Glu Leu Ser Lys Ala Ile Gly Lys Lys
                245                 250                 255

Ile Lys Asn Asp Gly Thr Leu Asp Asn Glu Ala Asn Arg Asn Glu Ser
            260                 265                 270

Leu Ile Ala Gly Ala Tyr Glu Ile Ser Lys Leu Ile Thr Gln Lys Leu
        275                 280                 285

Ser Val Leu Asn Ser Glu Glu Leu Lys Lys Ile Lys Glu Ala Lys
    290                 295                 300

Asp Cys Ser Gln Lys Phe Thr Thr Lys Leu Lys Asp Ser His Ala Glu
305                 310                 315                 320

Leu Gly Ile Gln Ser Val Gln Asp Asp Asn Ala Lys Lys Ala Ile Leu
                325                 330                 335

Lys Thr His Gly Thr Lys Asp Lys Gly Ala Lys Glu Leu Glu Glu Leu
            340                 345                 350

Phe Lys Ser Leu Glu Ser Leu Ser Lys Ala Ala Gln Ala Ala Leu Thr
        355                 360                 365

Asn Ser Val Lys Glu Leu Thr Asn Pro Val Val Ala Glu Ser Pro Lys
    370                 375                 380

Lys Pro
385

<210> SEQ ID NO 59
<211> LENGTH: 1197
<212> TYPE: DNA
<213> ORGANISM: ospC Chimera
<220> FEATURE:
<221> NAME/KEY: CDS
<222> LOCATION: (1)...(1197)

<400> SEQUENCE: 59 atg aga tta tta ata gga ttt gct tta gcg tta gct tta ata gga tgt      48
Met Arg Leu Leu Ile Gly Phe Ala Leu Ala Leu Ala Leu Ile Gly Cys
 1               5                  10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
             20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
         35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
     50                  55                  60
```

-continued

| | | |
|---|---|---|
| ctt gct gtg aaa gag gtt gaa gcg ttg ctg tca tct ata gat gaa att<br>Leu Ala Val Lys Glu Val Glu Ala Leu Leu Ser Ser Ile Asp Glu Ile<br>65                        70                        75                      80 | 240 |
| gct gct aaa gct att ggt aaa aaa ata cac caa aat aat ggt ttg gat<br>Ala Ala Lys Ala Ile Gly Lys Lys Ile His Gln Asn Asn Gly Leu Asp<br>                        85                        90                        95 | 288 |
| acc gaa tat aat cac aat gga tca ttg tta gcg gga gct tat gca ata<br>Thr Glu Tyr Asn His Asn Gly Ser Leu Leu Ala Gly Ala Tyr Ala Ile<br>                    100                      105                      110 | 336 |
| tca acc cta ata aaa caa aaa tta gat gga ttg aaa aat gaa gga tta<br>Ser Thr Leu Ile Lys Gln Lys Leu Asp Gly Leu Lys Asn Glu Gly Leu<br>      115                      120                      125 | 384 |
| aag gaa aaa att gat gcg gct aag aaa tgt tct gaa aca ttt act aat<br>Lys Glu Lys Ile Asp Ala Ala Lys Lys Cys Ser Glu Thr Phe Thr Asn<br>130                        135                      140 | 432 |
| aaa tta aaa gaa aaa cac aca gat ctt ggt aaa gaa ggt gtt act gat<br>Lys Leu Lys Glu Lys His Thr Asp Leu Gly Lys Glu Gly Val Thr Asp<br>145                        150                      155                      160 | 480 |
| gct gat gca aaa gaa gcc att tta aaa aca aat ggt act aaa act aaa<br>Ala Asp Ala Lys Glu Ala Ile Leu Lys Thr Asn Gly Thr Lys Thr Lys<br>                    165                      170                      175 | 528 |
| ggt gct gaa gaa ctt gga aaa tta ttt gaa tca gta gag gtc ttg tca<br>Gly Ala Glu Glu Leu Gly Lys Leu Phe Glu Ser Val Glu Val Leu Ser<br>            180                      185                      190 | 576 |
| aaa gca gct aaa gag atg ctt gct aat tca gtt aaa gag ctt aca agc<br>Lys Ala Ala Lys Glu Met Leu Ala Asn Ser Val Lys Glu Leu Thr Ser<br>                    195                      200                      205 | 624 |
| cct gtt gtg gca gaa agt cca gcc atg gta aat aat tca ggg aaa gat<br>Pro Val Val Ala Glu Ser Pro Ala Met Val Asn Asn Ser Gly Lys Asp<br>210                        215                      220 | 672 |
| ggg aat aca tct gca aat tct gct gat gag tct gtt aaa ggg cct aat<br>Gly Asn Thr Ser Ala Asn Ser Ala Asp Glu Ser Val Lys Gly Pro Asn<br>225                        230                      235                      240 | 720 |
| ctt aca gaa ata agt aaa aaa att aca gaa tct aac gca gtt gtt ctc<br>Leu Thr Glu Ile Ser Lys Lys Ile Thr Glu Ser Asn Ala Val Val Leu<br>                    245                      250                      255 | 768 |
| gcc gtg aaa gaa gtt gaa act ttg ctt aca tct ata gat gag ctt gct<br>Ala Val Lys Glu Val Glu Thr Leu Leu Thr Ser Ile Asp Glu Leu Ala<br>                        260                      265                      270 | 816 |
| aaa gct att ggt aaa aaa ata aaa aac gat gtt agt tta gat aat gag<br>Lys Ala Ile Gly Lys Lys Ile Lys Asn Asp Val Ser Leu Asp Asn Glu<br>                    275                      280                      285 | 864 |
| gca gat cac aac gga tca tta ata tca gga gca tat tta att tca aac<br>Ala Asp His Asn Gly Ser Leu Ile Ser Gly Ala Tyr Leu Ile Ser Asn<br>290                        295                      300 | 912 |
| tta ata aca aaa aaa ata agt gca ata aaa gat tca gga gaa ttg aag<br>Leu Ile Thr Lys Lys Ile Ser Ala Ile Lys Asp Ser Gly Glu Leu Lys<br>305                        310                      315                      320 | 960 |
| gca gaa att gaa aag gct aag aaa tgt tct gaa gaa ttt act gct aaa<br>Ala Glu Ile Glu Lys Ala Lys Lys Cys Ser Glu Glu Phe Thr Ala Lys<br>                    325                      330                      335 | 1008 |
| tta aaa ggt gaa cac aca gat ctt ggt aaa gaa ggc gtt act gat gat<br>Leu Lys Gly Glu His Thr Asp Leu Gly Lys Glu Gly Val Thr Asp Asp<br>                        340                      345                      350 | 1056 |
| aat gca aaa aaa gcc att tta aaa aca aat aat gat aaa act aag ggc<br>Asn Ala Lys Lys Ala Ile Leu Lys Thr Asn Asn Asp Lys Thr Lys Gly<br>                    355                      360                      365 | 1104 |
| gct gat gaa ctt gaa aag tta ttt gaa tca gta aaa aac ttg tca aaa<br>Ala Asp Glu Leu Glu Lys Leu Phe Glu Ser Val Lys Asn Leu Ser Lys | 1152 |

```
            370             375             380
gca gct aaa gag atg ctt act aat tca gtt aaa gag ctt aca agc       1197
Ala Ala Lys Glu Met Leu Thr Asn Ser Val Lys Glu Leu Thr Ser
385                 390                 395
```

<210> SEQ ID NO 60
<211> LENGTH: 399
<212> TYPE: PRT
<213> ORGANISM: ospC Chimera

<400> SEQUENCE: 60

```
Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Cys Asn Asn Ser Gly Lys
             20                  25                  30

Asp Gly Asn Thr Ser Ala Asn Ser Ala Asp Glu Ser Val Lys Gly Pro
         35                  40                  45

Asn Leu Thr Glu Ile Ser Lys Lys Ile Thr Asp Ser Asn Ala Val Leu
     50                  55                  60

Leu Ala Val Lys Glu Val Glu Ala Leu Leu Ser Ser Ile Asp Glu Ile
 65                  70                  75                  80

Ala Ala Lys Ala Ile Gly Lys Lys Ile His Gln Asn Asn Gly Leu Asp
                 85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
    130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190

Lys Ala Ala Lys Glu Met Leu Ala Asn Ser Val Lys Glu Leu Thr Ser
        195                 200                 205

Pro Val Val Ala Glu Ser Pro Ala Met Val Asn Asn Ser Gly Lys Asp
    210                 215                 220

Gly Asn Thr Ser Ala Asn Ser Ala Asp Glu Ser Val Lys Gly Pro Asn
225                 230                 235                 240

Leu Thr Glu Ile Ser Lys Lys Ile Thr Glu Ser Asn Ala Val Val Leu
                245                 250                 255

Ala Val Lys Glu Val Glu Thr Leu Leu Thr Ser Ile Asp Glu Leu Ala
            260                 265                 270

Lys Ala Ile Gly Lys Lys Ile Lys Asn Asp Val Ser Leu Asp Asn Glu
        275                 280                 285

Ala Asp His Asn Gly Ser Leu Ile Ser Gly Ala Tyr Leu Ile Ser Asn
    290                 295                 300

Leu Ile Thr Lys Lys Ile Ser Ala Ile Lys Asp Ser Gly Glu Leu Lys
305                 310                 315                 320

Ala Glu Ile Glu Lys Ala Lys Lys Cys Ser Glu Glu Phe Thr Ala Lys
                325                 330                 335

Leu Lys Gly Glu His Thr Asp Leu Gly Lys Glu Gly Val Thr Asp Asp
            340                 345                 350
```

Asn Ala Lys Lys Ala Ile Leu Lys Thr Asn Asn Asp Lys Thr Lys Gly
                355                 360                 365

Ala Asp Glu Leu Glu Lys Leu Phe Glu Ser Val Lys Asn Leu Ser Lys
    370                 375                 380

Ala Ala Lys Glu Met Leu Thr Asn Ser Val Lys Glu Leu Thr Ser
385                 390                 395

<210> SEQ ID NO 61
<211> LENGTH: 1196
<212> TYPE: DNA
<213> ORGANISM: ospC Chimera
<220> FEATURE:
<221> NAME/KEY: CDS
<222> LOCATION: (1)...(1196)

<400> SEQUENCE: 61

| | |
|---|---:|
| atg aga tta tta ata gga ttt gct tta gcg tta gct tta ata gga tgt<br>Met Arg Leu Leu Ile Gly Phe Ala Leu Ala Leu Ala Leu Ile Gly Cys<br>1               5                  10                  15 | 48 |
| gca caa aaa ggt gct gag tca att gga tcc tgt aat aat tca ggg aaa<br>Ala Gln Lys Gly Ala Glu Ser Ile Gly Ser Cys Asn Asn Ser Gly Lys<br>            20                  25                  30 | 96 |
| gat ggg aat aca tct gca aat tct gct gat gag tct gtt aaa ggg cct<br>Asp Gly Asn Thr Ser Ala Asn Ser Ala Asp Glu Ser Val Lys Gly Pro<br>        35                  40                  45 | 144 |
| aat ctt aca gaa ata agt aaa aaa att acg gat tct aat gcg gtt tta<br>Asn Leu Thr Glu Ile Ser Lys Lys Ile Thr Asp Ser Asn Ala Val Leu<br>    50                  55                  60 | 192 |
| ctt gct gtg aaa gag gtt gaa gcg ttg ctg tca tct ata gat gaa att<br>Leu Ala Val Lys Glu Val Glu Ala Leu Leu Ser Ser Ile Asp Glu Ile<br>65                  70                  75                  80 | 240 |
| gct gct aaa gct att ggt aaa aaa ata cac caa aat aat ggt ttg gat<br>Ala Ala Lys Ala Ile Gly Lys Lys Ile His Gln Asn Asn Gly Leu Asp<br>                85                  90                  95 | 288 |
| acc gaa tat aat cac aat gga tca ttg tta gcg gga gct tat gca ata<br>Thr Glu Tyr Asn His Asn Gly Ser Leu Leu Ala Gly Ala Tyr Ala Ile<br>            100                 105                 110 | 336 |
| tca acc cta ata aaa caa aaa tta gat gga ttg aaa aat gaa gga tta<br>Ser Thr Leu Ile Lys Gln Lys Leu Asp Gly Leu Lys Asn Glu Gly Leu<br>        115                 120                 125 | 384 |
| aag gaa aaa att gat gcg gct aag aaa tgt tct gaa aca ttt act aat<br>Lys Glu Lys Ile Asp Ala Ala Lys Lys Cys Ser Glu Thr Phe Thr Asn<br>    130                 135                 140 | 432 |
| aaa tta aaa gaa aaa cac aca gat ctt ggt aaa gaa ggt gtt act gat<br>Lys Leu Lys Glu Lys His Thr Asp Leu Gly Lys Glu Gly Val Thr Asp<br>145                 150                 155                 160 | 480 |
| gct gat gca aaa gaa gcc att tta aaa aca aat ggt act aaa act aaa<br>Ala Asp Ala Lys Glu Ala Ile Leu Lys Thr Asn Gly Thr Lys Thr Lys<br>                165                 170                 175 | 528 |
| ggt gct gaa gaa ctt gga aaa tta ttt gaa tca gta gag gtc ttg tca<br>Gly Ala Glu Glu Leu Gly Lys Leu Phe Glu Ser Val Glu Val Leu Ser<br>            180                 185                 190 | 576 |
| aaa gca gct aaa gag atg ctt gct aat tca gtt aaa gag ctt aca agc<br>Lys Ala Ala Lys Glu Met Leu Ala Asn Ser Val Lys Glu Leu Thr Ser<br>        195                 200                 205 | 624 |
| cct gtt gtg gca gaa agt cca gcc atg gta aat aat tca gga aaa gat<br>Pro Val Val Ala Glu Ser Pro Ala Met Val Asn Asn Ser Gly Lys Asp<br>    210                 215                 220 | 672 |
| ggg aat aca tct gca aat tct gct gat gag tct gtt aaa ggg cct aat<br>Gly Asn Thr Ser Ala Asn Ser Ala Asp Glu Ser Val Lys Gly Pro Asn | 720 |

```
                    225                 230                 235                 240
ctt aca gaa ata agt aaa aaa att aca gaa tct aac gca gtt gtt ctg         768
Leu Thr Glu Ile Ser Lys Lys Ile Thr Glu Ser Asn Ala Val Val Leu
                245                 250                 255 gct gtg aaa gaa att gaa act ttg ctt gca tct ata gat gaa ctt gct         816
Ala Val Lys Glu Ile Glu Thr Leu Leu Ala Ser Ile Asp Glu Leu Ala
            260                 265                 270 act aaa gct att ggt aaa aaa ata caa caa aat ggt ggt tta gct gtc         864
Thr Lys Ala Ile Gly Lys Lys Ile Gln Gln Asn Gly Gly Leu Ala Val
            275                 280                 285 gaa gcg ggg cat aat gga aca ttg tta gca ggt gct tat aca ata tca         912
Glu Ala Gly His Asn Gly Thr Leu Leu Ala Gly Ala Tyr Thr Ile Ser
        290                 295                 300 aaa cta ata aca caa aaa tta gat gga ttg aaa aat tca gaa aaa tta         960
Lys Leu Ile Thr Gln Lys Leu Asp Gly Leu Lys Asn Ser Glu Lys Leu
305                 310                 315                 320 aag gaa aaa att gaa aat gct aag aaa tgt tct gaa gat ttt act aaa        1008
Lys Glu Lys Ile Glu Asn Ala Lys Lys Cys Ser Glu Asp Phe Thr Lys
                325                 330                 335 aaa cta gaa gga gaa cat gcg caa ctt gga att gaa aat gtt act gat        1056
Lys Leu Glu Gly Glu His Ala Gln Leu Gly Ile Glu Asn Val Thr Asp
            340                 345                 350 gag aat gca aaa aaa gct att tta ata aca gat gca gct aaa gat aag        1104
Glu Asn Ala Lys Lys Ala Ile Leu Ile Thr Asp Ala Ala Lys Asp Lys
        355                 360                 365 ggc gct gca gag ctt gaa aag cta ttt aaa gca gta gaa aac ttg gca        1152
Gly Ala Ala Glu Leu Glu Lys Leu Phe Lys Ala Val Glu Asn Leu Ala
370                 375                 380 aaa gca gct aaa gag atg ctt gct aat tca gtt aaa gag ctt ac            1196
Lys Ala Ala Lys Glu Met Leu Ala Asn Ser Val Lys Glu Leu
385                 390                 395

<210> SEQ ID NO 62
<211> LENGTH: 398
<212> TYPE: PRT
<213> ORGANISM: ospC Chimera

<400> SEQUENCE: 62

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
            20                  25                  30

Asp Gly Asn Thr Ser Ala Asn

```
Ala Asp Ala Lys Glu Ala Ile Leu Lys Thr Asn Gly Thr Lys Thr Lys
                165                 170                 175
Gly Ala Glu Glu Leu Gly Lys Leu Phe Glu Ser Val Glu Val Leu Ser
            180                 185                 190
Lys Ala Ala Lys Glu Met Leu Ala Asn Ser Val Lys Glu Leu Thr Ser
        195                 200                 205
Pro Val Ala Glu Ser Pro Ala Met Val Asn Asn Ser Gly Lys Asp
    210                 215                 220
Gly Asn Thr Ser Ala Asn Ser Ala Asp Glu Ser Val Lys Gly Pro Asn
225                 230                 235                 240
Leu Thr Glu Ile Ser Lys Lys Ile Thr Glu Ser Asn Ala Val Val Leu
                245                 250                 255
Ala Val Lys Glu Ile Glu Thr Leu Leu Ala Ser Ile Asp Glu Leu Ala
            260                 265                 270
Thr Lys Ala Ile Gly Lys Lys Ile Gln Gln Asn Gly Gly Leu Ala Val
        275                 280                 285
Glu Ala Gly His Asn Gly Thr Leu Leu Ala Gly Ala Tyr Thr Ile Ser
    290                 295                 300
Lys Leu Ile Thr Gln Lys Leu Asp Gly Leu Lys Asn Ser Glu Lys Leu
305                 310                 315                 320
Lys Glu Lys Ile Glu Asn Ala Lys Lys Cys Ser Glu Asp Phe Thr Lys
                325                 330                 335
Lys Leu Glu Gly Glu His Ala Gln Leu Gly Ile Glu Asn Val Thr Asp
            340                 345                 350
Glu Asn Ala Lys Lys Ala Ile Leu Ile Thr Asp Ala Ala Lys Asp Lys
        355                 360                 365
Gly Ala Ala Glu Leu Glu Lys Leu Phe Lys Ala Val Glu Asn Leu Ala
    370                 375                 380
Lys Ala Ala Lys Glu Met Leu Ala Asn Ser Val Lys Glu Leu
385                 390                 395

<210> SEQ ID NO 63
<211> LENGTH: 1185
<212> TYPE: DNA
<213> ORGANISM: ospC Chimera
<220> FEATURE:
<221> NAME/KEY: CDS
<222> LOCATION: (1)...(1185)

<400> SEQUENCE: 63 atg aga tta tta ata gga ttt gct tta gcg tta gct tta ata gga tgt      48
Met Arg Leu Leu Ile Gly Phe Ala Leu Ala Leu Ala Leu Ile Gly Cys
 1               5                  10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
                20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
            35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
        50                  55                  60 ctt gct gtg aaa gag gtt gaa gcg ttg ctg tca tct ata gat gag ctt     240
Leu Ala Val Lys Glu Val Glu Ala Leu Leu Ser Ser Ile Asp Glu Leu
65                  70                  75                  80 gct aaa gct att ggt aaa aaa ata aaa aac gat ggt agt tta gat aat     288
Ala Lys Ala Ile Gly Lys Lys Ile Lys Asn Asp Gly Ser Leu Asp Asn
```

-continued

```
                    85                  90                  95
gaa gca aat cgc aac gag tca ttg tta gca gga gct tat aca ata tca         336
Glu Ala Asn Arg Asn Glu Ser Leu Leu Ala Gly Ala Tyr Thr Ile Ser
            100                 105                 110 acc tta ata aca caa aaa tta agt aaa tta aac gga tca gaa ggt tta         384
Thr Leu Ile Thr Gln Lys Leu Ser Lys Leu Asn Gly Ser Glu Gly Leu
        115                 120                 125 aag gaa aag att gcc gca gct aag aaa tgc tct gaa gag ttt agt act         432
Lys Glu Lys Ile Ala Ala Ala Lys Lys Cys Ser Glu Glu Phe Ser Thr
    130                 135                 140 aaa cta aaa gat aat cat gca cag ctt ggt ata cag ggc gtt act gat         480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat         528
Glu Asn Ala Lys Lys Ala Ile Leu Lys Ala Asn Ala Ala Gly Lys Asp
                165                 170                 175 aag ggc gtt gaa gaa ctt gaa aag ttg tcc gga tca tta gaa agc tta         576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca         624
Ser Lys Ala Ala Lys Glu Met Leu Ala Asn Ser Val Lys Glu Leu Thr
        195                 200                 205 agc cct gtt gtc cat ggt aat aat tca ggg aaa gat ggg aat aca tct         672
Ser Pro Val Val His Gly Asn Asn Ser Gly Lys Asp Gly Asn Thr Ser
    210                 215                 220 gca aat tct gct gat gag tct gtt aaa ggg cct aat ctt aca gaa ata         720
Ala Asn Ser Ala Asp Glu Ser Val Lys Gly Pro Asn Leu Thr Glu Ile
225                 230                 235                 240 agt aaa aaa att aca gaa tct aac gca gtt gtt ctc gcc gtg aaa gaa         768
Ser Lys Lys Ile Thr Glu Ser Asn Ala Val Val Leu Ala Val Lys Glu
                245                 250                 255 gtt gaa act ttg ctt aca tct ata gat gag ctt gct aaa gct att ggt         816
Val Glu Thr Leu Leu Thr Ser Ile Asp Glu Leu Ala Lys Ala Ile Gly
            260                 265                 270 aaa aaa ata aaa aac gat gtt agt tta gat aat gag gca gat cac aac         864
Lys Lys Ile Lys Asn Asp Val Ser Leu Asp Asn Glu Ala Asp His Asn
        275                 280                 285 gga tca tta ata tca gga gca tat tta att tca aac tta ata aca aaa         912
Gly Ser Leu Ile Ser Gly Ala Tyr Leu Ile Ser Asn Leu Ile Thr Lys
    290                 295                 300 aaa ata agt gca ata aaa gat tca gga gaa ttg aag gca gaa att gaa         960
Lys Ile Ser Ala Ile Lys Asp Ser Gly Glu Leu Lys Ala Glu Ile Glu
305                 310                 315                 320 aag gct aag aaa tgt tct gaa gaa ttt act gct aaa tta aaa ggt gaa        1008
Lys Ala Lys Lys Cys Ser Glu Glu Phe Thr Ala Lys Leu Lys Gly Glu
                325                 330                 335 cac aca gat ctt ggt aaa gaa ggc gtt act gat gat aat gca aaa aaa        1056
His Thr Asp Leu Gly Lys Glu Gly Val Thr Asp Asp Asn Ala Lys Lys
            340                 345                 350 gcc att tta aaa aca aat aat gat aaa act aag ggc gct gat gaa ctt        1104
Ala Ile Leu Lys Thr Asn Asn Asp Lys Thr Lys Gly Ala Asp Glu Leu
        355                 360                 365 gaa aag tta ttt gaa tca gta aaa aac ttg tca aaa gca gct aaa gag        1152
Glu Lys Leu Phe Glu Ser Val Lys Asn Leu Ser Lys Ala Ala Lys Glu
    370                 375                 380 atg ctt act aat tca gtt aaa gag ctt aca agc                            1185
Met Leu Thr Asn Ser Val Lys Glu Leu Thr Ser
385                 390                 395
```

<210> SEQ ID NO 64
<211> LENGTH: 395
<212> TYPE: PRT
<213> ORGANISM: ospC Chimera

<400> SEQUENCE: 64

```
Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val

```
Met Leu Thr Asn Ser Val Lys Glu Leu Thr Ser
385                 390                 395

<210> SEQ ID NO 65
<211> LENGTH: 1184
<212> TYPE: DNA
<213> ORGANISM: ospC Chimera
<220> FEATURE:
<221> NAME/KEY: CDS
<222> LOCATION: (1)...(1184)

<400> SEQUENCE: 65 atg aga tta tta ata gga ttt gct tta gcg tta gct tta ata gga tgt      48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
                20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
            35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
        50                  55                  60 ctt gct gtg aaa gag gtt gaa gcg ttg ctg tca tct ata gat gag ctt     240
Leu Ala Val Lys Glu Val Glu Ala Leu Leu Ser Ser Ile Asp Glu Leu
65                  70                  75                  80 gct aaa gct att ggt aaa aaa ata aaa aac gat ggt agt tta gat aat     288
Ala Lys Ala Ile Gly Lys Lys Ile Lys Asn Asp Gly Ser Leu Asp Asn
                85                  90                  95 gaa gca aat cgc aac gag tca ttg tta gca gga gct tat aca ata tca     336
Glu Ala Asn Arg Asn Glu Ser Leu Leu Ala Gly Ala Tyr Thr Ile Ser
            100                 105                 110 acc tta ata aca caa aaa tta agt aaa tta aac gga tca gaa ggt tta     384
Thr Leu Ile Thr Gln Lys Leu Ser Lys Leu Asn Gly Ser Glu Gly Leu
        115                 120                 125 aag gaa aag att gcc gca gct aag aaa tgc tct gaa gag ttt agt act     432
Lys Glu Lys Ile Ala Ala Ala Lys Lys Cys Ser Glu Glu Phe Ser Thr
    130                 135                 140 aaa cta aaa gat aat cat gca cag ctt ggt ata cag ggc gtt act gat     480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat     528
Glu Asn Ala Lys Lys Ala Ile Leu Lys Ala Asn Ala Ala Gly Lys Asp
                165                 170                 175 aag ggc gtt gaa gaa ctt gaa aag ttg tcc gga tca tta gaa agc tta     576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca     624
Ser Lys Ala Ala Lys Glu Met Leu Ala Asn Ser Val Lys Glu Leu Thr
        195                 200                 205 agc cct gtt gtc cat ggt aat aat tca gga aaa gat ggg aat aca tct     672
Ser Pro Val Val His Gly Asn Asn Ser Gly Lys Asp Gly Asn Thr Ser
    210                 215                 220 gca aat tct gct gat gag tct gtt aaa ggg cct aat ctt aca gaa ata     720
Ala Asn Ser Ala Asp Glu Ser Val Lys Gly Pro Asn Leu Thr Glu Ile
225                 230                 235                 240 agt aaa aaa att aca gaa tct aac gca gtt gtt ctg gct gtg aaa gaa     768
Ser Lys Lys Ile Thr Glu Ser Asn Ala Val Val Leu Ala Val Lys Glu
                245                 250                 255 att gaa act ttg ctt gca tct ata gat gaa ctt gct act aaa gct att     816
Ile Glu Thr Leu Leu Ala Ser Ile Asp Glu Leu Ala Thr Lys Ala Ile
```

-continued

| | | | | | | | | | | | | | | |
|---|---|---|---|---|---|---|---|---|---|---|---|---|---|---|
| Ile | Glu | Thr | Leu | Leu | Ala | Ser | Ile | Asp | Glu | Leu | Ala | Thr | Lys | Ala | Ile |
| | | | 260 | | | | | 265 | | | | 270 | | | |

```
ggt aaa aaa ata caa caa aat ggt ggt tta gct gtc gaa gcg ggg cat          864
Gly Lys Lys Ile Gln Gln Asn Gly Gly Leu Ala Val Glu Ala Gly His
            275                 280                 285 aat gga aca ttg tta gca ggt gct tat aca ata tca aaa cta ata aca          912
Asn Gly Thr Leu Leu Ala Gly Ala Tyr Thr Ile Ser Lys Leu Ile Thr
    290                 295                 300 caa aaa tta gat gga ttg aaa aat tca gaa aaa tta aag gaa aaa att          960
Gln Lys Leu Asp Gly Leu Lys Asn Ser Glu Lys Leu Lys Glu Lys Ile
305                 310                 315                 320 gaa aat gct aag aaa tgt tct gaa gat ttt act aaa aaa cta gaa gga         1008
Glu Asn Ala Lys Lys Cys Ser Glu Asp Phe Thr Lys Lys Leu Glu Gly
                325                 330                 335 gaa cat gcg caa ctt gga att gaa aat gtt act gat gag aat gca aaa         1056
Glu His Ala Gln Leu Gly Ile Glu Asn Val Thr Asp Glu Asn Ala Lys
            340                 345                 350 aaa gct att tta ata aca gat gca gct aaa gat aag ggc gct gca gag         1104
Lys Ala Ile Leu Ile Thr Asp Ala Ala Lys Asp Lys Gly Ala Ala Glu
        355                 360                 365 ctt gaa aag cta ttt aaa gca gta gaa aac ttg gca aaa gca gct aaa         1152
Leu Glu Lys Leu Phe Lys Ala Val Glu Asn Leu Ala Lys Ala Ala Lys
370                 375                 380 gag atg ctt gct aat tca gtt aaa gag ctt ac                              1184
Glu Met Leu Ala Asn Ser Val Lys Glu Leu
385                 390
```

<210> SEQ ID NO 66
<211> LENGTH: 394
<212> TYPE: PRT
<213> ORGANISM: ospC Chimera

<400> S

```
Ser Lys Ala Ala Lys Glu Met Leu Ala Asn Ser Val Lys Glu Leu Thr
    195                 200                 205
Ser Pro Val Val His Gly Asn Asn Ser Gly Lys Asp Gly Asn Thr Ser
    210                 215                 220
Ala Asn Ser Ala Asp Glu Ser Val Lys Gly Pro Asn Leu Thr Glu Ile
225                 230                 235                 240
Ser Lys Lys Ile Thr Glu Ser Asn Ala Val Leu Ala Val Lys Glu
            245                 250                 255
Ile Glu Thr Leu Leu Ala Ser Ile Asp Glu Leu Ala Thr Lys Ala Ile
            260                 265                 270
Gly Lys Lys Ile Gln Gln Asn Gly Gly Leu Ala Val Glu Ala Gly His
            275                 280                 285
Asn Gly Thr Leu Leu Ala Gly Ala Tyr Thr Ile Ser Lys Leu Ile Thr
    290                 295                 300
Gln Lys Leu Asp Gly Leu Lys Asn Ser Glu Lys Leu Lys Glu Lys Ile
305                 310                 315                 320
Glu Asn Ala Lys Lys Cys Ser Glu Asp Phe Thr Lys Lys Leu Glu Gly
                325                 330                 335
Glu His Ala Gln Leu Gly Ile Glu Asn Val Thr Asp Glu Asn Ala Lys
            340                 345                 350
Lys Ala Ile Leu Ile Thr Asp Ala Ala Lys Asp Lys Gly Ala Ala Glu
            355                 360                 365
Leu Glu Lys Leu Phe Lys Ala Val Glu Asn Leu Ala Lys Ala Ala Lys
            370                 375                 380
Glu Met Leu Ala Asn Ser Val Lys Glu Leu
385                 390

<210> SEQ ID NO 67
<211> LENGTH: 1184
<212> TYPE: DNA
<213> ORGANISM: ospC Chimera
<220> FEATURE:
<221> NAME/KEY: CDS
<222> LOCATION: (1)...(1184)

<400> SEQUENCE: 67 atg aga tta tta ata gga ttt gct tta gcg tta gct tta ata gga tgt      48
Met Arg Leu Leu Ile Gly Phe Ala Leu

|  |  |  |
|---|---|---|
| Thr Leu Ile Thr Gln Lys Leu Ser Lys Leu Asn Gly Ser Glu Gly Leu<br>     115                  120                 125 |  |  |
| aag gaa aag att gcc gca gct aag aaa tgc tct gaa gag ttt agt act<br>Lys Glu Lys Ile Ala Ala Ala Lys Lys Cys Ser Glu Glu Phe Ser Thr<br>     130                 135               140 | 432 |  |
| aaa cta aaa gat aat cat gca cag ctt ggt ata cag ggc gtt act gat<br>Lys Leu Lys Asp Asn His Ala Gln Leu Gly Ile Gln Gly Val Thr Asp<br>145                 150               155               160 | 480 |  |
| gaa aat gca aaa aaa gct att tta aaa gca aat gca gcg ggt aaa gat<br>Glu Asn Ala Lys Lys Ala Ile Leu Lys Ala Asn Ala Ala Gly Lys Asp<br>                 165               170               175 | 528 |  |
| aag ggc gtt gaa gaa ctt gaa aag ttg tcc gga tca tta gaa agc tta<br>Lys Gly Val Glu Glu Leu Glu Lys Leu Ser Gly Ser Leu Glu Ser Leu<br>                180               185              190 | 576 |  |
| tca aaa gca gct aaa gag atg ctt gct aat tca gtt aaa gag ctt aca<br>Ser Lys Ala Ala Lys Glu Met Leu Ala Asn Ser Val Lys Glu Leu Thr<br>     195                 200               205 | 624 |  |
| agc cct gtt gtc cat ggt aat aat tca aga aaa gat ggg aat gca tct<br>Ser Pro Val Val His Gly Asn Asn Ser Arg Lys Asp Gly Asn Ala Ser<br>     210                 215               220 | 672 |  |
| aca aat tct gcc gat gag tct gtt aaa ggg cct aat ctt aca gaa ata<br>Thr Asn Ser Ala Asp Glu Ser Val Lys Gly Pro Asn Leu Thr Glu Ile<br>225                 230               235               240 | 720 |  |
| agt aaa aaa att aca gaa tct aac gca gtt gtt ctg gcc gtg aaa gaa<br>Ser Lys Lys Ile Thr Glu Ser Asn Ala Val Val Leu Ala Val Lys Glu<br>                 245               250               255 | 768 |  |
| gtt gag acc tta ctt gca tct ata gat gaa ctt gct acc aaa gct att<br>Val Glu Thr Leu Leu Ala Ser Ile Asp Glu Leu Ala Thr Lys Ala Ile<br>                 260               265               270 | 816 |  |
| ggt aag aaa ata ggc aat aat ggt tta gag gcc aat cag agt aaa aac<br>Gly Lys Lys Ile Gly Asn Asn Gly Leu Glu Ala Asn Gln Ser Lys Asn<br>     275                 280               285 | 864 |  |
| aca tca ttg tta tca gga gct tat gca ata tct gac cta ata gca gaa<br>Thr Ser Leu Leu Ser Gly Ala Tyr Ala Ile Ser Asp Leu Ile Ala Glu<br>     290                 295               300 | 912 |  |
| aaa tta aat gta ttg aaa aat gaa gaa tta aag gaa aag att gat aca<br>Lys Leu Asn Val Leu Lys Asn Glu Glu Leu Lys Glu Lys Ile Asp Thr<br>305                 310               315               320 | 960 |  |
| gct aag caa tgt tct aca gaa ttt act aat aaa cta aaa agt gaa cat<br>Ala Lys Gln Cys Ser Thr Glu Phe Thr Asn Lys Leu Lys Ser Glu His<br>                 325               330               335 | 1008 |  |
| gca gtg ctt ggt ctg gac aat ctt act gat gat aat gca caa aga gct<br>Ala Val Leu Gly Leu Asp Asn Leu Thr Asp Asp Asn Ala Gln Arg Ala<br>                 340               345               350 | 1056 |  |
| att tta aaa aaa cat gca aat aaa gat aag ggt gct gca gaa ctt gaa<br>Ile Leu Lys Lys His Ala Asn Lys Asp Lys Gly Ala Ala Glu Leu Glu<br>     355                 360               365 | 1104 |  |
| aag tta ttt aaa gcg gta gaa aac tta tca aaa gca gct caa gac aca<br>Lys Leu Phe Lys Ala Val Glu Asn Leu Ser Lys Ala Ala Gln Asp Thr<br>     370                 375               380 | 1152 |  |
| tta aaa aat gct gtt aaa gag ctt aca agt cc<br>Leu Lys Asn Ala Val Lys Glu Leu Thr Ser<br>385                 390 | 1184 |  |

<210> SEQ ID NO 68
<211> LENGTH: 394
<212> TYPE: PRT
<213> ORGANISM: ospC Chimera

<400> SEQUENCE:

```
Met Arg Leu Leu Ile Gly Phe Ala Leu Ala Leu Ala Leu Ile Gly Cys
 1               5                  10                  15
Ala Gln Lys Gly Ala Glu Ser Ile Gly Ser Cys Asn Asn Ser Gly Lys
             20                  25                  30
Asp Gly Asn Thr Ser Ala Asn Ser Ala Asp Glu Ser Val Lys Gly Pro
         35                  40                  45
Asn Leu Thr Glu Ile Ser Lys Lys Ile Thr Asp Ser Asn Ala Val Leu
 50                  55                  60
Leu Ala Val Lys Glu Val Glu Ala Leu Leu Ser Ser Ile Asp Glu Leu
 65                  70                  75                  80
Ala Lys Ala Ile Gly Lys Lys Ile Lys Asn Asp Gly Ser Leu Asp Asn
                 85                  90                  95
Glu Ala Asn Arg Asn Glu Ser Leu Leu Ala Gly Ala Tyr Thr Ile Ser
             100                 105                 110
Thr Leu Ile Thr Gln Lys Leu Ser Lys Leu Asn Gly Ser Glu Gly Leu
         115                 120                 125
Lys Glu Lys Ile Ala Ala Lys Lys Cys Ser Glu Glu Phe Ser Thr
130                 135                 140
Lys Leu Lys Asp Asn His Ala Gln Leu Gly Ile Gln Gly Val Thr Asp
145                 150                 155                 160
Glu Asn Ala Lys Lys Ala Ile Leu Lys Ala Asn Ala Ala Gly Lys Asp
                 165                 170                 175
Lys Gly Val Glu Glu Leu Glu Lys Leu Ser Gly Ser Leu Glu Ser Leu
             180                 185                 190
Ser Lys Ala Ala Lys Glu Met Leu Ala Asn Ser Val Lys Glu Leu Thr
         195                 200                 205
Ser Pro Val Val His Gly Asn Asn Ser Arg Lys Asp Gly Asn Ala Ser
210                 215                 220
Thr Asn Ser Ala Asp Glu Ser Val Lys Gly Pro Asn Leu Thr Glu Ile
225                 230                 235                 240
Ser Lys Lys Ile Thr Glu Ser Asn Ala Val Val Leu Ala Val Lys Glu
                 245                 250                 255
Val Glu Thr Leu Leu Ala Ser Ile Asp Glu Leu Ala Thr Lys Ala Ile
             260                 265                 270
Gly Lys Lys Ile Gly Asn Asn Gly Leu Glu Ala Asn Gln Ser Lys Asn
         275                 280                 285
Thr Ser Leu Leu Ser Gly Ala Tyr Ala Ile Ser Asp Leu Ile Ala Glu
290                 295                 300
Lys Leu Asn Val Leu Lys Asn Glu Glu Leu Lys Glu Lys Ile Asp Thr
305                 310                 315                 320
Ala Lys Gln Cys Ser Thr Glu Phe Thr Asn Lys Leu Lys Ser Glu His
                 325                 330                 335
Ala Val Leu Gly Leu Asp Asn Leu Thr Asp Asp Asn Ala Gln Arg Ala
             340                 345                 350
Ile Leu Lys Lys His Ala Asn Lys Asp Lys Gly Ala Ala Glu Leu Glu
         355                 360                 365
Lys Leu Phe Lys Ala Val Glu Asn Leu Ser Lys Ala Ala Gln Asp Thr
370                 375                 380
Leu Lys Asn Ala Val Lys Glu Leu Thr Ser
385                 390
```

<210> SEQ ID NO 69
<211> LENGTH: 1209
<212> TYPE: DNA

```
<213> ORGANISM: ospC Chimera
<220> FEATURE:
<221> NAME/KEY: CDS
<222> LOCATION: (1)...(1209)

<400> SEQUENCE: 69 atg aga tta tta ata gga ttt gct tta gcg tta gct tta ata gga tgt      48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca ggg aaa      96
Ala Gln Lys Gly Ala Glu Ser Ile Gly Ser Cys Asn Asn Ser

```
ttg ata gca gga gct tat gaa ata tca aaa cta ata aca caa aaa tta    912
Leu Ile Ala Gly Ala Tyr Glu Ile Ser Lys Leu Ile Thr Gln Lys Leu
    290                 295                 300 agt gta ttg aat tca gaa gaa tta aag aaa aaa att aaa gag gct aag    960
Ser Val Leu Asn Ser Glu Glu Leu Lys Lys Lys Ile Lys Glu Ala Lys
305                 310                 315                 320 gat tgt tcc caa aaa ttt act act aag cta aaa gat agt cat gca gag   1008
Asp Cys Ser Gln Lys Phe Thr Thr Lys Leu Lys Asp Ser His Ala Glu
                325                 330                 335 ctt ggt ata caa agc gtt cag gat gat aat gca aaa aaa gct att tta   1056
Leu Gly Ile Gln Ser Val Gln Asp Asp Asn Ala Lys Lys Ala Ile Leu
            340                 345                 350 aaa aca cat gga act aaa gac aag ggt gct aaa gaa ctt gaa gag tta   1104
Lys Thr His Gly Thr Lys Asp Lys Gly Ala Lys Glu Leu Glu Glu Leu
        355                 360                 365 ttt aaa tca cta gaa agc ttg tca aaa gca gcg caa gca gca tta act   1152
Phe Lys Ser Leu Glu Ser Leu Ser Lys Ala Ala Gln Ala Ala Leu Thr
    370                 375                 380 aat tca gtt aaa gag ctt aca aat cct gtt gtg gca gaa agt cca aaa   1200
Asn Ser Val Lys Glu Leu Thr Asn Pro Val Val Ala Glu Ser Pro Lys
385                 390                 395                 400 aaa cct taa                                                       1209
Lys Pro *

<210> SEQ ID NO 70
<211> LENGTH: 402
<212> TYPE: PRT
<213> ORGANISM: ospC Chimera

<400> SEQUENCE: 70

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

```
                  210                 215                 220
Asn Pro Asp Glu Ser Ala Lys Gly Pro Asn Leu Thr Val Ile Ser Lys
225                 230                 235                 240

Lys Ile Thr Asp Ser Asn Ala Phe Leu Leu Ala Val Lys Glu Val Glu
                245                 250                 255

Ala Leu Leu Ser Ser Ile Asp Glu Leu Ser Lys Ala Ile Gly Lys Lys
                260                 265                 270

Ile Lys Asn Asp Gly Thr Leu Asp Asn Glu Ala Asn Arg Asn Glu Ser
                275                 280                 285

Leu Ile Ala Gly Ala Tyr Glu Ile Ser Lys Leu Ile Thr Gln Lys Leu
290                 295                 300

Ser Val Leu Asn Ser Glu Glu Leu Lys Lys Ile Lys Glu Ala Lys
305                 310                 315                 320

Asp Cys Ser Gln Lys Phe Thr Thr Lys Leu Lys Asp Ser His Ala Glu
                325                 330                 335

Leu Gly Ile Gln Ser Val Gln Asp Asn Ala Lys Lys Ala Ile Leu
                340                 345                 350

Lys Thr His Gly Thr Lys Asp Lys Gly Ala Lys Glu Leu Glu Glu Leu
                355                 360                 365

Phe Lys Ser Leu Glu Ser Leu Ser Lys Ala Ala Gln Ala Ala Leu Thr
370                 375                 380

Asn Ser Val Lys Glu Leu Thr Asn Pro Val Val Ala Glu Ser Pro Lys
385                 390                 395                 400

Lys Pro

<210> SEQ ID NO 71
<211> LENGTH: 1179
<212> TYPE: DNA
<213> ORGANISM: ospC Chimera
<220> FEATURE:
<221> NAME/KEY: CDS
<222> LOCATION: (1)...(1179)

<400> SEQUENCE: 71 atg aga tta tta ata gga ttt gct tta gcg tta gct tta ata gga tgt      48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca gga aaa      96
Ala Gln Lys Gly Ala Glu Ser Ile Gly Ser Cys Asn Asn Ser Gly Lys
            20                  25                  30 gat ggg aat gca tct gca aat tct gct gat gag tct gtt aaa ggg cct     144
Asp Gly Asn Ala Ser Ala Asn Ser Ala Asp Glu Ser Val Lys Gly Pro
        35                  40                  45 aat ctt aca gaa ata agt aaa aaa att aca gaa tct aac gca gtt gtt     192
Asn Leu Thr Glu Ile Ser Lys Lys Ile Thr Glu Ser Asn Ala Val Val
    50                  55                  60 ctg gcc gtg aaa gaa gtt gag acc tta ctt gca tct ata gat gaa ctt     240
Leu Ala Val Lys Glu Val Glu Thr Leu Leu Ala Ser Ile Asp Glu Leu
65                  70                  75                  80 gct acc aaa gct att ggt aaa aaa ata ggc aat aat ggt tta gag gcc     288
Ala Thr Lys Ala Ile Gly Lys Lys Ile Gly Asn Asn Gly Leu Glu Ala
                85                  90                  95 aat cag agt aaa aac aca tca ttg tta tca gga gct tat gca ata tct     336
Asn Gln Ser Lys Asn Thr Ser Leu Leu Ser Gly Ala Tyr Ala Ile Ser
            100                 105                 110 gac cta ata gca gaa aaa tta aat gta ttg aaa aat gaa gaa tta aag     384
Asp Leu Ile Ala Glu Lys Leu Asn Val Leu Lys Asn Glu Glu Leu Lys
        115                 120                 125
```

```
gaa aag att gat aca gct aag caa tgt tct aca gaa ttt act aat aaa      432
Glu Lys Ile Asp Thr Ala Lys Gln Cys Ser Thr Glu Phe Thr Asn Lys
    130                 135                 140 cta aaa agt gaa cat gca gtg ctt ggt ctg gac aat ctt act gat gat      480
Leu Lys Ser Glu His Ala Val Leu Gly Leu Asp Asn Leu Thr Asp Asp
145                 150                 155                 160 aat gca caa aga gct att tta aaa aaa cat gca aat aaa gat aag ggt      528
Asn Ala Gln Arg Ala Ile Leu Lys Lys His Ala Asn Lys Asp Lys Gly
                165                 170                 175 gct gca gaa ctt gaa aag tta ttt aaa gcg gta gaa aac tta tca aaa      576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct      624
Ala Ala Gln Asp Thr Leu Lys Asn Ala Val Lys Glu Leu Thr Ser Pro
        195                 200                 205 att gtc cat ggt aat aat tca ggg aaa gat ggg aat aca tct gca aat      672
Ile Val His Gly Asn Asn Ser Gly Lys Asp Gly Asn Thr Ser Ala Asn
    210                 215                 220 tct gct gat gag tct gtt aaa ggg cct aat ctt aca gaa ata agt aaa      720
Ser Ala Asp Glu Ser Val Lys Gly Pro Asn Leu Thr Glu Ile Ser Lys
225                 230                 235                 240 aaa att aca gaa tct aac gca gtt gtt ctc gcc gtg aaa gaa gtt gaa      768
Lys Ile Thr Glu Ser Asn Ala Val Val Leu Ala Val Lys Glu Val Glu
                245                 250                 255 act ttg ctt aca tct ata gat gag ctt gct aaa gct att ggt aaa aaa      816
Thr Leu Leu Thr Ser Ile Asp Glu Leu Ala Lys Ala Ile Gly Lys Lys
            260                 265                 270 ata aaa aac gat gtt agt tta gat aat gag gca gat cac aac gga tca      864
Ile Lys Asn Asp Val Ser Leu Asp Asn Glu Ala Asp His Asn Gly Ser
        275                 280                 285 tta ata tca gga gca tat tta att tca aac tta ata aca aaa aaa ata      912
Leu Ile Ser Gly Ala Tyr Leu Ile Ser Asn Leu Ile Thr Lys Lys Ile
    290                 295                 300 agt gca ata aaa gat tca gga gaa ttg aag gca gaa att gaa aag gct      960
Ser Ala Ile Lys Asp Ser Gly Glu Leu Lys Ala Glu Ile Glu Lys Ala
305                 310                 315                 320 aag aaa tgt tct gaa gaa ttt act gct aaa tta aaa ggt gaa cac aca     1008
Lys Lys Cys Ser Glu Glu Phe Thr Ala Lys Leu Lys Gly Glu His Thr
                325                 330                 335 gat ctt ggt aaa gaa ggc gtt act gat gat aat gca aaa aaa gcc att     1056
Asp Leu Gly Lys Glu Gly Val Thr Asp Asp Asn Ala Lys Lys Ala Ile
            340                 345                 350 tta aaa aca aat aat gat aaa act aag ggc gct gat gaa ctt gaa aag     1104
Leu Lys Thr Asn Asn Asp Lys Thr Lys Gly Ala Asp Glu Leu Glu Lys
        355                 360                 365 tta ttt gaa tca gta aaa aac ttg tca aaa gca gct aaa gag atg ctt     1152
Leu Phe Glu Ser Val Lys Asn Leu Ser Lys Ala Ala Lys Glu Met Leu
    370                 375                 380 act aat tca gtt aaa gag ctt aca agc                                 1179
Thr Asn Ser Val Lys Glu Leu Thr Ser
385                 390

<210> SEQ ID NO 72
<211> LENGTH: 393
<212> TYPE: PRT
<213> ORGANISM: ospC Chimera

<400> SEQUENCE: 72

Met Arg Leu Leu Ile Gly Phe Ala Leu Ala Leu Ala Leu Ile Gly Cys
1               5                   10                  15
```

```
Ala Gln Lys Gly Ala Glu Ser Ile Gly Ser Cys Asn Asn Ser Gly Lys
            20                  25                  30

Asp Gly Asn Ala Ser Ala Asn Ser Ala Asp Glu Ser Val Lys Gly Pro
            35                  40                  45

Asn Leu Thr Glu Ile Ser Lys Lys Ile Thr Glu Ser Asn Ala Val Val
        50                  55                  60

Leu Ala Val Lys Glu Val Glu Thr Leu Leu Ala Ser Ile Asp Glu Leu
65                  70                  75                  80

Ala Thr Lys Ala Ile Gly Lys Lys Ile Gly Asn Asn Gly Leu Glu Ala
                85                  90                  95

Asn Gln Ser Lys Asn Thr Ser Leu Leu Ser Gly Ala Tyr Ala Ile Ser
            100                 105                 110

Asp Leu Ile Ala Glu Lys Leu Asn Val Leu Lys Asn Glu Glu Leu Lys
            115                 120                 125

Glu Lys Ile Asp Thr Ala Lys Gln Cys Ser Thr Glu Phe Thr Asn Lys
130                 135                 140

Leu Lys Ser Glu His Ala Val Leu Gly Leu Asp Asn Leu Thr Asp Asp
145                 150                 155                 160

Asn Ala Gln Arg Ala Ile Leu Lys Lys His Ala Asn Lys Asp Lys Gly
                165                 170                 175

Ala Ala Glu Leu Glu Lys Leu Phe Lys Ala Val Glu Asn Leu Ser Lys
            180                 185                 190

Ala Ala Gln Asp Thr Leu Lys Asn Ala Val Lys Glu Leu Thr Ser Pro
            195                 200                 205

Ile Val His Gly Asn Asn Ser Gly Lys Asp Gly Asn Thr Ser Ala Asn
        210                 215                 220

Ser Ala Asp Glu Ser Val Lys Gly Pro Asn Leu Thr Glu Ile Ser Lys
225                 230                 235                 240

Lys Ile Thr Glu Ser Asn Ala Val Val Leu Ala Val Lys Glu Val Glu
                245                 250                 255

Thr Leu Leu Thr Ser Ile Asp Glu Leu Ala Lys Ala Ile Gly Lys Lys
            260                 265                 270

Ile Lys Asn Asp Val Ser Leu Asp Asn Glu Ala Asp His Asn Gly Ser
        275                 280                 285

Leu Ile Ser Gly Ala Tyr Leu Ile Ser Asn Leu Ile Thr Lys Lys Ile
        290                 295                 300

Ser Ala Ile Lys Asp Ser Gly Glu Leu Lys Ala Glu Ile Glu Lys Ala
305                 310                 315                 320

Lys Lys Cys Ser Glu Glu Phe Thr Ala Lys Leu Lys Gly Glu His Thr
                325                 330                 335

Asp Leu Gly Lys Glu Gly Val Thr Asp Asn Ala Lys Lys Ala Ile
            340                 345                 350

Leu Lys Thr Asn Asn Asp Lys Thr Lys Gly Ala Asp Glu Leu Glu Lys
            355                 360                 365

Leu Phe Glu Ser Val Lys Asn Leu Ser Lys Ala Ala Lys Glu Met Leu
        370                 375                 380

Thr Asn Ser Val Lys Glu Leu Thr Ser
385                 390

<210> SEQ ID NO 73
<211> LENGTH: 1178
<212> TYPE: DNA
<213> ORGANISM: ospC Chimera
<220> FEATURE:
```

```
<221> NAME/KEY: CDS
<222> LOCATION: (1)...(1178)

<400> SEQUENCE: 73
```

| | | | | | | | | | | | | | | | | |
|---|---|---|---|---|---|---|---|---|---|---|---|---|---|---|---|---|
| atg | aga | tta | tta | ata | gga | ttt | gct | tta | gcg | tta | gct | tta | ata | gga | tgt | 48 |
| Met | Arg | Leu | Leu | Ile | Gly | Phe | Ala | Leu | Ala | Leu | Ala | Leu | Ile | Gly | Cys | |
| 1 | | | | 5 | | | | | 10 | | | | | 15 | | |
| gca | caa | aaa | ggt | gct | gag | tca | att | gga | tcc | tgt | aat | aat | tca | gga | aaa | 96 |
| Ala | Gln | Lys | Gly | Ala | Glu | Ser | Ile | Gly | Ser | Cys | Asn | Asn | Ser | Gly | Lys | |
| | | | 20 | | | | | 25 | | | | | 30 | | | |
| gat | ggg | aat | gca | tct | gca | aat | tct | gct | gat | gag | tct | gtt | aaa | ggg | cct | 144 |
| Asp | Gly | Asn | Ala | Ser | Ala | Asn | Ser | Ala | Asp | Glu | Ser | Val | Lys | Gly | Pro | |
| | | 35 | | | | | 40 | | | | | 45 | | | | |
| aat | ctt | aca | gaa | ata | agt | aaa | aaa | att | aca | gaa | tct | aac | gca | gtt | gtt | 192 |
| Asn | Leu | Thr | Glu | Ile | Ser | Lys | Lys | Ile | Thr | Glu | Ser | Asn | Ala | Val | Val | |
| | 50 | | | | | 55 | | | | | 60 | | | | | |
| ctg | gcc | gtg | aaa | gaa | gtt | gag | acc | tta | ctt | gca | tct | ata | gat | gaa | ctt | 240 |
| Leu | Ala | Val | Lys | Glu | Val | Glu | Thr | Leu | Leu | Ala | Ser | Ile | Asp | Glu | Leu | |
| 65 | | | | | 70 | | | | | 75 | | | | | 80 | |
| gct | acc | aaa | gct | att | ggt | aaa | aaa | ata | ggc | aat | aat | ggt | tta | gag | gcc | 288 |
| Ala | Thr | Lys | Ala | Ile | Gly | Lys | Lys | Ile | Gly | Asn | Asn | Gly | Leu | Glu | Ala | |
| | | | | 85 | | | | | 90 | | | | | 95 | | |
| aat | cag | agt | aaa | aac | aca | tca | ttg | tta | tca | gga | gct | tat | gca | ata | tct | 336 |
| Asn | Gln | Ser | Lys | Asn | Thr | Ser | Leu | Leu | Ser | Gly | Ala | Tyr | Ala | Ile | Ser | |
| | | | 100 | | | | | 105 | | | | | 110 | | | |
| gac | cta | ata | gca | gaa | aaa | tta | aat | gta | ttg | aaa | aat | gaa | gaa | tta | aag | 384 |
| Asp | Leu | Ile | Ala | Glu | Lys | Leu | Asn | Val | Leu | Lys | Asn | Glu | Glu | Leu | Lys | |
| | | 115 | | | | | 120 | | | | | 125 | | | | |
| gaa | aag | att | gat | aca | gct | aag | caa | tgt | tct | aca | gaa | ttt | act | aat | aaa | 432 |
| Glu | Lys | Ile | Asp | Thr | Ala | Lys | Gln | Cys | Ser | Thr | Glu | Phe | Thr | Asn | Lys | |
| | 130 | | | | | 135 | | | | | 140 | | | | | |
| cta | aaa | agt | gaa | cat | gca | gtg | ctt | ggt | ctg | gac | aat | ctt | act | gat | gat | 480 |
| Leu | Lys | Ser | Glu | His | Ala | Val | Leu | Gly | Leu | Asp | Asn | Leu | Thr | Asp | Asp | |
| 145 | | | | | 150 | | | | | 155 | | | | | 160 | |
| aat | gca | caa | aga | gct | att | tta | aaa | aaa | cat | gca | aat | aaa | gat | aag | ggt | 528 |
| Asn | Ala | Gln | Arg | Ala | Ile | Leu | Lys | Lys | His | Ala | Asn | Lys | Asp | Lys | Gly | |
| | | | | 165 | | | | | 170 | | | | | 175 | | |
| gct | gca | gaa | ctt | gaa | aag | tta | ttt | aaa | gcg | gta | gaa | aac | tta | tca | aaa | 576 |
| Ala | Ala | Glu | Leu | Glu | Lys | Leu | Phe | Lys | Ala | Val | Glu | Asn | Leu | Ser | Lys | |
| | | | 180 | | | | | 185 | | | | | 190 | | | |
| gca | gct | caa | gac | aca | tta | aaa | aat | gct | gtt | aaa | gag | ctt | aca | agt | cct | 624 |
| Ala | Ala | Gln | Asp | Thr | Leu | Lys | Asn | Ala | Val | Lys | Glu | Leu | Thr | Ser | Pro | |
| | | 195 | | | | | 200 | | | | | 205 | | | | |
| att | gtc | cat | ggt | aat | aat | tca | gga | aaa | gat | ggg | aat | aca | tct | gca | aat | 672 |
| Ile | Val | His | Gly | Asn | Asn | Ser | Gly | Lys | Asp | Gly | Asn | Thr | Ser | Ala | Asn | |
| | 210 | | | | | 215 | | | | | 220 | | | | | |
| tct | gct | gat | gag | tct | gtt | aaa | ggg | cct | aat | ctt | aca | gaa | ata | agt | aaa | 720 |
| Ser | Ala | Asp | Glu | Ser | Val | Lys | Gly | Pro | Asn | Leu | Thr | Glu | Ile | Ser | Lys | |
| 225 | | | | | 230 | | | | | 235 | | | | | 240 | |
| aaa | att | aca | gaa | tct | aac | gca | gtt | gtt | ctg | gct | gtg | aaa | gaa | att | gaa | 768 |
| Lys | Ile | Thr | Glu | Ser | Asn | Ala | Val | Val | Leu | Ala | Val | Lys | Glu | Ile | Glu | |
| | | | | 245 | | | | | 250 | | | | | 255 | | |
| act | ttg | ctt | gca | tct | ata | gat | gaa | ctt | gct | act | aaa | gct | att | ggt | aaa | 816 |
| Thr | Leu | Leu | Ala | Ser | Ile | Asp | Glu | Leu | Ala | Thr | Lys | Ala | Ile | Gly | Lys | |
| | | | | 260 | | | | | 265 | | | | | 270 | | |
| aaa | ata | caa | caa | aat | ggt | ggt | tta | gct | gtc | gaa | gcg | ggg | cat | aat | gga | 864 |
| Lys | Ile | Gln | Gln | Asn | Gly | Gly | Leu | Ala | Val | Glu | Ala | Gly | His | Asn | Gly | |
| | | 275 | | | | | 280 | | | | | 285 | | | | |
| aca | ttg | tta | gca | ggt | gct | tat | aca | ata | tca | aaa | cta | ata | aca | caa | aaa | 912 |
| Thr | Leu | Leu | Ala | Gly | Ala | Tyr | Thr | Ile | Ser | Lys | Leu | Ile | Thr | Gln | Lys | |

```
                 290                 295                 300
tta gat gga ttg aaa aat tca gaa aaa tta aag gaa aaa att gaa aat        960
Leu Asp Gly Leu Lys Asn Ser Glu Lys Leu Lys Glu Lys Ile Glu Asn
305                 310                 315                 320 gct aag aaa tgt tct gaa gat ttt act aaa aaa cta gaa gga gaa cat       1008
Ala Lys Lys Cys Ser Glu Asp Phe Thr Lys Lys Leu Glu Gly Glu His
                325                 330                 335 gcg caa ctt gga att gaa aat gtt act gat gag aat gca aaa aaa gct       1056
Ala Gln Leu Gly Ile Glu Asn Val Thr Asp Glu Asn Ala Lys Lys Ala
            340                 345                 350 att tta ata aca gat gca gct aaa gat aag ggc gct gca gag ctt gaa       1104
Ile Leu Ile Thr Asp Ala Ala Lys Asp Lys Gly Ala Ala Glu Leu Glu
        355                 360                 365 aag cta ttt aaa gca gta gaa aac ttg gca aaa gca gct aaa gag atg       1152
Lys Leu Phe Lys Ala Val Glu Asn Leu Ala Lys Ala Ala Lys Glu Met
370                 375                 380 ctt gct aat tca gtt aaa gag ctt ac                                    1178
Leu Ala Asn Ser Val Lys Glu Leu
385                 390

<210> SEQ ID NO 74
<211> LENGTH: 392
<212> TYPE: PRT
<213> ORGANISM: ospC Chimera

<400> SEQUENCE: 74

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
            20                  25                  30

Asp Gly Asn Ala Ser Ala Asn Ser Ala Asp Glu Ser Val Lys Gly Pro
        35                  40                  45

Asn Leu Thr Glu Ile Ser Lys Lys Ile Thr Glu Ser Asn Ala Val Val
    50                  55                  60

Leu Ala Val Lys Glu Val Glu Thr Leu Leu Ala Ser Ile Asp Glu Leu
65                  70                  75                  80

Ala Thr Lys Ala Ile Gly Lys Lys Ile Gly Asn Asn Gly Leu Glu Ala
                85                  90                  95

Asn Gln Ser Lys Asn Thr Ser Leu Leu Ser Gly Ala Tyr Ala Ile Ser
            100                 105                 110

Asp Leu Ile Ala Glu Lys Leu Asn Val Leu Lys Asn Glu Glu Leu Lys
        115                 120                 125

Glu Lys Ile Asp Thr Ala Lys Gln Cys Ser Thr Glu Phe Thr Asn Lys
    130                 135                 140

Leu Lys Ser Glu His Ala Val Leu Gly Leu Asp Asn Leu Thr Asp Asp
145                 150                 155                 160

Asn Ala Gln Arg Ala Ile Leu Lys Lys His Ala Asn Lys Asp Lys Gly
                165                 170                 175

Ala Ala Glu Leu Glu Lys Leu Phe Lys Ala Val Glu Asn Leu Ser Lys
            180                 185                 190

Ala Ala Gln Asp Thr Leu Lys Asn Ala Val Lys Glu Leu Thr Ser Pro
        195                 200                 205

Ile Val His Gly Asn Asn Ser Gly Lys Asp Gly Asn Thr Ser Ala Asn
    210                 215                 220

Ser Ala Asp Glu Ser Val Lys Gly Pro Asn Leu Thr Glu Ile Ser Lys
225                 230                 235                 240
```

```
Lys Ile Thr Glu Ser Asn Ala Val Val Leu Ala Val Lys Glu Ile Glu
                245                 250                 255

Thr Leu Leu Ala Ser Ile Asp Glu Leu Ala Thr Lys Ala Ile Gly Lys
            260                 265                 270

Lys Ile Gln Gln Asn Gly Gly Leu Ala Val Glu Ala Gly His Asn Gly
        275                 280                 285

Thr Leu Leu Ala Gly Ala Tyr Thr Ile Ser Lys Leu Ile Thr Gln Lys
    290                 295                 300

Leu Asp Gly Leu Lys Asn Ser Glu Lys Leu Lys Glu Lys Ile Glu Asn
305                 310                 315                 320

Ala Lys Lys Cys Ser Glu Asp Phe Thr Lys Leu Glu Gly His
                325                 330                 335

Ala Gln Leu Gly Ile Glu Asn Val Thr Asp Glu Asn Ala Lys Lys Ala
            340                 345                 350

Ile Leu Ile Thr Asp Ala Ala Lys Asp Lys Gly Ala Ala Glu Leu Glu
        355                 360                 365

Lys Leu Phe Lys Ala Val Glu Asn Leu Ala Lys Ala Ala Lys Glu Met
    370                 375                 380

Leu Ala Asn Ser Val Lys Glu Leu
385                 390

<210> SEQ ID NO 75
<211> LENGTH: 1178
<212> TYPE: DNA
<213> ORGANISM: ospC Chimera
<220> FEATURE:
<221> NAME/KEY: CDS
<222> LOCATION: (1)...(1178)

<400> SEQUENCE: 75 atg aga tta tta ata gga ttt gct tta gcg tta gct tta ata gga tgt    48
Met Arg Leu Leu Ile Gly Phe Ala Leu Ala Leu Ala Leu Ile Gly Cys
  1               5                  10                  15 gca caa aaa ggt gct gag tca att gga tcc tgt aat aat tca gga aaa    96
Ala Gln Lys Gly Ala Glu Ser Ile Gly Ser Cys Asn Asn Ser Gly Lys
             20                  25                  30 gat ggg aat gca tct gca aat tct gct gat gag tct gtt aaa ggg cct   144
Asp Gly Asn Ala Ser Ala Asn Ser Ala Asp Glu Ser Val Lys Gly Pro
         35                  40                  45 aat ctt aca gaa ata agt aaa aaa att aca gaa tct aac gca gtt gtt   192
Asn Leu Thr Glu Ile Ser Lys Lys Ile Thr Glu Ser Asn Ala Val Val
     50                  55                  60 ctg gcc gtg aaa gaa gtt gag acc tta ctt gca tct ata gat gaa ctt   240
Leu Ala Val Lys Glu Val Glu Thr Leu Leu Ala Ser Ile Asp Glu Leu
 65                  70                  75                  80 gct acc aaa gct att ggt aaa aaa ata ggc aat aat ggt tta gag gcc   288
Ala Thr Lys Ala Ile Gly Lys Lys Ile Gly Asn Asn Gly Leu Glu Ala
                 85                  90                  95 aat cag agt aaa aac aca tca ttg tta tca gga gct tat gca ata tct   336
Asn Gln Ser Lys Asn Thr Ser Leu Leu Ser Gly Ala Tyr Ala Ile Ser
            100                 105                 110 gac cta ata gca gaa aaa tta aat gta ttg aaa aat gaa gaa tta aag   384
Asp Leu Ile Ala Glu Lys Leu Asn Val Leu Lys Asn Glu Glu Leu Lys
        115                 120                 125 gaa aag att gat aca gct aag caa tgt tct aca gaa ttt act aat aaa   432
Glu Lys Ile Asp Thr Ala Lys Gln Cys Ser Thr Glu Phe Thr Asn Lys
    130                 135                 140 cta aaa agt gaa cat gca gtg ctt ggt ctg gac aat ctt act gat gat   480
Leu Lys Ser Glu His Ala Val Leu Gly Leu Asp Asn Leu Thr Asp Asp
```

```
                145                 150                 155                 160
aat gca caa aga gct att tta aaa aaa cat gca aat aaa gat aag ggt      528
Asn Ala Gln Arg Ala Ile Leu Lys Lys His Ala Asn Lys Asp Lys Gly
                165                 170                 175 gct gca gaa ctt gaa aag tta ttt aaa gcg gta gaa aac tta tca aaa      576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct      624
Ala Ala Gln Asp Thr Leu Lys Asn Ala Val Lys Glu Leu Thr Ser Pro
        195                 200                 205 att gtc cat ggt aat aat tca aga aaa gat ggg aat gca tct aca aat      672
Ile Val His Gly Asn Asn Ser Arg Lys Asp Gly Asn Ala Ser Thr Asn
    210                 215                 220 tct gcc gat gag tct gtt aaa ggg cct aat ctt aca gaa ata agt aaa      720
Ser Ala Asp Glu Ser Val Lys Gly Pro Asn Leu Thr Glu Ile Ser Lys
225                 230                 235                 240 aaa att aca gaa tct aac gca gtt gtt ctg gcc gtg aaa gaa gtt gag      768
Lys Ile Thr Glu Ser Asn Ala Val Val Leu Ala Val Lys Glu Val Glu
                245                 250                 255 acc tta ctt gca tct ata gat gaa ctt gct acc aaa gct att ggt aag      816
Thr Leu Leu Ala Ser Ile Asp Glu Leu Ala Thr Lys Ala Ile Gly Lys
            260                 265                 270 aaa ata ggc aat aat ggt tta gag gcc aat cag agt aaa aac aca tca      864
Lys Ile Gly Asn Asn Gly Leu Glu Ala Asn Gln Ser Lys Asn Thr Ser
        275                 280                 285 ttg tta tca gga gct tat gca ata tct gac cta ata gca gaa aaa tta      912
Leu Leu Ser Gly Ala Tyr Ala Ile Ser Asp Leu Ile Ala Glu Lys Leu
    290                 295                 300 aat gta ttg aaa aat gaa gaa tta aag gaa aag att gat aca gct aag      960
Asn Val Leu Lys Asn Glu Glu Leu Lys Glu Lys Ile Asp Thr Ala Lys
305                 310                 315                 320 caa tgt tct aca gaa ttt act aat aaa cta aaa agt gaa cat gca gtg     1008
Gln Cys Ser Thr Glu Phe Thr Asn Lys Leu Lys Ser Glu His Ala Val
                325                 330                 335 ctt ggt ctg gac aat ctt act gat gat aat gca caa aga gct att tta     1056
Leu Gly Leu Asp Asn Leu Thr Asp Asp Asn Ala Gln Arg Ala Ile Leu
            340                 345                 350 aaa aaa cat gca aat aaa gat aag ggt gct gca gaa ctt gaa aag tta     1104
Lys Lys His Ala Asn Lys Asp Lys Gly Ala Ala Glu Leu Glu Lys Leu
        355                 360                 365 ttt aaa gcg gta gaa aac tta tca aaa gca gct caa gac aca tta aaa     1152
Phe Lys Ala Val Glu Asn Leu Ser Lys Ala Ala Gln Asp Thr Leu Lys
    370                 375                 380 aat gct gtt aaa gag ctt aca agt cc                                  1178
Asn Ala Val Lys Glu Leu Thr Ser
385                 390

<210> SEQ ID NO 76
<211> LENGTH: 392
<212> TYPE: PRT
<213> ORGANISM: ospC Chimera

<400> SEQUENCE: 76

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
                20                  25                  30

Asp Gly Asn Ala Ser Ala Asn Ser Ala Asp Glu Ser Val Lys Gly Pro
            35                  40                  45
```

```
Asn Leu Thr Glu Ile Ser Lys Lys Ile Thr Glu Ser Asn Ala Val Val
 50                  55                  60

Leu Ala Val Lys Glu Val Glu Thr Leu Leu Ala Ser Ile Asp Glu Leu
 65                  70                  75                  80

Ala Thr Lys Ala Ile Gly Lys Lys Ile Gly Asn Asn Gly Leu Glu Ala
                 85                  90                  95

Asn Gln Ser Lys Asn Thr Ser Leu Leu Ser Gly Ala Tyr Ala Ile Ser
            100                 105                 110

Asp Leu Ile Ala Glu Lys Leu Asn Val Leu Lys Asn Glu Glu Leu Lys
        115                 120                 125

Glu Lys Ile Asp Thr Ala Lys Gln Cys Ser Thr Glu Phe Thr Asn Lys
    130                 135                 140

Leu Lys Ser Glu His Ala Val Leu Gly Leu Asp Asn Leu Thr Asp Asp
145                 150                 155                 160

Asn Ala Gln Arg Ala Ile Leu Lys Lys His Ala Asn Lys Asp Lys Gly
                165                 170                 175

Ala Ala Glu Leu Glu Lys Leu Phe Lys Ala Val Glu Asn Leu Ser Lys
            180                 185                 190

Ala Ala Gln Asp Thr Leu Lys Asn Ala Val Lys Glu Leu Thr Ser Pro
        195                 200                 205

Ile Val His Gly Asn Asn Ser Arg Lys Asp Gly Asn Ala Ser Thr Asn
    210                 215                 220

Ser Ala Asp Glu Ser Val Lys Gly Pro Asn Leu Thr Glu Ile Ser Lys
225                 230                 235                 240

Lys Ile Thr Glu Ser Asn Ala Val Val Leu Ala Val Lys Glu Val Glu
                245                 250                 255

Thr Leu Leu Ala Ser Ile Asp Glu Leu Ala Thr Lys Ala Ile Gly Lys
            260                 265                 270

Lys Ile Gly Asn Asn Gly Leu Glu Ala Asn Gln Ser Lys Asn Thr Ser
        275                 280                 285

Leu Leu Ser Gly Ala Tyr Ala Ile Ser Asp Leu Ile Ala Glu Lys Leu
    290                 295                 300

Asn Val Leu Lys Asn Glu Glu Leu Lys Glu Lys Ile Asp Thr Ala Lys
305                 310                 315                 320

Gln Cys Ser Thr Glu Phe Thr Asn Lys Leu Lys Ser Glu His Ala Val
                325                 330                 335

Leu Gly Leu Asp Asn Leu Thr Asp Asp Asn Ala Gln Arg Ala Ile Leu
            340                 345                 350

Lys Lys His Ala Asn Lys Asp Lys Gly Ala Ala Glu Leu Glu Lys Leu
        355                 360                 365

Phe Lys Ala Val Glu Asn Leu Ser Lys Ala Ala Gln Asp Thr Leu Lys
    370                 375                 380

Asn Ala Val Lys Glu Leu Thr Ser
385                 390

<210> SEQ ID NO 77
<211> LENGTH: 1230
<212> TYPE: DNA
<213> ORGANISM: ospC Chimera
<220> FEATURE:
<221> NAME/KEY: CDS
<222> LOCATION: (1)...(1230)

<400> SEQUENCE: 77 atg aga tta tta ata gga ttt gct tta gcg tta gct tta ata gga tgt    48
Met Arg Leu Leu Ile Gly Phe Ala Leu Ala Leu Ala Leu Ile Gly Cys
```

```
                1               5                  10                  15
        gca caa aaa ggt gct gag tca att gga tcc tgt aat aat tca ggg aaa        96
        Ala Gln Lys Gly Ala Glu Ser Ile Gly Ser Cys Asn Asn Ser Gly Lys
                         20                  25                  30 gat ggg aat aca tct gca aat tct gct gat gag tct gtt aaa ggg cct       144
        Asp Gly Asn Thr Ser Ala Asn Ser Ala Asp Glu Ser Val Lys Gly Pro
                35                  40                  45 aat ctt aca gaa ata agt aaa aaa att acg gat tct aat gcg gtt tta       192
        Asn Leu Thr Glu Ile Ser Lys Lys Ile Thr Asp Ser Asn Ala Val Leu
             50                  55                  60 ctt gct gtg aaa gag gtt gaa gcg ttg ctg tca tct ata gat gaa att       240
        Leu Ala Val Lys Glu Val Glu Ala Leu Leu Ser Ser Ile Asp Glu Ile
        65                   70                  75                  80 gct gct aaa gct att ggt aaa aaa ata cac caa aat aat ggt ttg gat       288
        Ala Ala Lys Ala Ile Gly Lys Lys Ile His Gln Asn Asn Gly Leu Asp
                         85                  90                  95 acc gaa tat aat cac aat gga tca ttg tta gcg gga gct tat gca ata       336
        Thr Glu Tyr Asn His Asn Gly Ser Leu Leu Ala Gly Ala Tyr Ala Ile
                100                 105                 110 tca acc cta ata aaa caa aaa tta gat gga ttg aaa aat gaa gga tta       384
        Ser Thr Leu Ile Lys Gln Lys Leu Asp Gly Leu Lys Asn Glu Gly Leu
             115                 120                 125 aag gaa aaa att gat gcg gct aag aaa tgt tct gaa aca ttt act aat       432
        Lys Glu Lys Ile Asp Ala Ala Lys Lys Cys Ser Glu Thr Phe Thr Asn
        130                 135                 140 aaa tta aaa gaa aaa cac aca gat ctt ggt aaa gaa ggt gtt act gat       480
        Lys Leu Lys Glu Lys His Thr Asp Leu Gly Lys Glu Gly Val Thr Asp
        145                 150                 155                 160 gct gat gca aaa gaa gcc att tta aaa aca aat ggt act aaa act aaa       528
        Ala Asp Ala Lys Glu Ala Ile Leu Lys Thr Asn Gly Thr Lys Thr Lys
                         165                 170                 175 ggt gct gaa gaa ctt gga aaa tta ttt gaa tca gta gag gtc ttg tca       576
        Gly Ala Glu Glu Leu Gly Lys Leu Phe Glu Ser Val Glu Val Leu Ser
                180                 185                 190 aaa gca gct aaa gag atg ctt gct aat tca gtt aaa gag ctt aca agc       624
        Lys Ala Ala Lys Glu Met Leu Ala Asn Ser Val Lys Glu Leu Thr Ser
             195                 200                 205 cct gtt gtg gca gaa agt cca aaa aaa cct ttc cat ggt aat aat tca       672
        Pro Val Val Ala Glu Ser Pro Lys Lys Pro Phe His Gly Asn Asn Ser
        210                 215                 220 ggt ggg gat tct gca tct act aat cct gat gag tct gca aaa gga cct       720
        Gly Gly Asp Ser Ala Ser Thr Asn Pro Asp Glu Ser Ala Lys Gly Pro
        225                 230                 235                 240 aat ctt acc gta ata agc aaa aaa att aca gat tct aat gca ttt tta       768
        Asn Leu Thr Val Ile Ser Lys Lys Ile Thr Asp Ser Asn Ala Phe Leu
                         245                 250                 255 ctg gct gtg aaa gaa gtt gag gct ttg ctt tca tct ata gat gaa ctt       816
        Leu Ala Val Lys Glu Val Glu Ala Leu Leu Ser Ser Ile Asp Glu Leu
                260                 265                 270 tct aaa gct att ggt aaa aaa ata aaa aat gat ggt act tta gat aac       864
        Ser Lys Ala Ile Gly Lys Lys Ile Lys Asn Asp Gly Thr Leu Asp Asn
             275                 280                 285 gaa gca aat cga aac gaa tca ttg ata gca gga gct tat gaa ata tca       912
        Glu Ala Asn Arg Asn Glu Ser Leu Ile Ala Gly Ala Tyr Glu Ile Ser
        290                 295                 300 aaa cta ata aca caa aaa tta agt gta ttg aat tca gaa gaa tta aag       960
        Lys Leu Ile Thr Gln Lys Leu Ser Val Leu Asn Ser Glu Glu Leu Lys
        305                 310                 315                 320 aaa aaa att aaa gag gct aag gat tgt tcc caa aaa ttt act act aag      1008
```

```
                Lys Lys Ile Lys Glu Ala Lys Asp Cys Ser Gln Lys Phe Thr Thr Lys
                            325                 330                 335 cta aaa gat agt cat gca gag ctt ggt ata caa agc gtt cag gat gat       1056
Leu Lys Asp Ser His Ala Glu Leu Gly Ile Gln Ser Val Gln Asp Asp
            340                 345                 350 aat gca aaa aaa gct att tta aaa aca cat gga act aaa gac aag ggt       1104
Asn Ala Lys Lys Ala Ile Leu Lys Thr His Gly Thr Lys Asp Lys Gly
            355                 360                 365 gct aaa gaa ctt gaa gag tta ttt aaa tca cta gaa agc ttg tca aaa       1152
Ala Lys Glu Leu Glu Glu Leu Phe Lys Ser Leu Glu Ser Leu Ser Lys
            370                 375                 380 gca gcg caa gca gca tta act aat tca gtt aaa gag ctt aca aat cct       1200
Ala Ala Gln Ala Ala Leu Thr Asn Ser Val Lys Glu Leu Thr Asn Pro
385                 390                 395                 400 gtt gtg gca gaa agt cca aaa aaa cct taa                               1230
Val Val Ala Glu Ser Pro Lys Lys Pro *
            405

<210> SEQ ID NO 78
<211> LENGTH: 409
<212> TYPE: PRT
<213> ORGANISM: ospC Chimera

<400> SEQUENCE: 78

Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
    50                  55                  60

Leu Ala Val Lys Glu Val Glu Ala Leu Leu Ser Ser Ile Asp Glu Ile
65                  70                  75                  80

Ala Ala Lys Ala Ile Gly Lys Lys Ile His Gln Asn Asn Gly Leu Asp
                85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
    130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190

Lys Ala Ala Lys Glu Met Leu Ala Asn Ser Val Lys Glu Leu Thr Ser
        195                 200                 205

Pro Val Val Ala Glu Ser Pro Lys Lys Pro Phe His Gly Asn Asn Ser
    210                 215                 220

Gly Gly Asp Ser Ala Ser Thr Asn Pro Asp Glu Ser Ala Lys Gly Pro
225                 230                 235                 240

Asn Leu Thr Val Ile Ser Lys Lys Ile Thr Asp Ser Asn Ala Phe Leu
                245                 250                 255
```

```
Leu Ala Val Lys Glu Val Glu Ala Leu Leu Ser Ser Ile Asp Glu Leu
            260                 265                 270

Ser Lys Ala Ile Gly Lys Lys Ile Lys Asn Asp Gly Thr Leu Asp Asn
            275                 280                 285

Glu Ala Asn Arg Asn Glu Ser Leu Ile Ala Gly Ala Tyr Glu Ile Ser
            290                 295                 300

Lys Leu Ile Thr Gln Lys Leu Ser Val Leu Asn Ser Glu Glu Leu Lys
305                 310                 315                 320

Lys Lys Ile Lys Glu Ala Lys Asp Cys Ser Gln Lys Phe Thr Thr Lys
                325                 330                 335

Leu Lys Asp Ser His Ala Glu Leu Gly Ile Gln Ser Val Gln Asp Asp
                340                 345                 350

Asn Ala Lys Lys Ala Ile Leu Lys Thr His Gly Thr Lys Asp Lys Gly
                355                 360                 365

Ala Lys Glu Leu Glu Glu Leu Phe Lys Ser Leu Glu Ser Leu Ser Lys
                370                 375                 380

Ala Ala Gln Ala Ala Leu Thr Asn Ser Val Lys Glu Leu Thr Asn Pro
385                 390                 395                 400

Val Val Ala Glu Ser Pro Lys Lys Pro
                405

<210> SEQ ID NO 79
<211> LENGTH: 1209
<212> TYPE: DNA
<213> ORGANISM: ospC Chimera
<220> FEATURE:
<221> NAME/KEY: CDS
<222> LOCATION: (1)...(1209)

<400> SEQUENCE: 79 atg aga tta tta ata gga ttt gct tta gcg tta gct tta ata gga tgt      48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
            20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
        35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
    50                  55                  60 ctt gct gtg aaa gag gtt gaa gcg ttg ctg tca tct ata gat gaa att     240
Leu Ala Val Lys Glu Val Glu Ala Leu Leu Ser Ser Ile Asp Glu Ile
65                  70                  75                  80 gct gct aaa gct att ggt aaa aaa ata cac caa aat aat ggt ttg gat     288
Ala Ala Lys Ala Ile Gly Lys Lys Ile His Gln Asn Asn Gly Leu Asp
                85                  90                  95 acc gaa tat aat cac aat gga tca ttg tta gcg gga gct tat gca ata     336
Thr Glu Tyr Asn His Asn Gly Ser Leu Leu Ala Gly Ala Tyr Ala Ile
            100                 105                 110 tca acc cta ata aaa caa aaa tta gat gga ttg aaa aat gaa gga tta     384
Ser Thr Leu Ile Lys Gln Lys Leu Asp Gly Leu Lys Asn Glu Gly Leu
        115                 120                 125 aag gaa aaa att gat gcg gct aag aaa tgt tct gaa aca ttt act aat     432
Lys Glu Lys Ile Asp Ala Ala Lys Lys Cys Ser Glu Thr Phe Thr Asn
    130                 135                 140 aaa tta aaa gaa aaa cac aca gat ctt ggt aaa gaa ggt gtt act gat     480
Lys Leu Lys Glu Lys His Thr Asp Leu Gly Lys Glu Gly Val Thr

```
                145                 150                 155                 160
gct gat gca aaa gaa gcc att tta aaa aca aat ggt act aaa act aaa      528
Ala Asp Ala Lys Glu Ala Ile Leu Lys Thr Asn Gly Thr Lys Thr Lys
                165                 170                 175 ggt gct gaa gaa ctt gga aaa tta ttt gaa tca gta gag gtc ttg tca      576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc      624
Lys Ala Ala Lys Glu Met Leu Ala Asn Ser Val Lys Glu Leu Thr Ser
        195                 200                 205 cct gtt gtg gca gaa agt cca aaa aaa cct tcc atg gta aat aat tca      672
Pro Val Val Ala Glu Ser Pro Lys Lys Pro Ser Met Val Asn Asn Ser
    210                 215                 220 ggg aaa gat ggg aat aca tct gca aat tct gct gat gag tct gtt aaa      720
Gly Lys Asp Gly Asn Thr Ser Ala Asn Ser Ala Asp Glu Ser Val Lys
225                 230                 235                 240 ggg cct aat ctt aca gaa ata agt aaa aaa att aca gaa tct aac gca      768
Gly Pro Asn Leu Thr Glu Ile Ser Lys Lys Ile Thr Glu Ser Asn Ala
                245                 250                 255 gtt gtt ctc gcc gtg aaa gaa gtt gaa act ttg ctt aca tct ata gat      816
Val Val Leu Ala Val Lys Glu Val Glu Thr Leu Leu Thr Ser Ile Asp
            260                 265                 270 gag ctt gct aaa gct att ggt aaa aaa ata aaa aac gat gtt agt tta      864
Glu Leu Ala Lys Ala Ile Gly Lys Lys Ile Lys Asn Asp Val Ser Leu
        275                 280                 285 gat aat gag gca gat cac aac gga tca tta ata tca gga gca tat tta      912
Asp Asn Glu Ala Asp His Asn Gly Ser Leu Ile Ser Gly Ala Tyr Leu
    290                 295                 300 att tca aac tta ata aca aaa aaa ata agt gca ata aaa gat tca gga      960
Ile Ser Asn Leu Ile Thr Lys Lys Ile Ser Ala Ile Lys Asp Ser Gly
305                 310                 315                 320 gaa ttg aag gca gaa att gaa aag gct aag aaa tgt tct gaa gaa ttt     1008
Glu Leu Lys Ala Glu Ile Glu Lys Ala Lys Lys Cys Ser Glu Glu Phe
                325                 330                 335 act gct aaa tta aaa ggt gaa cac aca gat ctt ggt aaa gaa ggc gtt     1056
Thr Ala Lys Leu Lys Gly Glu His Thr Asp Leu Gly Lys Glu Gly Val
            340                 345                 350 act gat gat aat gca aaa aaa gcc att tta aaa aca aat aat gat aaa     1104
Thr Asp Asp Asn Ala Lys Lys Ala Ile Leu Lys Thr Asn Asn Asp Lys
        355                 360                 365 act aag ggc gct gat gaa ctt gaa aag tta ttt gaa tca gta aaa aac     1152
Thr Lys Gly Ala Asp Glu Leu Glu Lys Leu Phe Glu Ser Val Lys Asn
    370                 375                 380 ttg tca aaa gca gct aaa gag atg ctt act aat tca gtt aaa gag ctt     1200
Leu Ser Lys Ala Ala Lys Glu Met Leu Thr Asn Ser Val Lys Glu Leu
385                 390                 395                 400 aca agc taa                                                          1209
Thr Ser *

<210> SEQ ID NO 80
<211> LENGTH: 402
<212> TYPE: PRT
<213> ORGANISM: ospC Chimera

<400> SEQUENCE: 80

Met Arg Leu Leu Ile Gly Phe Ala Leu Ala Leu Ala Leu Ile Gly Cys
  1               5                  10                  15

Ala Gln Lys Gly Ala Glu Ser Ile Gly Ser Cys Asn Asn Ser Gly Lys
            20                  25                  30
```

```
Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
     50                  55                  60

Leu Ala Val Lys Glu Val Glu Ala Leu Leu Ser Ser Ile Asp Glu Ile
 65                  70                  75                  80

Ala Ala Lys Ala Ile Gly Lys Lys Ile His Gln Asn Asn Gly Leu Asp
                 85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
    130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190

Lys Ala Ala Lys Glu Met Leu Ala Asn Ser Val Lys Glu Leu Thr Ser
        195                 200                 205

Pro Val Val Ala Glu Ser Pro Lys Lys Pro Ser Met Val Asn Asn Ser
    210                 215                 220

Gly Lys Asp Gly Asn Thr Ser Ala Asn Ser Ala Asp Glu Ser Val Lys
225                 230                 235                 240

Gly Pro Asn Leu Thr Glu Ile Ser Lys Lys Ile Thr Glu Ser Asn Ala
                245                 250                 255

Val Val Leu Ala Val Lys Glu Val Glu Thr Leu Leu Thr Ser Ile Asp
            260                 265                 270

Glu Leu Ala Lys Ala Ile Gly Lys Lys Ile Lys Asn Asp Val Ser Leu
        275                 280                 285

Asp Asn Glu Ala Asp His Asn Gly Ser Leu Ile Ser Gly Ala Tyr Leu
    290                 295                 300

Ile Ser Asn Leu Ile Thr Lys Lys Ile Ser Ala Ile Lys Asp Ser Gly
305                 310                 315                 320

Glu Leu Lys Ala Glu Ile Glu Lys Ala Lys Lys Cys Ser Glu Glu Phe
                325                 330                 335

Thr Ala Lys Leu Lys Gly Glu His Thr Asp Leu Gly Lys Glu Gly Val
            340                 345                 350

Thr Asp Asp Asn Ala Lys Lys Ala Ile Leu Lys Thr Asn Asn Asp Lys
        355                 360                 365

Thr Lys Gly Ala Asp Glu Leu Glu Lys Leu Phe Glu Ser Val Lys Asn
    370                 375                 380

Leu Ser Lys Ala Ala Lys Glu Met Leu Thr Asn Ser Val Lys Glu Leu
385                 390                 395                 400

Thr Ser
```

<210> SEQ ID NO 81
<211> LENGTH: 1205
<212> TYPE: DNA
<213> ORGANISM: ospC Chimera
<220> FEATURE:
<221> NAME/KEY: CDS
<222> LOCATION: (1)...(1205)

-continued

```
<400> SEQUENCE: 81 atg aga tta tta ata gga ttt gct tta gcg tta gct tta ata gga tgt      48
Met Arg Leu Leu Ile Gly Phe Ala Leu Ala Leu Ala Leu Ile Gly Cys
 1               5                  10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
             20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
         35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
     50                  55                  60 ctt gct gtg aaa gag gtt gaa gcg ttg ctg tca tct ata gat gaa att     240
Leu Ala Val Lys Glu Val Glu Ala Leu Leu Ser Ser Ile Asp Glu Ile
 65                  70                  75                  80 gct gct aaa gct att ggt aaa aaa ata cac caa aat aat ggt ttg gat     288
Ala Ala Lys Ala Ile Gly Lys Lys Ile His Gln Asn Asn Gly Leu Asp
                 85                  90                  95 acc gaa tat aat cac aat gga tca ttg tta gcg gga gct tat gca ata     336
Thr Glu Tyr Asn His Asn Gly Ser Leu Leu Ala Gly Ala Tyr Ala Ile
            100                 105                 110 tca acc cta ata aaa caa aaa tta gat gga ttg aaa aat gaa gga tta     384
Ser Thr Leu Ile Lys Gln Lys Leu Asp Gly Leu Lys Asn Glu Gly Leu
        115                 120                 125 aag gaa aaa att gat gcg gct aag aaa tgt tct gaa aca ttt act aat     432
Lys Glu Lys Ile Asp Ala Ala Lys Lys Cys Ser Glu Thr Phe Thr Asn
    130                 135                 140 aaa tta aaa gaa aaa cac aca gat ctt ggt aaa gaa ggt gtt act gat     480
Lys Leu Lys Glu Lys His Thr Asp Leu Gly Lys Glu Gly Val Thr Asp
145                 150                 155                 160 gct gat gca aaa gaa gcc att tta aaa aca aat ggt act aaa act aaa     528
Ala Asp Ala Lys Glu Ala Ile Leu Lys Thr Asn Gly Thr Lys Thr Lys
                165                 170                 175 ggt gct gaa gaa ctt gga aaa tta ttt gaa tca gta gag gtc ttg tca     576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc     624
Lys Ala Ala Lys Glu Met Leu Ala Asn Ser Val Lys Glu Leu Thr Ser
        195                 200                 205 cct gtt gtg gca gaa agt cca aaa aaa cct tcc atg gta aat aat tca     672
Pro Val Val Ala Glu Ser Pro Lys Lys Pro Ser Met Val Asn Asn Ser
    210                 215                 220 gga aaa gat ggg aat aca tct gca aat tct gct gat gag tct gtt aaa     720
Gly Lys Asp Gly Asn Thr Ser Ala Asn Ser Ala Asp Glu Ser Val Lys
225                 230                 235                 240 ggg cct aat ctt aca gaa ata agt aaa aaa att aca gaa tct aac gca     768
Gly Pro Asn Leu Thr Glu Ile Ser Lys Lys Ile Thr Glu Ser Asn Ala
                245                 250                 255 gtt gtt ctg gct gtg aaa gaa att gaa act ttg ctt gca tct ata gat     816
Val Val Leu Ala Val Lys Glu Ile Glu Thr Leu Leu Ala Ser Ile Asp
            260                 265                 270 gaa ctt gct act aaa gct att ggt aaa aaa ata caa caa aat ggt ggt     864
Glu Leu Ala Thr Lys Ala Ile Gly Lys Lys Ile Gln Gln Asn Gly Gly
        275                 280                 285 tta gct gtc gaa gcg ggg cat aat gga aca ttg tta gca ggt gct tat     912
Leu Ala Val Glu Ala Gly His Asn Gly Thr Leu Leu Ala Gly Ala Tyr
    290                 295                 300
```

```
aca ata tca aaa cta ata aca caa aaa tta gat gga ttg aaa aat tca        960
Thr Ile Ser Lys Leu Ile Thr Gln Lys Leu Asp Gly Leu Lys Asn Ser
305                 310                 315                 320 gaa aaa tta aag gaa aaa att gaa aat gct aag aaa tgt tct gaa gat       1008
Glu Lys Leu Lys Glu Lys Ile Glu Asn Ala Lys Lys Cys Ser Glu Asp
            325                 330                 335 ttt act aaa aaa cta gaa gga gaa cat gcg caa ctt gga att gaa aat       1056
Phe Thr Lys Lys Leu Glu Gly Glu His Ala Gln Leu Gly Ile Glu Asn
        340                 345                 350 gtt act gat gag aat gca aaa aaa gct att tta ata aca gat gca gct       1104
Val Thr Asp Glu Asn Ala Lys Lys Ala Ile Leu Ile Thr Asp Ala Ala
    355                 360                 365 aaa gat aag ggc gct gca gag ctt gaa aag cta ttt aaa gca gta gaa       1152
Lys Asp Lys Gly Ala Ala Glu Leu Glu Lys Leu Phe Lys Ala Val Glu
370                 375                 380 aac ttg gca aaa gca gct aaa gag atg ctt gct aat tca gtt aaa gag       1200
Asn Leu Ala Lys Ala Ala Lys Glu Met Leu Ala Asn Ser Val Lys Glu
385                 390                 395                 400 ctt ac                                                                1205
Leu

<210> SEQ ID NO 82
<211> LENGTH: 401
<212> TYPE: PRT
<213> ORGANISM: ospC Chimera

<400> SEQUENCE: 82

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
    50                  55                  60

Leu Ala Val Lys Glu Val Glu Ala Leu Leu Ser Ser Ile Asp Glu Ile
65                  70                  75                  80

Ala Ala Lys Ala Ile Gly Lys Lys Ile His Gln Asn Asn Gly Leu Asp
                85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
    130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190

Lys Ala Ala Lys Glu Met Leu Ala Asn Ser Val Lys Glu Leu Thr Ser
        195                 200                 205

Pro Val Val Ala Glu Ser Pro Lys Lys Pro Ser Met Val Asn Asn Ser
    210                 215                 220

Gly Lys Asp Gly Asn Thr Ser Ala Asn Ser Ala Asp Glu Ser Val Lys
225                 230                 235                 240
```

```
Gly Pro Asn Leu Thr Glu Ile Ser Lys Lys Ile Thr Glu Ser Asn Ala
            245                 250                 255

Val Val Leu Ala Val Lys Glu Ile Glu Thr Leu Leu Ala Ser Ile Asp
        260                 265                 270

Glu Leu Ala Thr Lys Ala Ile Gly Lys Lys Ile Gln Gln Asn Gly Gly
    275                 280                 285

Leu Ala Val Glu Ala Gly His Asn Gly Thr Leu Ala Gly Ala Tyr
290                 295                 300

Thr Ile Ser Lys Leu Ile Thr Gln Lys Leu Asp Gly Leu Lys Asn Ser
305                 310                 315                 320

Glu Lys Leu Lys Glu Lys Ile Glu Asn Ala Lys Lys Cys Ser Glu Asp
            325                 330                 335

Phe Thr Lys Lys Leu Glu Gly Glu His Ala Gln Leu Gly Ile Glu Asn
        340                 345                 350

Val Thr Asp Glu Asn Ala Lys Lys Ala Ile Leu Ile Thr Asp Ala Ala
    355                 360                 365

Lys Asp Lys Gly Ala Ala Glu Leu Glu Lys Leu Phe Lys Ala Val Glu
370                 375                 380

Asn Leu Ala Lys Ala Ala Lys Glu Met Leu Ala Asn Ser Val Lys Glu
385                 390                 395                 400

Leu

<210> SEQ ID NO 83
<211> LENGTH: 1236
<212> TYPE: DNA
<213> ORGANISM: ospC Chimera
<220> F -continued

```
act aat aaa cta aaa agt ggt cat gca gat ctt ggc aaa cag gat gct    480
Thr Asn Lys Leu Lys Ser Gly His Ala Asp Leu Gly Lys Gln Asp Ala
145                 150                 155                 160 acc gat gat cat gca aaa gca gct att tta aaa aca cat gca act acc    528
Thr Asp Asp His Ala Lys Ala Ala Ile Leu Lys Thr His Ala Thr Thr
                165                 170                 175 gat aaa ggt gct aaa gaa ttt aaa gat tta ttt gaa tca gta gaa ggt    576
Asp Lys Gly Ala Lys Glu Phe Lys Asp Leu Phe Glu Ser Val Glu Gly
            180                 185                 190 ttg tta aaa gca gct caa gta gca cta act aat tca gtt aaa gaa ctt    624
Leu Leu Lys Ala Ala Gln Val Ala Leu Thr Asn Ser Val Lys Glu Leu
        195                 200                 205 aca agt cct gtt gta gca gaa agt cca aaa aaa cct cat atg gct aat    672
Thr Ser Pro Val Val Ala Glu Ser Pro Lys Lys Pro His Met Ala Asn
210                 215                 220 aat tca ggt ggg gat tct gca tct act aat cct gat gag tct gca aaa    720
Asn Ser Gly Gly Asp Ser Ala Ser Thr Asn Pro Asp Glu Ser Ala Lys
225                 230                 235                 240 gga cct aat ctt acc gta ata agc aaa aaa att aca gat tct aat gca    768
Gly Pro Asn Leu Thr Val Ile Ser Lys Lys Ile Thr Asp Ser Asn Ala
                245                 250                 255 ttt tta ctg gct gtg aaa gaa gtt gag gct ttg ctt tca tct ata gat    816
Phe Leu Leu Ala Val Lys Glu Val Glu Ala Leu Leu Ser Ser Ile Asp
            260                 265                 270 gaa ctt tct aaa gct att ggt aaa aaa ata aaa aat gat ggt act tta    864
Glu Leu Ser Lys Ala Ile Gly Lys Lys Ile Lys Asn Asp Gly Thr Leu
        275                 280                 285 gat aac gaa gca aat cga aac gaa tca ttg ata gca gga gct tat gaa    912
Asp Asn Glu Ala Asn Arg Asn Glu Ser Leu Ile Ala Gly Ala Tyr Glu
290                 295                 300 ata tca aaa cta ata aca caa aaa tta agt gta ttg aat tca gaa gaa    960
Ile Ser Lys Leu Ile Thr Gln Lys Leu Ser Val Leu Asn Ser Glu Glu
305                 310                 315                 320 tta aag aaa aaa att aaa gag gct aag gat tgt tcc caa aaa ttt act    1008
Leu Lys Lys Lys Ile Lys Glu Ala Lys Asp Cys Ser Gln Lys Phe Thr
                325                 330                 335 act aag cta aaa gat agt cat gca gag ctt ggt ata caa agc gtt cag    1056
Thr Lys Leu Lys Asp Ser His Ala Glu Leu Gly Ile Gln Ser Val Gln
            340                 345                 350 gat gat aat gca aaa aaa gct att tta aaa aca cat gga act aaa gac    1104
Asp Asp Asn Ala Lys Lys Ala Ile Leu Lys Thr His Gly Thr Lys Asp
        355                 360                 365 aag ggt gct aaa gaa ctt gaa gag tta ttt aaa tca cta gaa agc ttg    1152
Lys Gly Ala Lys Glu Leu Glu Glu Leu Phe Lys Ser Leu Glu Ser Leu
370                 375                 380 tca aaa gca gcg caa gca gca tta act aat tca gtt aaa gag ctt aca    1200
Ser Lys Ala Ala Gln Ala Ala Leu Thr Asn Ser Val Lys Glu Leu Thr
385                 390                 395                 400 aat cct gtt gtg gca gaa agt cca aaa aaa cct taa                    1236
Asn Pro Val Val Ala Glu Ser Pro Lys Lys Pro *
                405                 410
```

<210> SEQ ID NO 84
<211> LENGTH: 411
<212> TYPE: PRT
<213> ORGANISM: ospC Chimera

<400> SEQUENCE: 84

```
Met Arg Leu Leu Ile Gly Phe Ala Leu Ala Leu Ala Leu Ile Gly Cys
1               5

```
Ala Gln Lys Gly Ala Glu Ser Ile Gly Ser Cys Ser Asn Ser Gly Lys
            20                  25                  30

Gly Gly Asp Ser Ala Ser Thr Asn Pro Ala Asp Glu Ser Ala Lys Gly
        35                  40                  45

Pro Asn Leu Thr Glu Ile Ser Lys Lys Ile Thr Asp Ser Asn Ala Phe
    50                  55                  60

Val Leu Ala Val Lys Glu Val Glu Thr Leu Val Leu Ser Ile Asp Glu
65                  70                  75                  80

Leu Ala Lys Lys Ala Ile Gly Gln Lys Ile Asp Asn Asn Asn Gly Leu
                85                  90                  95

Ala Ala Leu Asn Asn Gln Asn Gly Ser Leu Leu Ala Gly Ala Tyr Ala
            100                 105                 110

Ile Ser Thr Leu Ile Thr Glu Lys Leu Ser Lys Leu Lys Asn Leu Glu
            115                 120                 125

Glu Leu Lys Thr Glu Ile Ala Lys Ala Lys Lys Cys Ser Glu Glu Phe
            130                 135                 140

Thr Asn Lys Leu Lys Ser Gly His Ala Asp Leu Gly Lys Gln Asp Ala
145                 150                 155                 160

Thr Asp His Ala Lys Ala Ala Ile Leu Lys Thr His Ala Thr Thr
                165                 170                 175

Asp Lys Gly Ala Lys Glu Phe Lys Asp Leu Phe Glu Ser Val Glu Gly
            180                 185                 190

Leu Leu Lys Ala Ala Gln Val Ala Leu Thr Asn Ser Val Lys Glu Leu
            195                 200                 205

Thr Ser Pro Val Val Ala Glu Ser Pro Lys Lys Pro His Met Ala Asn
    210                 215                 220

Asn Ser Gly Gly Asp Ser Ala Ser Thr Asn Pro Asp Glu Ser Ala Lys
225                 230                 235                 240

Gly Pro Asn Leu Thr Val Ile Ser Lys Lys Ile Thr Asp Ser Asn Ala
                245                 250                 255

Phe Leu Leu Ala Val Lys Glu Val Glu Ala Leu Leu Ser Ser Ile Asp
            260                 265                 270

Glu Leu Ser Lys Ala Ile Gly Lys Lys Ile Lys Asn Asp Gly Thr Leu
            275                 280                 285

Asp Asn Glu Ala Asn Arg Asn Glu Ser Leu Ile Ala Gly Ala Tyr Glu
            290                 295                 300

Ile Ser Lys Leu Ile Thr Gln Lys Leu Ser Val Leu Asn Ser Glu Glu
305                 310                 315                 320

Leu Lys Lys Lys Ile Lys Glu Ala Lys Asp Cys Ser Gln Lys Phe Thr
                325                 330                 335

Thr Lys Leu Lys Asp Ser His Ala Glu Leu Gly Ile Gln Ser Val Gln
            340                 345                 350

Asp Asp Asn Ala Lys Lys Ala Ile Leu Lys Thr His Gly Thr Lys Asp
            355                 360                 365

Lys Gly Ala Lys Glu Leu Glu Glu Leu Phe Lys Ser Leu Glu Ser Leu
    370                 375                 380

Ser Lys Ala Ala Gln Ala Ala Leu Thr Asn Ser Val Lys Glu Leu Thr
385                 390                 395                 400

Asn Pro Val Val Ala Glu Ser Pro Lys Lys Pro
            405                 410
```

<210> SEQ ID NO 85
<211> LENGTH: 192

-continued

```
<212> TYPE: PRT
<213> ORGANISM: borrelia burgdorferi

<400> SEQUENCE: 85

Cys Asn Asn Ser Gly Lys Asp Gly Asn Thr Ser Ala Asn Ser Ala Asp
 1               5                  10                  15

Glu Ser Val Lys Gly Pro Asn Leu Thr Glu Ile Ser Lys Lys Ile Thr
            20                  25                  30

Glu Ser Asn Ala Val Val Leu Ala Val Lys Glu Val Glu Thr Leu Leu
        35                  40                  45

Thr Ser Ile Asp Glu Leu Ala Lys Ala Ile Gly Lys Lys Ile Lys Asn
    50                  55                  60

Asp Val Ser Leu Asp Asn Glu Ala Asp His Asn Gly Ser Leu Ile Ser
65                  70                  75                  80

Gly Ala Tyr Leu Ile Ser Thr Leu Ile Thr Lys Lys Ile Ser Ala Ile
                85                  90                  95

Lys Asp Ser Gly Glu Leu Lys Ala Glu Ile Glu Lys Ala Lys Lys Cys
            100                 105                 110

Ser Glu Glu Phe Thr Ala Lys Leu Lys Gly Glu His Thr Asp Leu Gly
        115                 120                 125

Lys Glu Gly Val Thr Asp Asp Asn Ala Lys Lys Ala Ile Leu Lys Thr
    130                 135                 140

Asn Asn Asp Lys Thr Lys Gly Ala Asp Glu Leu Glu Lys Leu Phe Glu
145                 150                 155                 160

Ser Val Lys Asn Leu Ser Lys Ala Ala Lys Glu Met Leu Thr Asn Ser
                165                 170                 175

Val Lys Glu Leu Thr Ser Pro Val Val Ala Glu Ser Pro Lys Lys Pro
            180                 185                 190

<210> SEQ ID NO 86
<211> LENGTH: 191
<212> TYPE: PRT
<213> ORGANISM: borrelia burgdorferi

<400> SEQUENCE: 86

Asn Ser Gly Lys Gly Gly Asn Thr Ser Ala Asn Ser Ala Asp Glu Ser
 1               5                  10                  15

Val Lys Gly Pro Asn Leu Thr Glu Ile Ser Lys Lys Ile Thr Glu Ser
            20                  25                  30

Asn Ala Val Val Leu Ala Val Lys Glu Ile Glu Thr Leu Leu Ala Ser
        35                  40                  45

Ile Asp Glu Leu Ala Thr Lys Ala Ile Gly Lys Lys Ile Gln Gln Asn
    50                  55                  60

Gly Gly Leu Ala Val Glu Ala Gly His Asn Gly Thr Leu Leu Ala Gly
65                  70                  75                  80

Ala Tyr Thr Ile Ser Lys Leu Ile Thr Gln Lys Leu Asp Gly Leu Lys
                85                  90                  95

Asn Ser Glu Lys Leu Lys Glu Lys Ile Glu Asn Ala Lys Lys Cys Ser
            100                 105                 110

Glu Asp Phe Thr Lys Lys Leu Glu Gly Glu His Ala Gln Leu Gly Ile
        115                 120                 125

Glu Asn Val Thr Asp Glu Asn Ala Lys Lys Ala Ile Leu Ile Thr Asp
    130                 135                 140

Ala Ala Lys Asp Lys Gly Ala Ala Glu Leu Glu Lys Leu Phe Lys Ala
145                 150                 155                 160

```
                                     -continued
Val Glu Asn Leu Ala Lys Ala Ala Lys Glu Met Leu Ala Asn Ser Val
                165                 170                 175

Lys Glu Leu Thr Ser Pro Ile Val Ala Glu Ser Pro Lys Lys Pro
                180                 185                 190
```

GROUPS OF *BORRELIA BURGDORFERI* AND *BORRELIA AFZELII* THAT CAUSE LYME DISEASE IN HUMANS

RELATED APPLICATIONS

This application is a divisional of U.S. application Ser. No. 09/596,746, filed Jun. 19, 2000, now U.S. Pat. No. 7,060,281, which claims the benefit of U.S. Provisional Application No. 60/140,042, filed Jun. 18, 1999.

The entire teachings of the above applications are incorporated herein by reference.

GOVERNMENT SUPPORT

The invention was supported, in whole or in part, by grant AIAR37256 from The National Institutes of Health, grant RO1AI33454 from the National Institute of Infectious Disease and cooperative agreement number U50/CCU210518 from the Centers for Disease Control. The Government has certain rights in the invention.

BACKGROUND OF THE INVENTION

Lyme disease begins at the site of a tick bite, producing a primary infection with spread of the organism to secondary sites occurring early in the course of infection. Lyme disease is a progressive multi-system disorder and is the most common vector-borne disease in both North America and Europe. This disease was first described as a focus of pediatric arthritis patients in Old Lyme, Conn. (Steere, A. C., et al., *Arth. Rheum.*, 20:17 (1977)). The association of this syndrome with the bite of the deer tick, *Ixodes scapularis*, led to the identification of the spirochete *Borrelia burgdorferi* as the causative agent (Burgdorfer, W., et al. *Science*, 216:1317-1319 (1982)). As culture isolation of the bacterium from clinical and field samples became more efficient, Baranton and colleagues described three pathogenic genospecies, *B. burgdorferi* sensu stricto (*B. burgdorferi* or B.b.s.s.), *B. afzelii*, and *B. garinii* (Baraton, G., et al., *Int. J. Syst. Bacteriol.*, 42:378-383 (1992)). These are members of a species complex, *B. burgdorferi* sensu lato, which consists of at least 10 different genospecies (Piken, R. N., et al., *J. Invest. Dermatol.*, 110: 211-214 (1998); Postic, D., et al., *Int. J. Syst. Bacteriol.*, 44:743-752 (1994); Valsangiacomo, C. T., et al., *Int. J. Syst. Bacteriol.*, 47:1-10 (1997)). *B. burgdorferi*, *B. afzelii* and *B. garinii* are thought to be pathogenic and all are found in Europe, but in North America, *B. burgdorferi* is the only pathogenic genospecies found. Each of these three genospecies is associated with distinct clinical manifestations (Van Dam, A. P. et al., *Clin. Infect. Dis.*, 17:708-717 (1993)). This implies that differences in genospecies may play an important role in the wide array of clinical manifestations observed in Lyme Disease. However, because OspC is highly variable in its sequence, the protection is limited to the *Borrelia burgdorferi* strain expressing the same immunizing OspC encoded by a specific allele. Challenge with heterologous isolates, expressing other ospC alleles results in infections (Probert, W. S., et al., *J. Infect. D.,* 175:400-405 (1997)). OspC is very diverse (Jauris-Heipke, S., et al., *Med. Microbiol. Immunol.* 182:37-50 (1993)). Livey et al. found thirty-four alleles in seventy-six *B. burgdorferi sensu lato* isolates (Livey, I., et al., *Mol. Microbiol.* 18:257-269 (1995)).

Currently, Lyme Disease is treated with antibiotics. However, such treatment is not always successful in clearing the infection. Treatment is often delayed due to improper diagnosis with the deleterious effect that the infection proceeds to a chronic condition, where treatment with antibiotics is often not useful. One of the factors contributing to delayed treatment is the lack of effective diagnostic tools. W Furthermore, while antigens such as OspC are known to be protective, in some cases the existence of multiple alleles of these antigens greatly hinders the development of vaccines based on such antigens that would protect against more than one strain of *Borrelia*. Two independent trials of first generation vaccines for the prevention of Lyme disease, recently studied the efficacy and safety of a vaccine that is based on recombinant outer surface protein A (OspA) (Sigal, L. H. et al., *N. Engl. J. Med* 339:216-222, 1998; Steere, A. C. et al., *N. Engl. J. Med.* 339:209-215, (1998)). However, a vaccine that consists of recombinant OspA may require frequent booster immunizations. Natural infection with *B. burgdorferi* does not elicit an antibody response to OspA, as it does against OspC. What is needed is a selection of *Borrelia* antigens that can be used to either diagnose or vaccinate against all or most forms of *Borrelia* that cause systemic disease.

Differences in the frequency of *B. burgdorferi, B. garinii*, and *B. afzelii* in ticks and human infection has lead to the hypothesis that the different genospecies are differentially pathogenic (Picken, R. N. et al., *J. Invest. Dermatol.* 110:211-214, 1998; Van Dam, A. P. et al., *Clin. Infect. Dis.* 17:708-717, 1993). Nevertheless, the number of different strains within a given genospecies and the differences between the strains of a given genospecies as well as between genospecies impose obstacles in the development of immunogenic protein compounds for use as diagnostic and vaccine agents in the detection, prevention and treatment of Lyme disease. A number of investigators have used OspC as a serodiagnostic antigen for early Lyme disease (Fung, B. P. et al., *Infect. Immun.* 62:3213-3221, 1994; Gerber, M. A. et al., *J. Infect. Dis.* 171:724-727, 1995; Padula, S. J. et al., *J. Clin. Microbiol.* 32:1733-1738, (1994)). In these tests, the use of OspC as a diagnostic antigen gave highly specific, but not sensitive results. However, these studies included only one *B. burgdorferi* strain and therefore only one type of OspC. Routine tests for the diagnosis of Lyme disease also use a single strain protocol and therefore a single OspC allele for detection of antibody to the sprirochete. It is not clear what mixture of OspC proteins must be used to make useful diagnostic and vaccine tools, effective against more than one Lyme disease causing strains of *Borrelia*, if not against most if not all of the invasive strains within a genospecies.

Preferably, such a mixture would be effective against all invasive strains of Lyme disease causing *Borrelia.*

SUMMARY OF THE INVENTION

The present invention is drawn to a composition comprising OspC polypeptides from Lyme Disease causing *Borrelia*. In one embodiment, the composition of the present invention comprises an OspC polypeptide or fragment thereof from at least two *Borrelia burgdorferi* OspC families selected from the group consisting of A, B, I and K, excepting the combination consisting of two OspC proteins, wherein one OspC protein is from OspC family A and the second OspC protein is from OspC family I. In another embodiment, the composition of the present invention comprises at least one OspC polypeptide or fragment thereof from each of *Borrelia afzelii* OspC families A and B.

The present invention is also drawn to a method of immunizing an animal against Lyme disease, comprising administering a composition comprising OspC polypeptides from Lyme Disease causing *Borrelia*. In one embodiment of the present invention, the composition comprises a OspC polypeptide or fragment thereof from at least two *Borrelia burgdorferi* OspC families selected from the group consisting of: A, B, I and K, excepting the combination consisting of two OspC proteins, wherein one OspC protein is from OspC family A and the second OspC protein is from OspC family I. In another embodiment of the present invention, the composition comprises at least one OspC polypeptide or fragment thereof from each of *Borrelia afzelii* OspC families A and B. The composition of the present invention together with suitable excipients and/or adjuvants is administered to an animal such that the animal develops an immune response to at least one OspC polypeptide of the composition.

The present invention is also drawn to a method of detecting an immune response to Lyme Disease causing *Borrelia* in a host sample. The method comprises contacting a host sample with a composition comprising OspC polypeptides from Lyme disease causing strains of *Borrelia*, such that anti-OspC antibodies, if present, in said sample bind to said OspC polypeptides. In one embodiment, the composition comprises at least one OspC polypeptide or fragment thereof from each of *Borrelia burgdorferi* OspC families A, B, I and K. The amount of antibodies that have bound said OspC polypeptides or fragments thereof are measured; thereby detecting an immune response to Lyme disease causing *Borrelia*.

The present invention is also drawn to a diagnostic kit comprising OspC polypeptides from Lyme Disease causing *Borrelia*. In one embodiment of the present invention, the diagnostic kit comprises at least one OspC polypeptide or diagnostic fragment thereof from each of *Borrelia burgdorferi* OspC families A, B, I and K. In another embodiment of the present invention, the diagnostic composition comprises at least one OspC polypeptide or diagnostic fragment thereof from each of *Borrelia afzelii* OspC families A and B.

In other embodiments of the present invention, the composition comprises at least one OspC polypeptide or fragment thereof from each of *Borrelia afzelii* OspC families A and B. In still other embodiments, the composition comprises OspC polypeptides or fragments thereof from *Borrelia burgdorferi*, *Borrelia afzelii*, *Borrelia garinii* and combinations thereof.

The present invention is also drawn to chimeric proteins for use in the methods of the present invention. In one embodiment, the present invention is drawn to a chimeric protein comprising OspC polypeptides from two or more OspC families of Lyme Disease causing *Borrelia*. In one embodiment, the families comprise *Borrelia burgdorferi* OspC families A, B, I and K. In other embodiment, the families comprise *Borrelia afzelii* OspC families A and B. In still other embodiments, the composition comprises chimeric OspC polypeptides or fragments thereof from *Borrelia burgdorferi*, *Borrelia afzelii*, *Borrelia garinii* and combinations thereof.

The chimeric proteins of the present invention comprise at least a first and a second polypeptide of OspC, such that the first polypeptide comprises OspC from about base 26 to about base 630 of a first ospC gene and the second polypeptide comprises about base 28 to about base 570 of a second ospC gene. The chimeric proteins of the present invention can be used in the immunization and detection methods of the present invention.

The present invention provides the minimum number of *Borrelia burgdorferi* and *Borrelia afzelii* families that are responsible for systemic disease in humans and is useful for vaccines and diagnostic kits. The present invention provides a combination of proteins that, when used as a vaccine, prevent Lyme disease from becoming systemic. The proteins and chimeric proteins of the present invention can be effective in preventing of Lyme disease as well as having a therapeutic effect on established infection, for example after the tick bite is noticed by the patient. The proteins and chimeric proteins of the present invention are expected to act at the level of the tick as well as the level of the host in preventing both infection and disease due to *Borrelia burgdorferi*, *Borrelia afzelii* and/or *Borrelia garinii*. The present invention allows the development of a worldwide vaccine comprising only six proteins necessary to generate a protective immune response against all pathogenic strains of *Borrelia burgdorferi* and *Borrelia afzelii*.

The present invention also provides improved diagnostic tools. Because of the present invention it is now possible to prepare diagnostic tools comprising OspC antigens representing the four pathogenic families of *Borrelia burgdorferi* and/or the two pathogenic families of *Borrelia afzelii*, thereby detecting clinically important exposure to pathogenic bacteria while overlooking the remainder of the families which do not cause pathogenic disease.

As demonstrated herein, a significant proportion if not all, systemic *B. burgdorferi* sensu stricto infections in humans are associated with four ospC groups and that a significant portion, if not all, systematic *B. afzelii* infections in humans are associated with two ospC groups. Vaccines against OspC are known to be protective, but have been limited by the diversity of ospC (Probert, W. S. et al., *J. Infect. D.* 175:400-405, (1997)). The polypeptides of tie present invention provide immunogenic proteins, fragments and chimeric proteins thereof for highly protective vaccines and diagnostics. The present invention provides a vaccine that includes one or more of these four forms of OspC. The vaccines of the present invention should be an important second level of protection against disseminated infection of the *B. burgdorferi* spirochete. Furthermore, single-stranded conformational polymorphism (SSCP) analysis described herein may provide a rapid and powerful tool to monitor vaccine efficacy by detecting rare or new invasive ospC groups.

New diagnostic assays of the present invention, based on major ospC groups A, B, I, and K are useful to identify those at risk for progressive illness. Given that OspC proteins are antigenically variable, individuals infected with one strain may produce an antibody response that is not reactive with an OspC protein from a different major group. Antibody detection using antigen preparations of the present invention, incorporating a proper mix of invasive clones of *B. burgdorferi* will be much more sensitive than the present, single strain protocols. The compositions of the present invention not only elicit humoral and cell mediated immune responses, the compositions of the present invention are also capable of detecting both humoral and cell mediated immune response when used to test a host sample.

The present invention provides both lipidated OspC polypeptides, fragments thereof and chimeric proteins comprising two or more OspC polypeptides, wherein the chimeric protein has a lipidation signal, such as the lipidation signal from outer surface protein B at the 5' terminus of the gene encoding the chimera. Furthermore, the present invention provides unlipidated OspC polypeptides, fragments thereof and chimeric proteins comprising two or more OspC polypeptides, wherein the gene encoding the chimeric protein does not comprise a lipidation signal and the chimeric protein is not lipidated. Unlipidated OspC polypeptides, fragments thereof and chimeric proteins thereof are advantageous due to simpler production methods, improved yields of protein and simpler purification. The unlipidated chimeric proteins of the present invention unexpectedly elicit an immune response against Lyme disease causing strains of *Borrelia* at least as broadly reactive as lipidated OspC proteins that are used as a positive control. Furthermore, the unlipidated OspC chimeric proteins of the present invention elicit an immune response to more than one genospecies of Lyme disease causing strains of *Borrelia*, including genospecies and strains that are not used to generate the chimeric OspC immunogen.

BRIEF DESCRIPTION OF THE DRAWINGS

FIG. 1 is a schematic diagram of the frequency distribution of major ospC groups among *B. burgdorferi* isolates from Eastern Long Island *Ixodes scapularis* ticks.

FIG. 2 is a bar graph showing the reactivity of serum from mice immunized with the indicated *Borrelia* protein or recombinant chimeric *Borrelia* protein (X-axis) against the indicated OspC antigens (legend) where the serum is from the first bleed.

FIG. 3 is a bar graph showing the reactivity of serum from mice immunized with the indicated *Borrelia* protein or recombinant chimeric *Borrelia* protein (X-axis) against the indicated OspC antigens (legend) where the serum is from the second bleed.

FIG. 4 is a bar graph showing the reactivity of serum from mice immunized with the indicated *Borrelia* protein or chimeric recombinant *Borrelia* protein (X-axis) against the indicated strains of *Borrelia burgdorferi* sensu stricto (legend).

FIG. 5 is a bar graph showing the reactivity of serum from mice immunized with the indicated *Borrelia* protein or chimeric recombinant *Borrelia* protein (X-axis) against the indicated strains of *Borrelia burgdorferi* sensu lato (legend).

FIG. 6 is bar graph showing the reactivity of serum from mice immunized with the indicated *Borrelia* protein or chimeric recombinant *Borrelia* protein (X-axis) against the indicated strains of *Borrelia afzelii* (legend).

FIG. 7 is bar graph showing the reactivity of serum from mice immunized with the indicated *Borrelia* protein or chimeric recombinant *Borrelia* protein (X-axis) against the indicated strains of *Borrelia garinii* (legend).

FIG. 8 is a Table comparing the reactivity of lipidated OspC proteins C1 and C2 against sera from patients with the indicated condition with the reactivity of the unlipidated chimeric proteins of the present invention, where the number in parentheses is the total number of sera tested in that category.

DETAILED DESCRIPTION OF THE INVENTION

As described herein, initially nineteen groups of ospC from *B. burgdorferi* sensu stricto were found within a small tick population (Wang, I-N., et al., *Genetics,* 151:15-30 (1999)). Major ospC groups were defined using the observation that ospC alleles are either very similar, having less than 2% sequence divergence, or very different, having greater than 8% sequence divergence, with most having greater than 14% sequence divergence.

Based on sequence divergences, alleles of ospC can be grouped into twenty-one major groups (Table II). To assess whether strain differences as defined by a given ospC group are linked to invasiveness and pathogenicity, the frequency distributions of major ospC groups from ticks, from the primary erythema migrans (EM) skin lesion, and from secondary sites, principally from blood and spinal fluid, were compared. As described herein, the frequency distribution of ospC groups from ticks is significantly different from that of primary site infection which in turn is significantly different from secondary sites. The major ospC groups A, B, I and K increased in frequency from ticks to the primary site and were the only groups found in secondary sites of the infection. Therefore, three categories of major ospC croups are defined herein. One category is common in ticks but very rarely, if ever, causes human disease, a second category that causes only local infection at the tick bite site, and a third category that causes systemic or disseminated disease. While many ospC groups found in ticks were also found in primary skin lesions, the frequency distributions are significantly different between ticks and primary skin lesions (Table III). All ospC groups were found more or less commonly in ticks. However, only four groups are commonly found in skin lesions or secondary infections (Tables III and IV). As described herein, the primary skin lesions harbored *Borrelia* having ospC groups other than A, B, I or K rarely or not at all. More importantly, only these four ospC groups were found in secondary sites. The finding that all systemic *B. burgdorferi* sensu stricto infections are associated with four ospC groups has importance in the diagnosis, treatment and prevention of Lyme disease.

There is evidence that ospC has been transferred between strains and even between genospecies (Wang I-N. et al., *Genetics,* 151:15-30 (1998)). This is not true of *Borrelia* chromosomal genes (Dykhuizen, D. E., et al., *Proc. Natl. Acad. Sci.,* 30:10163-10167 (1999); Maynard Smith, J. and Smith, N. H., *Mol. Biol. Evol.,* 15:590-599 (1998)). However, ospA and ospC alleles in *B. burgdorferi* sensu stricto are almost completely linked (Wang I-N. et al., *Genetics,* 151:15-30 (1999)). This suggests that once an ospC allele has been transferred into a particular background, there is little or no selection for another similar recombination event. Thus, each major ospC group represents a clonal population descended from a single recombination.

Twenty percent of untreated erythema migrans clear spontaneously without causing any systemic complications (Steere, A. C. et al., *Arth. Rheum.* 20:7-17, (1977)). As demonstrated herein, this is not significantly different ($p=0.25$ for a 2 by 2 contingency test with double dichotomy) from the percent of non-invasive strains found in the skin, suggesting that the erythema migrans that clear spontaneously are caused by non-invasive clones.

There is extensive genetic and antigenic diversity of ospC in all three pathogenic genospecies of *B. burgdorferi* sensu lato (Livey, I. et al., *Mol. Microbiol.* 18:257-269, 1995; Masuzawa, T. et al., *Clin. Diagn. Lab. Immunol.* 4:60-63, 1997; Picken, R. N. et al., *J. Invest. Dermatol.* 110:211-214, 1998; Theisen, M. et at., *J. Clin. Microbiol.* 31:2570-2576, 1993; Wang, I-N. et al., *Genetics* 151:15-30 (1999). As demonstrated herein, only four groups of ospC alleles are linked to both infectivity and invasiveness, and that invasiveness is confined to a small number of ospC clones. It is clear that the ospA and ospC alleles are tightly linked even though they are on different plasmids (Wang, I-N. et at., *Genetics* 151:15-30 (1999)). If the invasiveness is caused by allelic variation at another locus, this variation is likely to be tightly linked to the ospC variation. Thus, ospC is a good marker for human pathogenicity and perhaps its determinator. These findings have important implications not only for our understanding of the pathogenesis of this disease but for its diagnosis and prevention.

Spirochetemia is a transient phenomenon, but is presumably key in seeding secondary skin sites, the heart, joints, and nervous system, where these *Borrelia* cause the secondary and tertiary clinical manifestations of Lyme disease. All four invasive groups of *Borrelia burgdorferi* were found in isolates from blood and CSF. The one joint isolate belonged to group A. However, it can be inferred that groups not found in the blood will not be found in the joints since most if not all dissemination of *Borrelia* to secondary sites is via blood.

Figure 1:
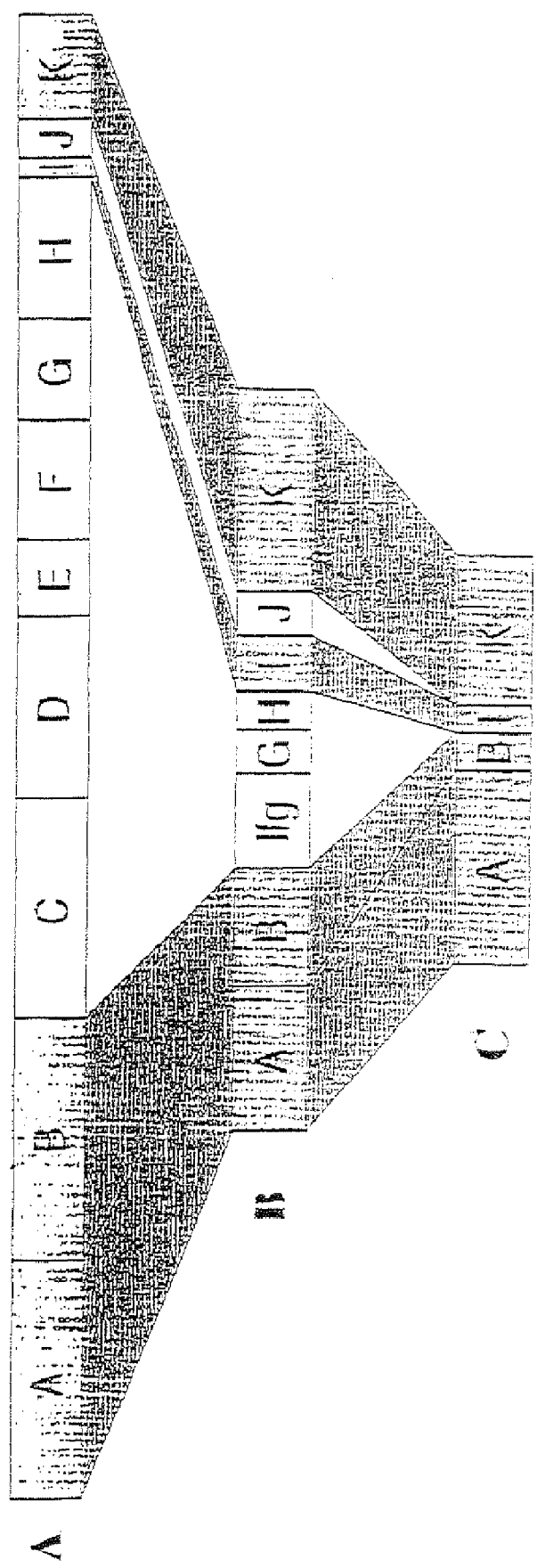

Normally, model organisms are used as substitutes for experiments on humans. However, this substitution works only as long as the properties of the model organism and of humans are the same for the studied phenomena. The human immune system plays a critical role which is expected to be different from the immune response in model organisms, particularly the mouse. Humans are accidental and usually dead-end hosts while the mouse is a critical host reservoir. The field of population genetics has developed sound procedures for reaching conclusions from survey data.

The chimeric polypeptides of the present invention elicit specific immune responses to OspC. The chimeric polypeptides also elicit immune response against strains of Lyme disease causing *Borrelia* of the same genospecies as that represented by the chimeric OspC as well as Lyme disease causing *Borrelia* of different genospecies than that represented by the chimeric OspC. The immune response includes humoral responses, secretory responses, cell-mediated responses and combinations thereof in an animal treated with the compositions of the present invention. The compositions of the present invention can include additional components suitable for in vitro and in vitro use. These additional components include buffers, carrier proteins, adjuvants, preservatives and combinations thereof.

The immunogenic compositions of the present invention can be used to immunize animals including humans. Immunization is understood to elicit specific immunogenic responses as described above. As described herein, an immunogenic response includes responses that result in at least some level of immunity in the treated animal, where the animal was treated with a composition comprising at least one protein or chimeric protein of the present invention. In one embodiment, the treated animal develops immunity against infection by Lyme disease causing *Borrelia*, wherein the chimeric proteins of the present invention elicit responses against *Borrelia burgdorferi, Borrelia afzelii* and *Borrelia garinii*.

Immunity, as described herein, is understood to mean the ability of the treated animal to resist infection, to resist systemic infection, to overcome infection such as systemic infection or to overcome infection such as systemic infection more easily or more quickly when compared to non-immunized or non-treated individuals. Immunity can also include an improved ability of the treated individual to sustain an infection with reduced or no clinical symptoms of systemic infection. The individual may be treated with the chimeric proteins of the present invention either proactively, e.g. once a year or maybe treated after sustaining a tick bite.

For use as a vaccine, the composition of the present invention can include suitable adjuvants, well known in the art, to enhance immunogenicity, potency or half-life of the chimeric proteins in the treated animal. Adjuvants and their use are well known in the art (see for example PCT Publication WO 96/40290, the entire teachings of which are incorporated herein by reference). The composition can be prepared by known methods of preparing vaccines. For example, the OspC proteins or chimeric proteins to be used in the compositions can be isolated and/or purified by known techniques such as by size exclusion chromatography, affinity chromatography, preparative electrophoresis, selective precipation or combinations thereof. The prepared proteins or chimeric proteins can be mixed with suitable other reagents as described above, where the chimeric protein is at a suitable concentration. The dosage of protein or chimeric protein will vary from one μg to 500 μg and depends upon the age, weight and/or physical condition of the animal to be treated. The optimal dosage can be determined by routine optimization techniques, using suitable animal models.

The composition to be used as a vaccine can be administered by any suitable technique. In one embodiment, administration is by injection, e.g. subcutaneous, intramuscular, intravenous, or intra peritoneal injection. In another embodiment, the composition is administered to mucosa, e.g. by exposing nasal mucosa to nose drops containing the proteins of chimeric proteins of the present invention. In another embodiment, the immunogenic composition is administered by oral administration. In another embodiment of the present invention the chimeric proteins are administered by DNA immunization.

Like many outer surface proteins of Borrelia, OspC is produced in the *Borrelia* spirochete with 5' lipidation. The chimeric polypeptides of the present invention can be produced in both lipidated and non-lipidated form. In one embodiment, the lipidation signal encoded by the wild type ospC is removed from the coding sequence, such that the gene or chimeric gene encodes a non-lipidated OspC or chimeric OspC polypeptide. In another embodiment of the present invention, the lipidation signal of the wild type ospC gene is replaced with the lipidation signal of the ospB gene. In this embodiment, a lipidated OspC or OspC chimeric protein is produced.

The polypeptides of the present invention can be recombinantly expressed in suitable microbial hosts, wherein said hosts include, but are not limited to, bacterial hosts, such as *E. coli*, fungal hosts *S. cerevisiae*, or cell culture hosts such as mammalian cell culture or insect cell culture.

While the lack of lipidation signal allows for the production of large amounts of OspC proteins and chimeric OspC proteins, the tack of lipidation signal was previously thought to render outer surface proteins of *Borrelia* less or non-immunogenic. However, as described herein, the non lipidated chimeric polypeptides of the present invention unexpectedly elicit as broad an immunogenicity as lipidated OspC protein (FIGS. 2 and 3) and greater immunogenicity against strains of other genospecies (FIG. 5-7) compared to the positive controls, which were lipidated OspC from B31 and lipidated OspC from C12.

The proteins and chimeric proteins of the present invention are also antigenic and therefore useful to detect or diagnose the presence of Lyme disease causing *Borrelia*, especially *Borrelia* from groups capable of causing disseminated symptoms of Lyme disease. As described herein, disseminated symptoms refers to infection outside of the erythema migrans skin lesion, e.g. infection in blood, CNS or synovia. As described herein, antigenic refers to the ability of a compound to bind products of an immune response, such as antibodies, T-cell receptors or both. Such responses can be measured using standard antibody detection assays, such as ELISA or standard T-cell activation assays.

The present invention is drawn to compositions comprising OspC polypeptides from Lyme disease causing *Borrelia* and chimeric OspC polypeptides. In one embodiment of the present invention, compositions include one or more OspC polypeptide or fragment thereof from at least two *Borrelia burgdorferi* ospC groups, referred also herein as families, selected from the group consisting of A, B, I and K, excepting the combination consisting of two OspC polypeptides from the A and I families. In another embodiment of the present invention, the compositions of the present invention include at least one OspC polypeptide or fragment thereof from each of *Borrelia burgdorferi* ospC families A, B, I and K. In another embodiment, the composition includes at least one OspC polypeptide or fragment thereof from each of *Borrelia*

*afzelii* OspC families A and B. In still another embodiment, the composition includes OspC polypeptides from at least one *Borrelia burgdorferi* OspC group or family member selected from the group consisting of A, B, I and K and at least one *Borrelia afzelii* OspC family member selected from the group consisting of A and B.

As described herein, the ospC families of the present invention share about 98% homology at the nucleic acid level between strains of the same family and share no more than about 92% homology at the nucleic acid level between strains of different families. Determination of homology, excludes any non-ospC sequences. Members of the same ospC family have similar antigenic profiles, e.g. elicit immune response against similar strains of Lyme disease causing *Borrelia*. The chimeric proteins of the present invention unexpectedly elicit immune response to Lyme disease causing *Borrelia* of different genospecies than the genospecies from which the component polypeptides were derived. In one embodiment of the present invention, *Borrelia burgdorferi* ospC family A comprises strains B31, CA4, HII, IPI, IP2, IP3, L5, PIF, PKA, TXGW and strains of *Borrelia* containing ospC allele OC1. In another embodiment of the present invention, *Borrelia burgdorferi* ospC family B comprises strains 35B808, 61BV3, BUR, DK7, PB3, ZS7 and strains containing ospC alleles OC2 and OC3. In still another embodiment of the present invention, *Borrelia burgdorferi* ospC family I comprises strains 297, HB19 and strains containing ospC allele OC10, wherein strain 297 is characterized by ospC of GenBank Accession No. L42893 (SEQ ID NO:85). In still another embodiment of the present invention, *Borrelia burgdorferi* ospC family K comprises strains 272, 297, 28354, KIPP, MUL and strains containing ospC allele OC12 and OC13, wherein strain 297 is characterized by ospC of GenBank Accession No. U08284 (SEQ ID NO:86).

In another embodiment of the present invention, said compositions comprise an OspC polypeptide or fragment thereof from each of *Borrelia afzelii* OspC families A and B. In one embodiment of the present invention, *Borrelia afzelii* OspC family A comprises strains Pbo, Pwud, Pko, Pgau, DK2, DK3, DK21, DK8, Bfox and JSB. In another embodiment of the present invention *Borrelia afzelii* OspC family B comprises strains DK5, ACA1, DK9, XB18h, Ple and 143M. As described above for *Borrelia burgdorferi* the compositions also include chimeric OspC polypeptides of *Borrelia afzelii* families A and B.

In one embodiment of the present invention, the OspC polypeptide OspC polypeptide is a chimeric OspC comprising at least one OspC protein variable region or portion thereof from at least one ospC gene. In one embodiment of the present invention, the OspC polypeptide variable region is encoded by a nucleic acid comprising the 3' two thirds of the OspC gene, about nucleotide 150 to about nucleotide 519 of an ospC gene (or about codon 50 to about codon 173). In another embodiment of the present invention, said OspC polypeptide variable region is encoded by a nucleic acid wherein the nucleic acid comprises, for example, nucleotide 244 to about nucleotide 519 (or about codon 81 to about codon 173), nucleic acid from about nucleotide 337 to about nucleotide 519 (or about codon 112 to about codon 173), nucleic acid from about nucleotide 418 to about nucleotide 519 (or about codon 139 to about codon 173), nucleic acid from about nucleotide 244 to about nucleotide 418 (or about codon 81 to about codon 139), nucleic acid from about nucleotide 337 to about nucleotide 418 (or about codon 112 to about codon 139), and nucleic acid from about nucleotide 150 to about nucleotide 243 (or about codon 50 to about codon 81) of an ospC gene.

In still another embodiment, the chimeric OspC polypeptides of the present invention comprises two or more polypeptides wherein a first polypeptide is from a first ospC gene from about nucleotide 26 (or about codon 8) to about nucleotide 630 (or about codon 210). In another embodiment, the first polypeptide is from about nucleotide 28. In another embodiment, the first polypeptide is from about nucleotide 53. In still another embodiment, the first polypeptide is from about nucleotide 55. In another embodiment, the first polypeptide is up to about nucleotide 621 of a first ospC gene. In still another embodiment, the first polypeptide is up to about nucleotide 582 of a first ospC gene. In still another embodiment, the first polypeptide is up to about nucleotide 576 of a first ospC gene.

The chimeric OspC of the present invention further comprises a second polypeptide, wherein the second polypeptide is derived from a second ospC gene from about nucleotide 28 (or about codon 9) to about nucleotide 571 (or about codon 190).

It is understood that the polypeptides than comprise the chimeric polypeptide can include extra nucleotides or fewer nucleotides from the given ospC gene from which the polypeptide is derived in order to simplify the construction of the gene encoding the chimeric polypeptide, e.g. to allow for the use of convenient restriction endonuclease sites or to allow the ligation of the gene fragments such that a contiguous coding region is created. Based on the guidance provided herein, one of ordinary skill in the art would readily be able to add or remove nucleotides from the termini of the gene fragments encoding the polypeptides of the chimeric OspC protein to generate chimeric proteins of the present invention with no or only routine experimentation. Furthermore, there can be an extra about 1 to about 10 amino acids on the N- and/or C-terminus of the polypeptides and chimeric proteins of the present invention and still retain the properties of the present invention.

The present invention also includes variants or altered versions of the OspC polypeptides and nucleic acids encoding said polypeptides. As used herein, a variant of a polynucleotide or polypeptide refers to a molecule that is substantially similar to either the entire molecule, or a fragment thereof. For example, when the molecule is a polypeptide, variant refers to an amino acid sequence that is altered by one or more amino acids, wherein either a biological function, structure or antigenicity of said sequence or combination thereof is maintained in the variant. The variant may have "conservative" changes, wherein a substituted amino acid has similar structural or chemical properties, e.g., replacement of leucine with isoleucine. Or a variant may have "nonconservative" changes, e.g., replacement of a glycine with a tryptophan. Similar minor variations may also include amino acid deletions or insertions, or both. Similarly. when the molecule is a polynucleotide, variant refers to a sequence that is altered by one or more nucleotides. The variant may have silent variations, wherein the change does not alter the amino acid encoded by the triplet comprising said variation or the variation is not silent, that is, alterations in encoded amino acids are generated.

As used herein, the term "altered version" refers to a polynucleotide sequence or a polypeptide sequence, wherein said sequence has one or more differences with a native or wild-type version of said sequence.

In another embodiment, the invention includes an isolated nucleic acid molecule comprising a nucleotide sequence which is homologous to one or more of the chimeric sequences of the present invention, or complements thereof. Such a nucleotide sequence exhibits at least about 80% homology, or sequence identify, with one of the chimeric OspC sequences, such that the encoded protein retains the antigenicity and immunogenicity of the unaltered chimeric protein. Preferably, the homologous sequences of the present invention shares at least about 90% homology or sequence identity with the corresponding unaltered chimeric ospC. Particularly preferred sequences have at least about 95% homology or have essentially the same sequence.

The altered nucleic acids and homologous nucleic acids of the present invention hybridize to the corresponding chimeric ospC under conditions of high stringency. A general description of stringency for hybridization conditions is provided by Ausubel, F. M., et al., Current Protocols in Molecular Biology, Greene Publishing Assoc. and Wiley-Interscience 1987, & Supp. 49, 2000. Factors such as probe length, base composition, percent mismatch between the hybridizing sequences, temperature and ionic strength influence the stability of nucleic acid hybrids. Thus, stringency conditions, sufficient to allow hybridization of oligonucleotides to the template, can be varied by routine optimization to generate high stringency conditions.

Alternatively, conditions for stringency are as described in WO 98/40404, the teachings of which are incorporated herein by reference. In particular, examples of highly stringent, stringent, reduced and least stringent conditions are provided in WO 98/40404 in the Table on page 36. Examples of stringency conditions are shown in Table I below which is from WO98/40404 to Jacobs et al.,: highly stringent conditions are those that are at least as stringent as, for example, conditions A-F; stringent conditions are at least as stringent as, for example. conditions G-L; and reduced stringency conditions are at least as stringent as, for example, conditions M-R.

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

†: SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete.

*$T_B$-$T_R$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)–4(# of G+C bases). For hybrids between 18 and 49 base pairs in length, $T_m$(° C.)=81.5+16.6($\log_{10}$[$Na^+$])+0.41 (%G+C)–(600/N), where N is the number of bases in the hybrid, and [$Na^+$] is the concentration of sodium ions in the hybridization buffer ([$Na^+$] for 1×SSC=0.165 M).

As used herein, "isolated" refers to nucleic acid or polypeptide that has been removed from its original environment (e.g., the natural environment if it is naturally occurring). For example, polynucleotide or DNA or polypeptide, which is separated from some or all of the coexisting materials in the natural system. An isolated polynucleotide can be part of a vector and/or composition, and still be isolated in that the vector or composition is not part of its natural environment. Likewise polypeptides can be part of a composition and still be isolated in that the composition is not part of its natural environment.

TABLE 1

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≥50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≥50 | 70° C.; 1xSSC -or- 50° C.; 1xSSC, 50% formaimde | 70° C.; 0.3xSSC |
| F | RNA:RNA | <50 | $T_F$*; 1xSSC | $T_F$*; 1xSSC |
| G | DNA:DNA | ≥50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≥50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≥50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≥50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≥50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≥50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

The chimeric proteins of the present invention comprise OspC proteins or polypeptides as described above from two or more OspC families of Lyme disease causing Borrelia as described in Table II. In one embodiment of the present invention, said families comprise Borrelia burgdorferi OspC families A, B, I and K and *Borrelia afzelii* OspC families A and B. The chimeric proteins of the present invention comprise, for example, a first OspC polypeptide encoded by a nucleic acid comprising a sequence from about codon 18 to about codon 210 of a first ospC gene. In another embodiment, the sequence is from about codon 8. In another embodiment, the sequence is to about codon 207. In another embodiment, the sequence is to about codon 194. In still another embodiment, the sequence is to about codon 192. The chimeric proteins of the present invention further comprise, for example, a second OspC polypeptide comprising an OspC variable polypeptide encoded by nucleic acid fragments as described above. In another embodiment of the present invention, the chimeric protein comprises two or more OspC variable polypeptides as described above.

The chimeric proteins of the present invention further comprise, for example, a second OspC polypeptide encoded by a nucleic acid comprising a sequence from about codon 9 to about codon 190 of a second ospC gene.

For the chimeric proteins of the present invention, at least two of said OspC polypeptides or immunogenic fragments thereof are fused together in a single protein, a chimeric protein, encoded by a single nucleic acid, wherein no two adjacent polypeptides in said fusion protein are found in the same configuration in a naturally occurring OspC protein.

In still another embodiment, the OspC proteins or chimeric proteins of the present invention from *Borrelia burgdorferi* and *Borrelia afzelii* are combined in a composition.

The present invention is drawn to a method of detecting an immune response to Lyme Disease causing *Borrelia* in a host sample. The method comprises contacting the host sample with a composition comprising OspC polypeptides from Lyme disease causing strains of *Borrelia*, such that anti-OspC antibodies, if present, in said sample bind to said OspC polypeptides. In one embodiment, the composition comprises one or more OspC polypeptide or diagnostic fragment thereof from two *Borrelia burgdorferi* OspC families selected from the group consisting of A, B, I and K, excluding the composition consisting of two OspC proteins wherein one OspC protein is from OspC family A and the second OspC protein is from OspC family I. The antibodies that bind the OspC polypeptides of the composition are detected or measured; thereby detecting an immune response to Lyme disease causing *Borrelia*. In another embodiment, the composition comprises at least two *Borrelia* OspC polypeptides or diagnostic fragment thereof from two *Borrelia afzelii* OspC families selected from the group consisting of A and B. In still another embodiment, the composition comprises polypeptides from OspC from *Borrelia burgdorferi* and *Borrelia afzelii*. In still another embodiment, the composition comprises one or more polypeptides from each of *Borrelia burgdorferi* families A, B, I and K and *Borrelia afzelii* families A and B. The composition can also comprise one or more of the chimeric polypeptides of the present invention.

The present invention is also drawn to kits comprising one or more OspC polypeptides or OspC chimeric polypeptides or combinations thereof together with suitable buffers and antibody detection reagents for the detection or diagnosis of Lyme disease causing strain of *Borrelia*. In another embodiment, the kits comprise nucleic acid sufficiently homologous to the OspC polypeptides or OspC chimeric polypeptides to detect nucleic acid encoding ospC genes from Lyme disease causing strains of *Borrelia* together with reagents to detect positive hybridization to target DNA or reagents to specifically DNA, for example.

For the purposes of a detection kit, "homologous" refers to two or more sequences that share substantial similarity but are not identical. Two DNA sequences are "substantially similar" when at least about 95% (preferably at least about 98%) of the nucleotides match over a defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See. e.g., Ausubel et al., *Current Protocols in Molecular Biology*, John Wiley & Sons, Inc., New York; Sambrook et al., *Molecular Cloning: A Laboratory Manual*, Cold Spring Harbor Laboratory Press. For purposes of the present invention, amino acid sequences having, for example, greater than 90 percent similarity are considered substantially homologous.

The vaccine compositions of the present invention elicit humoral and cell mediated immune responses in a host. Furthermore, the diagnostic compositions of the present invention are capable of detecting both humoral and cell mediated immune response from a host sample using standard immunodiagnostic techniques.

EXEMPLIFICATION

Example 1

Techniques

*Borrelia* Strains

One hundred and forty *B. burgdorferi* strains were isolated from primary erythema migrans (EM) lesions, blood or cerebrospinal fluid (CSF) of patients seen at the Lyme Disease Center at Stony Brook, N.Y., Lyme Disease Diagnostic Center at New York Medical College, Valhalla, N.Y. or the private practices of the two collaborating physicians on the eastern end of Long Island or were obtained from the Centers for Disease Control (CDC). All patients met the Centers for Disease Control surveillance definition for Lyme Disease (CDC, *Morb. Mortal. Wkly. Rep* 46:20-21, (1997)). Isolates from skin, blood and CSF were obtained using standard techniques (Barbour, A. G., *Yale J. Biol. Med.* 57:521-525, 1984; Berger, B. W. et al., *J. Clin. Microbiol.* 30:359-361, 1992; Wormser, G. P. et al., *J. Clin. Microbiol.* 36:296-298, (1998)). Punch biopsies were taken from the advancing border of the erythema migrans lesion and incubated in BSK-H medium (Sigma, St. Louis, Mo.) at 34° C. to create a culture. There was little culture bias as determined by direct analysis of biopsy tissue compared to culture isolates (Seinost, G. et al., *Arch. Derm.*, 135:1329-1333, (1999)), unlike isolation of *B. burgdorferi* from unfed ticks (Norris, D. E. et al., *J. Clin. Microbiol.* 35:2359-2364, (1997)). In addition, twenty-two *B. burgdorferi* sensu stricto ospC sequences were retrieved from GenBank. The tick data used was either from GenBank or from the study of Wang et al. (Wang, I-N. et al., *Genetics* 151:15-30 (1999)).

DNA Isolation

For isolation of genomic *Borrelia* DNA, log phase cells were harvested by centrifugation at 10,000 RPM for 30 minutes at 4° C. The bacterial pellet was resuspended in Tris/saline-buffer (10 mM Tris (pH 7.5), 150 mM NaCl). The bacteria were then pelleted and resuspended in TNE (10 mM Tris (pH 7.5) 150 mM NaCl, 1 mM EDTA). Freshly prepared lysozyme (20 mg/ml in TNE), sodium dodecyl sulfate (10%) and proteinase K (20 mg/ml) were added and the mixture was incubated at 50° C. for one hour, followed by RNAse treatment. DNA was extracted with phenol/chloroform, precipitated with ethanol and resuspended in TE buffer.

Polymerase Chain Reaction

The ospC gene was amplified using PCR, as described previously (Wang, I-N. et al., *Genetics* 151:15-30 (1999)). The OspC gene was amplified using two external primers: 5'-AAA GAA TAC ATT AAG TGC GAT ATT-3' (+), SEQ ID NO: 1, beginning at base 6; and 5'-GGG CTT GTA AGC TCT TTA ACT G-3' (−), SEQ ID NO: 4, ending at base 602. The 5' half of ospC was amplified using SEQ ID NO: 1 and the reverse primer, 5'-CAA TCC ACT TAA TTT TTG TGT TAT TAG-3' (−) SEQ ID NO: 2; ending at base 345. The 3' half of ospC was amplified using the primer, 5'-TTG TTA GCA GGA GCT TAT GCA ATA TC-3' (+), SEQ ID NO: 3, beginning at base 289, and SEQ ID NO: 4 as the reverse primer. The external primers amplified a 597 bp fragment. Amplification of the 5' half produced a 340 bp fragment while amplification of the 3' half produced a 314 bp fragment. All the base numbers and amplified fragment sizes are based on ospC sequence of strain B31 (GenBank accession number U01894), with start codon as base 1.

Amplification was conducted in 50 µl of a solution containing Perkin-Elmer Cetus 10× PCR buffer (100 mM Tris-HCl (pH 8.3), 500 mM KCl), 2.5 mM $MgCl_2$, deoxynucleoside triphosphates at 0.2 mM per nucleotide, 2.5 U of Taq polymerase (Perkin-Elmer/Cetus) and 0.5 µM of each primer. The amplification reaction was carried out for forty cycles in a DNA thermal-cycler (PTC-100; MJ Research, Inc., Watertown, Mass.) with an amplification profile of: denaturation at 95° C. for 40 seconds, annealing at 54° C. for 35 seconds, and extension at 72° C. for 1 min. after an initial denaturation step at 96° C. for 2 min. Negative controls were included in each experiment to control for contamination.

Cold SSCP-analysis.

SSCP analysis was chosen to characterize genetic variation of the isolated ospC gene fragments based on its exquisitely high detection rate of DNA polymorphisms and point mutations at a variety of positions in DNA fragments (Orita, M. et al., *Proc. Natl. Acad. Sci.* 862766-2770, (1989)). Single point mutations have been detected in fragments up to 800 bp long (Michaud, J. et al., *Genomics*, 13:389-394, (1992)). However, there is evidence that the ability of SSCP analysis to detect mutations begins to decline significantly as PCR fragments approach 400 bp in size (Hayashi, K., *PCR Methods & Applications* 1:34-38, (1991)). Therefore, in order to achieve high efficiency of detection of nucleotide polymorphism, the length of the PCR products used herein was 340 bp from the 5' half and 314 bp from the 3' half of ospC.

Amplified ospC gene fragments from all one hundred and forty strains were analyzed for genetic variations by the cold SSCP protocol described by Hongyo et al. (Hongyo, T. et al., *Nucleic Acids Res.* 21:3637-3642, (1993)). Briefly, 5 to 15 µl of the PCR product was added to a mixture containing 4 µl 5× TBE Ficoll sample Buffer (NOVEX, San Diego, Calif.) and 0.4 µl 1 µM methylmercury hydroxide (Alfa Aesaer, Ward Hill, Mass.). The amount of the PCR product used for the SSCP analysis was estimated after visualizing the PCR product on an agarose gel with ethidium bromide. The sample mixture was heated to 95° C. for 4 min, then chilled on ice prior to loading the entire 20 µl into the gel sample well. The sharpest bands were observed when the sample was applied to a pre-cast 20% TBE gel (NOVEX) electrophoresis system (ThermoFlow ETC Unit, NOVEX) with 1.25× TBE running buffer. Electrophoresis of SSCP products was conducted at a constant temperature of 8° C. for 17 h at 240 volts in order to reveal discernable mobility shifts. Gels were stained with 0.5 µl/ml ethidium bromide in 1× TBE buffer for 25 min and destained in distilled water for 30 min. Stained bands were viewed using a 340 nm UV staining box. Samples that showed more than two SSCP bands were reamplified to determine whether the bands found were real alleles or the product of PCR artifacts. Side-by-side SSCP analysis was performed in order to detect even slight shifts in electrophoretic mobility.

DNA Sequencing

The ospC gene or representatives of each mobility class were reamplified. Double-stranded PCR fragments were purified by agarose gel electrophoresis and subjected to automated DNA sequencing using fluorescent dideoxy terminator chemistry and the forward and reverse primers originally used for PCR amplification.

Statistical Analysis

Chi square analysis of contingency tables was performed. This analysis tests for significant difference in frequency distributions. The tables were 2×N where N is the number of major ospC groups distinguished. The average expected number in each element of the table needs to be about six or greater for an unbiased test (Zar, J. H., *Biostatistical Analysis*, 3rd ed, p. 206, (1996)). This means that the number of observations should be greater than 6 times 2N. When the expected average number was less than six, the major ospC groups with the lowest number in the sample were combined until the number of observations were about equal to or greater than 12N.

RESULTS ospC Mobility Classes in Human *B. burgdorferi* Isolates.

One hundred and thirty-two isolates of *B. burgdorferi* sensu stricto from patient samples of skin, blood, and CSF (Table II) were propagated in vitro and used as a source of DNA for analysis. The ospC genotype of each strain was determined by cold SSCP analysis of the 5' end (340 bp) of the gene and was confirmed by SSCP analysis of the 3' end (314 bp) of ospC. In all *B. burgdorferi* isolates, the genetic variation at the 5' end of the gene corresponded to the variation at the 3' end. At least two representatives of each SSCP mobility class were subsequently sequenced. The sequences of the same mobility classes were identical in all samples and each mobility class had a unique sequence. Therefore, the sensitivity and specificity of SSCP analysis was 100%. Each SSCP mobility class was designated as an allele. Wang et al, recently described 13 ospC alleles (Wang, I-N. et al., *Genetics* 151:15-30). An additional five ospC (OC) mobility classes, OC14-18 are described herein. OC14 has the same ospC sequence as the ospC in strain 2591.

TABLE II

Alignment of major ospC groups with ospC alleles identified by SSCP analysis

| Major ospC Group | ospC allele (SSCP) | GenBank number[1] | Ticks | Skin[2] | Disseminated[2] |
|---|---|---|---|---|---|
| A | 1 | AF029860 | 17 | 23 | 21 |
| B | 2 | AF029861 | 17 | 19 | 4 |
| C | 3 | AF029862 | 11 | 3 | 0 |
| D | 4 | AF029863 | 10 | 1 | 0 |
| E | 5, 7 | AF029864 | 6 | 1 | 0 |
| F | 6 | AF029865 | 9 | 0 | 0 |
| G | 8 | AF029867 | 5 | 7 | 0 |
| H | 9 | AF029868 | 7 | 6 | 0 |
| I | 10 | AF029869 | 1 | 9 | 3 |
| J | 11, 18 | AF029870 | 3 | 7 | 0 |

TABLE II-continued

Alignment of major ospC groups with ospC alleles identified by SSCP analysis

| Major ospC Group | ospC allele (SSCP) | GenBank number[1] | Ticks | Skin[2] | Disseminated[2] |
|---|---|---|---|---|---|
| K | 12, 13 | AF029871 | 6 | 32 | 16 |
| L | — | L42899 | 2 | 0 | 0 |
| M | 14 | U01892 | 1 | 3 | 0 |
| N | 15 | L42899 | 1 | 3 | 0 |
| O | — | X84778 | 0 | 1 | 0 |
| P | — | U91796 | 1 | 0 | 0 |
| Q | — | U91790 | 1 | 0 | 0 |
| R | — | U91791 | 2 | 0 | 0 |
| S | — | U91793 | 1 | 0 | 0 |
| T | 16 | AF065143 | 0 | 1 | 0 |
| U | 17 | AF065144 | 0 | 2 | 0 |

[1] A single GenBank sequence of each type is given as an example.
[2] The number of each major ospC group observed in blood, synovial fluid or cerebrospinal fluid. This includes both SSCP data and data from the literature, including GenBank.
*B. burgdorferi sensu stricto Groups P through S are only found in Europe. Groups R and S are excluded from the analysis because nearly identical ospC alleles are found in B. afzelii and B. garinii, showing these groups were recently created by cross-species transfer.

Multiple Infections

Of the one hundred and thirty-two primary isolates from patients with Lyme disease in this study, most contained only a single strain. Seven skin isolates and one CSF isolate contained two different strains as determined by SSCP analysis, thus giving a total of one hundred and forty different strains. The ospC allele pairs found in multiply infected erythema migrans biopsy specimens were (OC1, OC12), (OC1, OC14), 2×(OC2, OC3), 2×(OC2, OC12), and (OC8, OC18). CSF isolate NY940657 contained ospC alleles OC1 and OC12. For CSF isolate 297, which was isolated in Connecticut, there were two ospC sequences published in GenBank: L42893 (SEQ ID NO:85), which is analogous to OC10 and U08284 (SEQ ID NO:86), which is analogous to OC12. The pair-wise difference of ospC sequences of both strains is 16.4%, suggesting CNS infection with two different strains in this isolate. Overall, 5.5% of all isolates described herein contained two strains. Because as many as 50% of ticks isolated in the wild are infected with multiple strains, exposure to multiple strains in a single tick bite is common, raising the possibility that different strains are differentially pathogenic.

To these one hundred forty strains for which the ospC allele was determined herein, twenty-two strains of known ospC sequence from GenBank were added to give a total of one hundred sixty-two. Fifty-one of these strains were obtained either from eastern Long Island; seventy-seven were obtained from Westchester County, N.Y., and the remainder from other endemic areas in the United States (twenty-two strains) and Europe (twelve strains). The isolates were divided into those from the site of the primary infection, the erythema migrans skin lesion (one hundred eighteen isolates), and those from secondary sites, where the infection had disseminated (forty-four isolates). This later group included, for example, twenty from cerebro-spinal fluid (CSF), twenty-three from blood, and one from synovial fluid.

Major ospC Groups in Human *B. burgdorferi* Isolates

Surprisingly, as described herein, the differences between ospC sequences among and between the families of *B. burgdorferi* sensu stricto fell into two groups. Pairs of ospC genes within the same family differed in nucleic acid sequence by less than two percent while pairs of ospC genes from separate families in nucleic acid sequence differed by more than eight percent. Wang et al., defined nineteen major ospC groups, designated A to S (Wang, I-N. et al., *Genetics* 151:15-30 (1999)). As described herein, two additional ospC groups are provided, designated T and U. OC16 represents major group T and OC17 represents major group U (Table I). The lowest pair-wise differences of group T and U to any other major ospC group are 16.1% and 20.5% respectively.

*B. burgdorferi* Clones are Differentially Pathogenic

As described herein, clones representing different ospC groups of *Borrelia burgdorferi* are differentially pathogenic. This is demonstrated by the differing frequencies of the various major ospC groups in ticks, in the initial infection in the skin, and in disseminated infections.

The strains in GenBank and the literature for which the ospC sequences have been determined were widely sampled from the entire geographic range of the species and were chosen irrespective of whether they were from ticks or humans. These strains gave a small but random sample of the frequencies of the major ospC groups in ticks and humans. As demonstrated herein, the frequency of the major ospC groups from human isolates was found to be significantly different from the frequency found in ticks on Long Island. Table III shows that the frequency distribution of strains from skin from eastern Long Island differ significantly from tick strains collected in the same area

TABLE III

| | Major ospC groups | | | | | | | | | |
|---|---|---|---|---|---|---|---|---|---|---|
| Isolates From | A | B | C | D | F | G | H | I | K | Comb.[a] |
| Erythema migrans lesions (N = 46) | 13 | 6 | 2 | 0 | 0 | 1 | 0 | 4 | 16 | 4 |
| Ixodes scapularis ticks (N = 74) | 12 | 12 | 11 | 9 | 6 | 5 | 7 | 1 | 5 | 6 |

$\chi^2 = 36.3$ with 9 degrees of freedom
$p < 0.001$
[a] Combined major groups are defined by individual frequencies of 0.025 or less and include groups E, J, N, O.

The analysis provided herein of all ospC groups presented in this study showed that most groups are found in both ticks and in humans (Table II). However, major groups A, B, I and K predominated in humans with A and K groups found most frequently. (FIG. 1).

The pattern of pathogenicity of the various clones as demonstrated by frequency in the primary site of infection, the skin, compared to the frequency in secondary sites revealed that only four major groups (A, B, I and K) were found in both the skin and secondary sites (compare Tables III an IV). All other major groups were found only in the skin. When all groups with three or fewer isolates are combined to give the combined group of Table IV, a 2 by 8 contingency test comparing the frequency distribution of skin versus secondary sites gives a significance of $p<0.005$. When no groups are combined, a 2 by 15 contingency test is still significant ($\chi^2=24.07$ with 14 degrees of freedom, $p<0.05$). The distribution of strains from primary and secondary sites indicated that only a certain of the major groups, A, B, I, and K cause disseminated disease. As described herein, these are referred to as invasive clones whereas other clones are referred to as non-invasive clones.

TABLE IV

| Isolates From | Major ospC groups | | | | | | | |
|---|---|---|---|---|---|---|---|---|
| | A | B | G | H | I | J | K | Comb.[a] |
| Erythema migrans lesions (N = 118) | 23 | 19 | 7 | 6 | 9 | 7 | 32 | 16 |
| Disseminated Infections (N = 44) | 21 | 4 | 0 | 0 | 3 | 0 | 16 | 0 |

$\chi^2$ = 23.6 with 7 degrees of freedom
p < 0.005
[a]Combined major groups are defined by individual frequencies of 0.025 or less and include groups C, D, E, M, N, O, T and U.

As described herein, the different clones of *B. burgdorferi* sensu stricto, as defined by ospC groups, are differentially pathogenic. Some groups very rarely, if ever, cause human disease, e.g. ospC groups D, E, F, and L. Some groups cause a local infection at the tick bite site, but not systemic disease, e.g. ospC groups G, H, J, and T. Finally, there are some groups which are responsible for systemic disease; these are ospC groups A, B, I, and K. Our findings indicate that all systemic *B. burgdorferi* sensu stricto infections in humans are caused by strains in these four ospC groups.

FIG. 1 shows the frequency distribution of major ospC groups among *B. burgdorferi* isolates from Eastern Long Island *Ixodes scapularis* ticks, n=72, (A); erythema migrans lesions, n=118, (B); and secondary sites of infection, n=44, (C). The percentage of group A plus K increased from 23% in the tick isolates, to 47% in the skin isolates, and to 84% in the secondary sites. The length of the bars in FIG. 1 reflect this increase, by holding the length of the combined A and K groups constant. In the skin, groups C, D, E, M, N, O, T and U have been combined since their individual frequencies are 0.025 or less. This combination of groups when combined make up 12.7% of the total number of strains.

A similar analysis was conducted for *Borrelia afzelii*. The analysis included OspC alleles from 21 strains from GenBank and 12 strains sequenced for this study. These sequences fell into 20 major groups where the definition of a group is less that 1% sequence diversity within a group and at least 7.7% sequence difference between groups. There were two exceptions to this rule which were caused by a deletion in one ospC gene and a cross-species transfer of a small section of DNA in another ospC gene. When these anomalous sections were removed, all ospC alleles fell into 20 groups. Only two groups contained strains from chronic infections—groups A and B. By analogy and the *B. burgdorferi* study, it appears that only two groups are pathogenic in *B. afzelii*.

Example 2

Protein Expression and Immunoblot

Protein Expression

The *Escherichia coli* (strain BL21 (pLysS) or strain B834 (DE3)) were transformed with the plasmid encoding the recombinant chimeric *Borrelia* proteins (RCBPs), and grown in 10 ml LB media (5 g/l NaCl, 10 g/l tryptone, 5 g/l yeast extract, 25 mg/l chloramphenicol and 50 mg/l ampicillin) at 37° C., with shaking. When the optical density at 600 λ reached 0.3-0.4 units, recombinant protein expression was induced by adding IPTG (isopropyl B-D-thiogalactopyranoside) to a final concentration of 0.5 mM and the cells were grown for an additional three hours. The cultures were harvested by centrifugation at 3800×g for five minutes. The cells were resuspended in 20 mM $NaPO_4$, pH 7.7 and stored at –20° C. overnight. Once thawed, the crude extracts were incubated with DNase (2 µg/ml) in the presence of 2.5 mM of $MgCl_2$ at room temperature for thirty minutes, spun at 14000 rpm (Eppendorf 5417C) for five minutes and 5 µl of the protein sample was run on a SDS-PAGE which was either stained in Commassie Blue or used for Immunoblot. Protein samples were solubilized, usually with a sodium dodecyl sulphate (SDS) containing buffer and in selected cases with reducing agents such as dithiothreitol (DTT) or 2-mercaptoethanol (2-ME). Following solubilization, the material was separated by SDS-PAGE. The proteins were then eletrophoretically transferred to a polyvinylidene difluoride membrane (PVDF, Immobilon-P®, Millipore). The transfer of proteins was monitored by a reversible staining procedure, Ponceau S. The stained membrane was made and the membrane destained by soaking in water for 10 minutes. All non-specific binding sites in the proteins and on the membrane were blocked by immersing the membrane in a solution containing a protein or detergent blocking agent (5% milk in tris-buffered saline (TBS) Tween-20® 0.1%). The membranes were then incubated with primary antibody (either a monoclonal antibody or Erythema Migrans Lyme disease human serum). The membrane was washed and the antibody-antigen complexes were identified using alkaline phosphatase (AP) enzymes coupled to secondary antibody, either anti-immunoglobulin G (anti-mouse IgG) to detect the monoclonal antibody or anti-human IgA+IgG+IgM to detect the serum antibodies. A chromogenic substrate for alkaline phosphatase was then used to visualize the activity.

Example 3

Serologic Characterization—ELISA (Enzyme-Linked Immunosorbent Assay)

Immobilization of RCBPs onto ELISA Plates, Determining Optimal RCBP Binding:

A solution of purified RCBPs in sodium phosphate buffer, pH 9.0 was used to coat commercial microwell plates (MaxiSorp®, Nunc). Recombinant OspC *Borrelia* proteins ale described in Table V. Th e coating procedure was as follows: 100 µl of a solution containing the appropriate concentration of each RCBP was added to each well and the microwell plate was incubated for either one hour at room temperature or at 4° C. overnight. The antigen solution was removed from the wells, the plate washed three times with phosphate buffered saline (PBS) pH 9.0, and 200 µl of blocking solution added (2% BSA fraction V (Sigma) in PBS). Following a thirty minute incubation at 37° C., the plates were washed three times with PBS, wrapped in plastic and stored at 4° C. until used. The binding of the individual RCBPs was measured using monoclonal antibodies specific for either OspA or OspC followed (after washing) by an alkaline phosphatase-conjugated goat anti-mouse secondary antibody. The upper limit of protein binding was found to be beyond the working range of the monoclonal antibody used to measure it, and the standard blocking protocol was found to successfully saturate this high protein binding capacity, leaving low background readings in the control wells. The results of these experiments indicated that a protein concentration of 0.5 µg/ml in the coating buffer was optimal for each of the RCBP tested. It was not found to be necessary that the chimeric proteins be immobilized in a specific molar ratio to one another; only that enough of each protein be bound so that epitopes in that chimeric protein do not become limiting in subsequent ELISA assays using patient serum. For practical purposes, it was found that these conditions were met when the monoclonal-capture assay reached an absorbance of about 1.5 units or greater for each mouse monoclonal antibody with a specific epitope represented in one of the chimeric proteins on the well surface. If necessary, however, the concentrations of individual proteins in the mixture can be adjusted to achieve the desired levels of immobilized protein using routine optimization. Although the amount of each RCBP bound to the surface of the well and the amount of any one epitope exposed to the solution varies somewhat from protein to protein, the amount of bound epitope was not found to be limiting within the useful range of the ELISA.

ELISA Tests:

The standard procedure for the ELISA tests was as follows: human serum samples were diluted 1:100 in specimen diluent (10% fetal bovine serum in PBS pH 9.0) and 100 µl of each sample added to ELISA plate microwells that had been coated with antigen as described above. Following incubation for 1 hour at 37° C., the samples were removed and the plates washed three times in TBS-Tween™ (0.5 M Tris pH 7.2; 1.5 M NaCl; 0.5% Tween™). Coat anti-human antisera conjugated to alkaline phosphatase specific for either IgM (Fe) or IgG (Fab), (Jackson Immuno Research Laboratories) was diluted 1:1000 in PBS, pH 7.4 and 100 µl of the solution added to each well. Following incubation for thirty minutes at 37° C., the plates were washed three times with TBS-Tween™ and 100 µl of substrate solution (5 mg of p-nitrophenylphosphate tablets dissolved in 1× diethanolamine substrate buffer to yield a 2 mg/ml solution—Kirkegaard Perry Laboratory) was added to each well. The plates were incubated for thirty minutes at 37° C. and 100 µl of stop solution (5% EDTA) was added to each well. The absorbance at 410 nm was read on a microplate reader (Dynatech). A sample was considered positive if it produced an average absorbance greater than the mean of the negative controls plus three standard deviations, Cross-reactivity was measured against serum from patients with syphilis, systemic lupus erythematosus, rheumatoid arthritis as well as endemic field workers and non-endemic field worker.

Using the above-described ELISA test, serum from various patients was tested. Patients with Erythema Migrans Acute (EMA) had early, localized infections, typified by the presence of well-defined erythema migrans (EM) in patients from an endemic area.

Patients with Early Disseminated (EA), are Acute Disseminated (AcD) infections were typified by EM and one of the following: additional EM lesions, AV block, neurological abnormalities (e.g., seventh nerve pasly), or meningitis. Patients with Acute Convalescent (AcC) were obtained from the same patients as EA and AcD, 2-4 weeks later. Serum was also tested from the CDC from patients with well documented Syphilis (S), serum was also obtained from SUNY at Stony Brook, Division of Rheumatology from patients with well documented systemic Lupus Erythematosus (SLE) or patients with well documented Rheumatoid Arthritis (RA). Endemic field worker sera (End), were obtained from outdoor workers from Long Island, which is endemic for Lyme disease. Non-endemic sera (Nedn) were obtained from outdoor workers from Arizona, which is not endemic for Lyme disease. In addition, serum was tested from endemic field workers (End) and non-endemic field workers (NEnd). Polypeptides of the present invention were used to test these various sera as summarized in FIG. 8.

TABLE V

| Polypeptide | SEQ ID NO.:* (DNA) | SEQ ID NO: (POLYPEPTIDE) |
|---|---|---|
| C2 unlipidated | 5 | 6 |
| C5 unlipidated | 7 | 8 |
| [1]C1 | 9 | 10 |
| C2 | 11 | 12 |
| C5 | 13 | 14 |
| C7 | 15 | 16 |
| C10 | 17 | 18 |
| C11 | 19 | 20 |
| C12 | 21 | 22 |
| C1C10[2] | 23 | 24 |
| C1C12 | 25 | 26 |
| B31C10[3] | 27 | 28 |
| B31C12 | 29 | 30 |
| C2C7 | 31 | 32 |
| C2C10 | 33 | 34 |
| C2C12 | 35 | 36 |
| C5C7 | 37 | 38 |
| C5C10 | 39 | 40 |
| C5C12 | 41 | 42 |

[1]C1-C12 are OspC genes/proteins with lipidation signal.
[2]C2C10 and other compound C names refer to chimeric OspC proteins wherein the N-terminal portion of the chimera is derived from a first ospC allele and the C-terminal portion of the chimeric molecule is derived from second ospC allele, as described herein. The polypeptides were not lipidated.

Example 4

Mice Immunization with OspC Chimeric Proteins as Immunogen

Female BALB/c mice, four-five weeks old, were immunized with 5 µg of OspC chimeric proteins in 100 µl of aluminum hydroxide adjuvant by SC (subcutaneous) injection. Five mice were used for each group. For the negative control, five female BALB/c mice were immunized with 100 µl of aluminum hydroxide adjuvant only. Two weeks after immunization, the mice received a boost with the same antigen and two weeks after that an equal boost was administered. One week after each boost, blood was drawn from each mouse (including negative controls) and the serum was tested, using the ELISA method described above, for the presence of the respective anti-OspC chimeric protein antibodies.

Mice were immunized with chimeric proteins as follows in Table VI.

TABLE VI

| Immunogen | SEQIDNO.: (polypeptide) | OspC Family |
|---|---|---|
| LipCB31[1] | 44 (DNA 43) | A |
| LipC12[2] | 22 (DNA 21) | K |
| UnlipC2[3] | 8 | B |
| UnlipC2C7[4] | 32 | B/E |
| UnlipC2C10 | 34 | B/I |
| UnlipC2C12 | 36 | B/K |
| UnlipC5C10 | 40 | E/I |
| UnlipC5C12 | 42 | E/K |

[1]"Lip" means lipidated N-terminus, Lip CB31 is OspC protein from *B. burgdorferi* strain B31.
[2]The number immediately after "C" refers to the particular allele of OspC as described herein.
[3]"Unlip" means the unlipidated form of the N-terminus.

Figure 2:
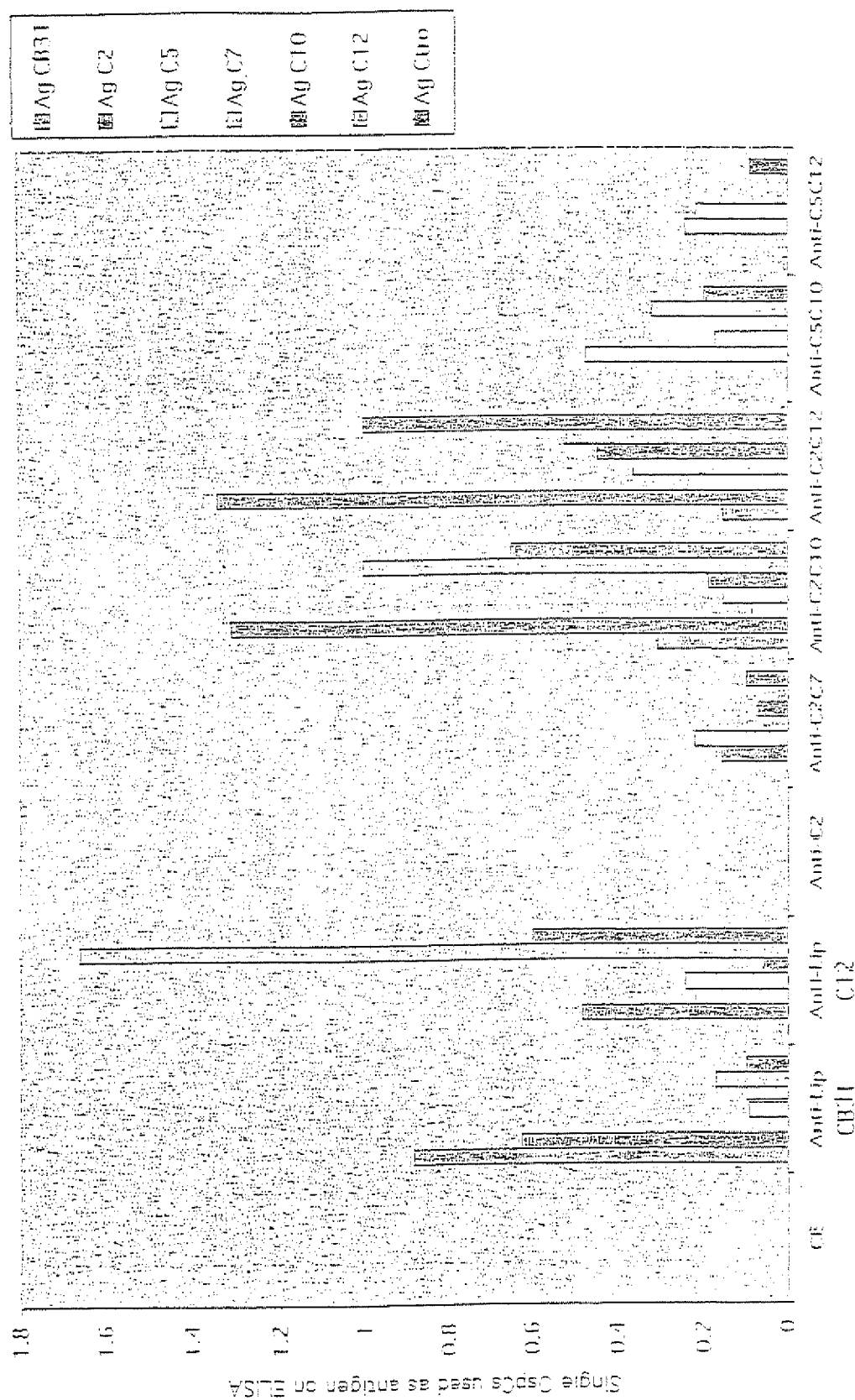
Figure 3:
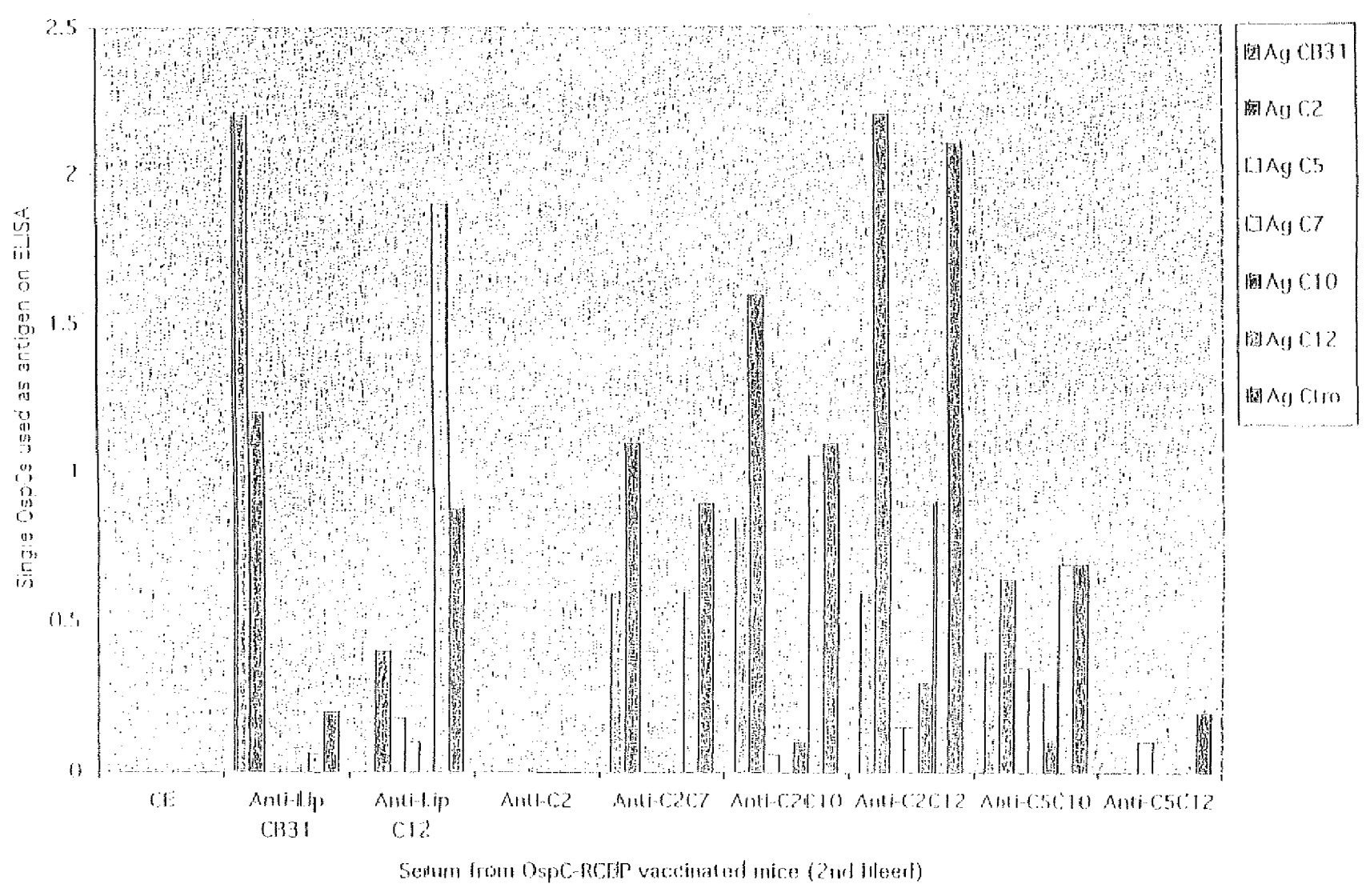

Several types of single OspCs from *B. burgdorferi* sensu stricto, OspCB31, OspC2, OspC5, OspC7, OspC10, OspC12 and a single OspC from *B. afzelii*, Ctro, were used as the antigens in an ELISA to test the serum collected from the immunized mice. As shown in FIGS. 2 and 3, unlipC2C10 and unlipC2C12 elicited an immune response in the form of antibodies, (a humoral response) against a broad range of ospC families, after the first and second bleeds, respectively. The serum from unlipC2C10, unlipC2C12, LipCB31 and LipC12 immunized mice was then used to test against single OspC polypeptides from several strains of the three major Borrelia gene species Borrelia burgdorferi, Borrelia afzelii and Borrelia garinii.

Figure 4:
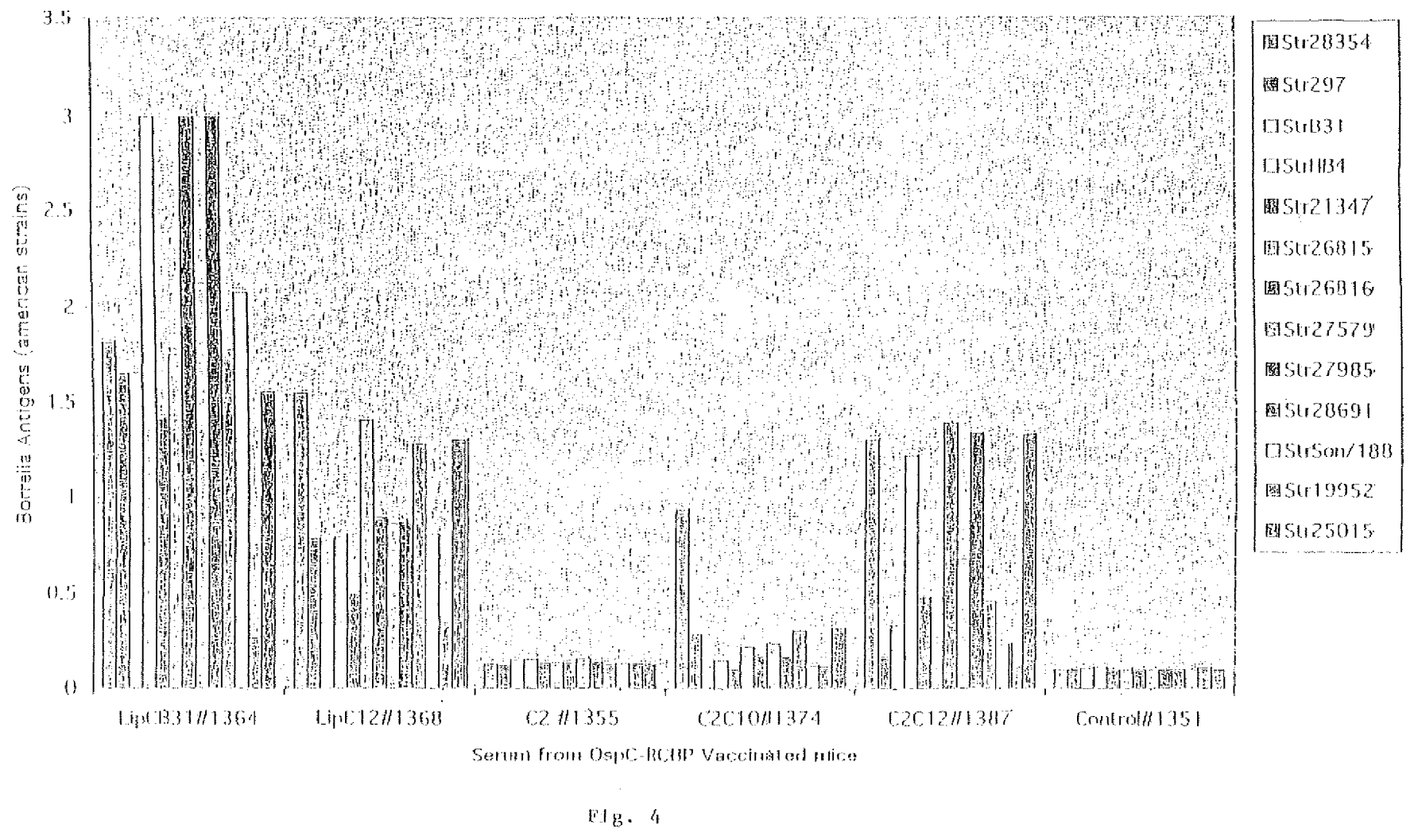

As shown in FIG. 4, 13 different strains of B. burgdorferi sensu stricto (B.b.s.s.) were tested for reactivity with the above described sera. Sera from mice immunized with both LipCB31 and LipC12, which were the gold standard of this experiment, detected 12/13 of the B.b.s.s. strains tested. Sera from mice immunized with unlipidated C2C12 detected 8/13 of the strains tested. Use of unlipidated forms of these proteins as vaccine immunogens or diagnostic antigens is desirable because the product yield by the expression vector is much greater and the proteins are much easier to purify. These two reasons alone made the production of these proteins less expensive.

Figure 5:
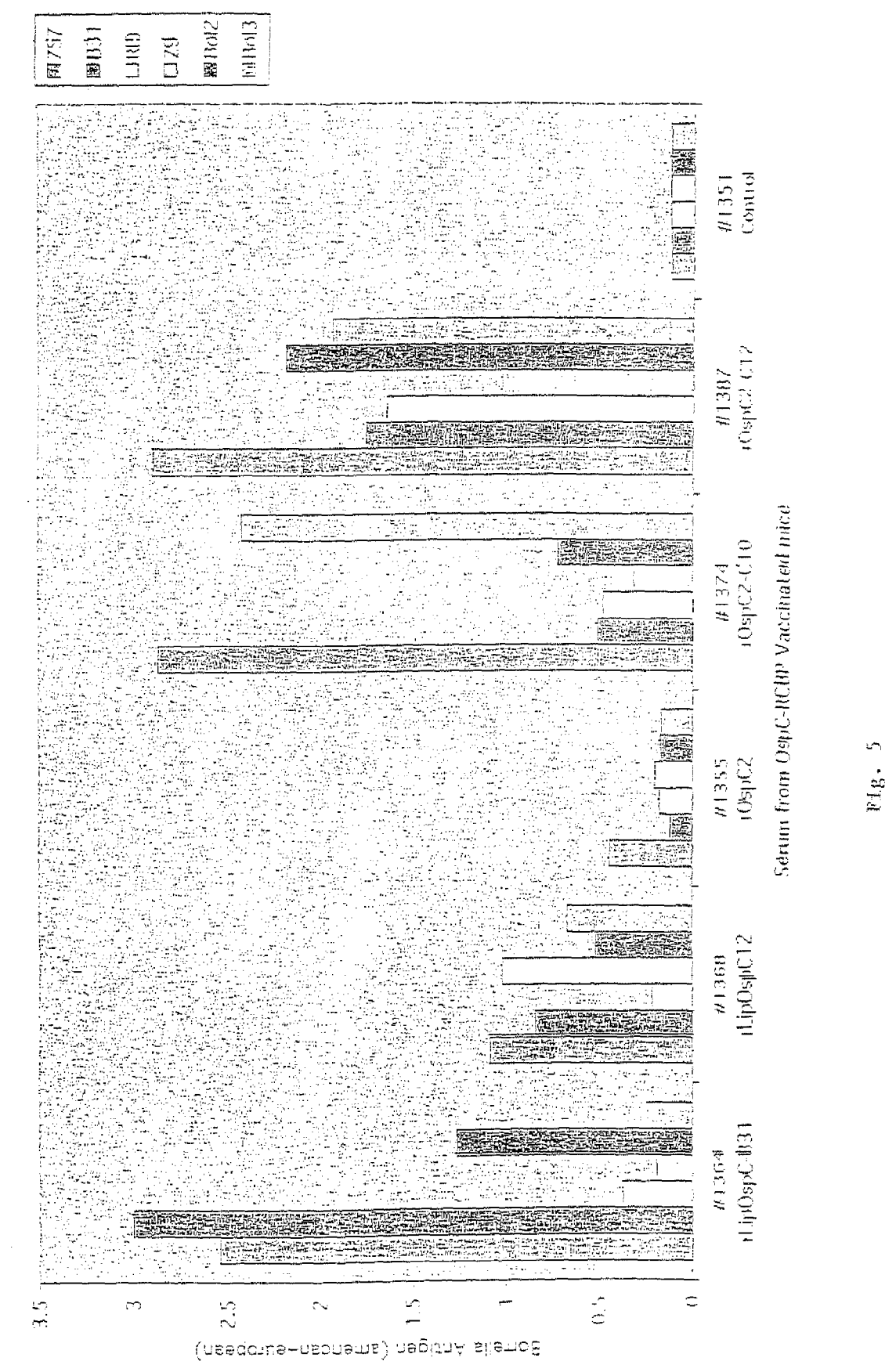

As shown in FIG. 5, chimeric proteins unlipC2C10 and unlipC2C12 of the present invention elicited an immune response that detected 5/6,and 6/6 of the strains tested, as compared to the gold standard lipidated proteins LipC12 and LipCB31, which detected 5/6 and 3/6 of the strains, respectively. When compared to the parental unlipidated OspC2 (rOspC2), the chimeric proteins unlipC2C10 and unlipC2C12 elicited an immune response and detected more strains than the gold standard ((0/6) versus (5/6) and (6/6) respectively). This result was unforeseen and unexpected.

Figure 6:
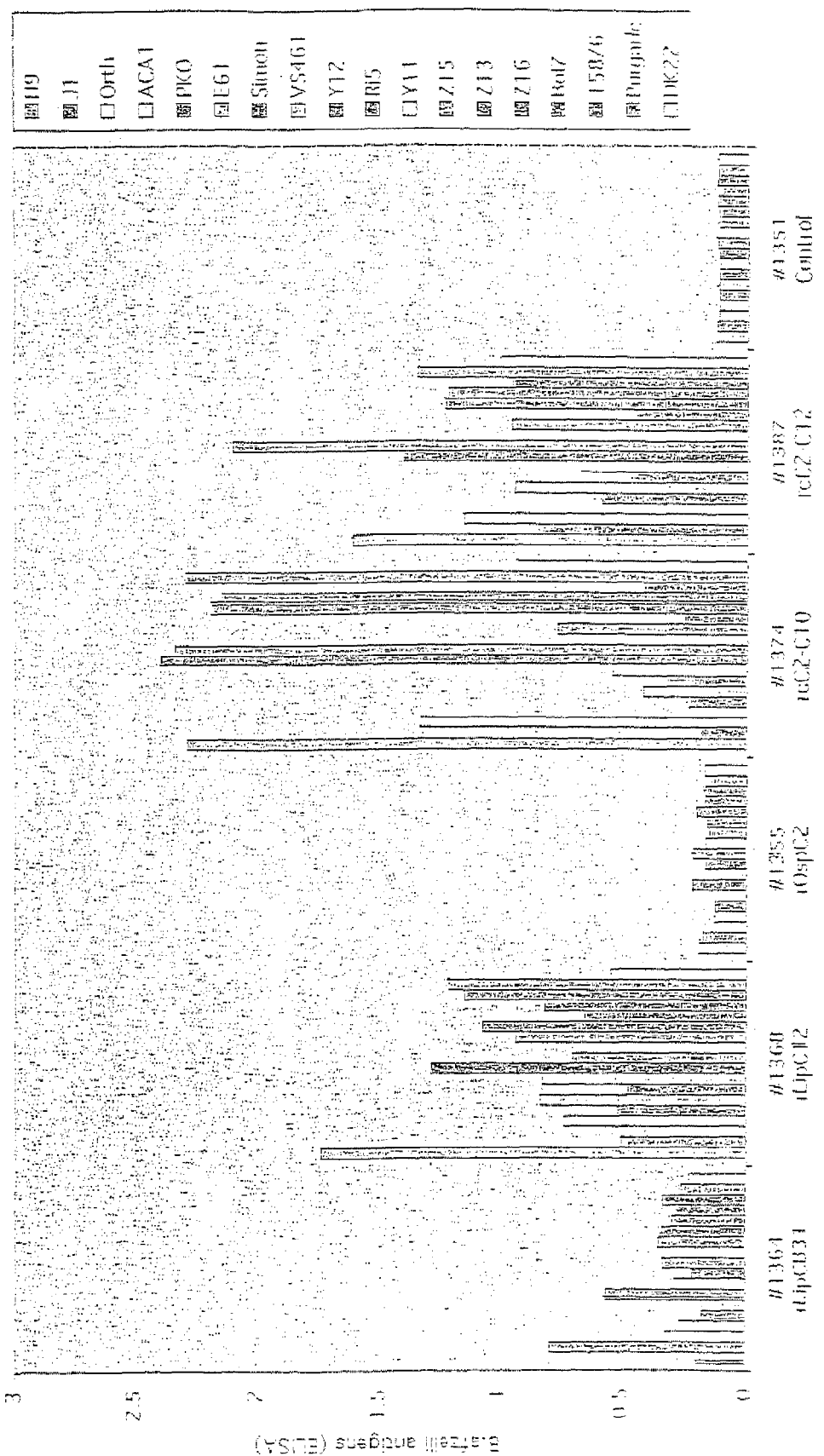
Figure 7:
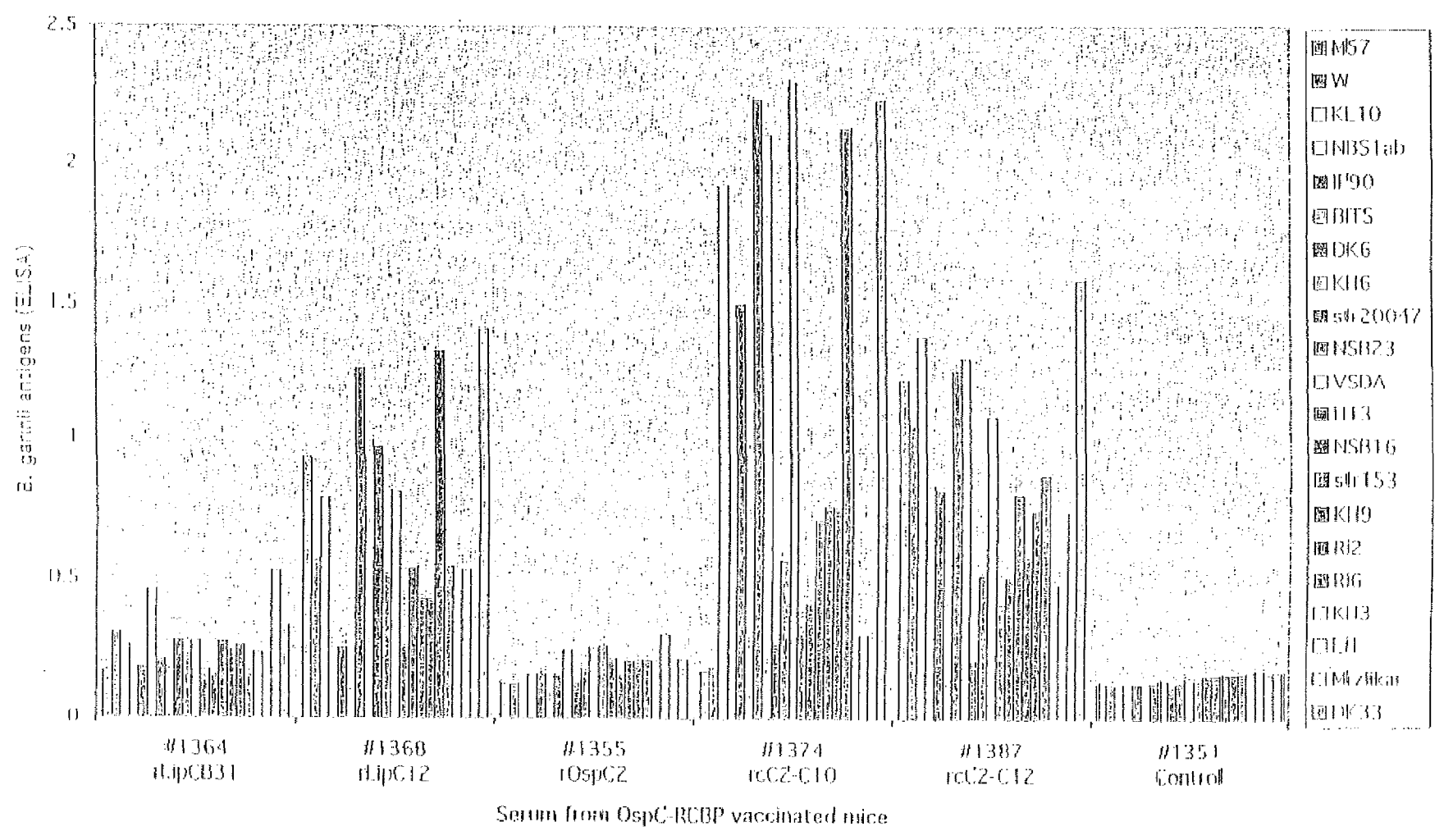

In another experiment, as shown in FIGS. 6 and 7, chimeric proteins of the present invention elicited a significant immune response across all the 18 different strains of B. afzelii (FIG. 6) and all the 21 different strains of B. garinii (FIG. 7). For example, the chimeras unlipC2C10 and unlipC2C12 detected 12 and 18 of the 18 strains of B. afzelii, respectively, as compared to 0/18 detected by the parental unlipidated C2. The same chimeras detected 14 and 20 of the 21 strains of B. garinii, respectively, as compared to 0/21 detected by the parental unlipidated C2. Furthermore, the gold standards LipCB31 and LipC12 detected 2 and 17 of the 18 strains of B. afzelii, respectively, and 2 and 15 of the 21 strains of B. garinii. These results indicate that, unlike the LipOspCB31, LipOspC12 and unlipOspC2, the unlipidated C2C10 and unlipidated C2C12 used as immunogens elicited a significant immune response across all the different strains of B. burgdorferi, B. afzelii and B. garinii tested.

Additional chimeras were constructed and are listed in Table VII.

TABLE VII

OspC Polypeptides and Chimeric Polypeptides of the Present Invention

| POLYPEPTIDE | SEQ ID NO.: (DNA) | (POLYPEPTIDES) |
|---|---|---|
| [1]unlip OspC kkp(55-621*) | 45 | 46 |
| unlip OspC PKO | 47 | 48 |
| unlip OspC TRO | 49 | 50 |
| [2]unlip OspC-55B31/58PKO/56TRO | 51 | 52 |
| unlip OspC2-TRO | 53 | 54 |
| unlip OspCB31-TRO | 55 | 56 |
| unlip OspCPkoCTro | 57 | 58 |
| [3]BlipOspC1C10 | 59 | 60 |
| Blip OspC5C7 | 75 | 76 |
| Blip OspC2C12 | 65 | 76 |
| Blip OspC1C12 | 61 | 62 |
| Blip OspC2C10 | 63 | 64 |
| Blip OspC2C7 | 67 | 69 |
| Blip OspC5C12 | 73 | 74 |
| Blip OspC2TRO | 69 | 70 |
| Blip OspC5C10 | 71 | 72 |
| Blip OspCB31TRO | 77 | 78 |
| Blip OspCB31C10 | 79 | 80 |
| Blip OspCB31C12 | 81 | 82 |
| Blip OspCPkoTro | 83 | 84 |

[1]Ulip means the polypeptide is unlipidated.
[2]An OspC chimera comprised of 3 OspC polypeptides.
[3]Blip means the polypeptide is lipidated due to the gene having the OspB lipidation signal on the 5' terminus.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of immunizing an animal against Lyme disease, comprising administering a composition comprising at least two OspC polypeptides from Lyme Disease causing *Borrelia* wherein said composition comprises one or more OspC polypeptides from at least two *Borrelia burgdorferi sensu stricto* OspC families selected from the group consisting of: A, B, I and K, excepting the combination consisting of two OspC proteins wherein one OspC protein is from OspC family A and the second OspC protein is from OspC family I.

2. The method of claim 1, wherein the composition comprises one or more OspC polypeptides from each *Borrelia burgdorferi sensu stricto* family.

3. The method of claim 1, wherein said OspC polypeptide comprises the OspC protein variable region.

4. The method of claim 1, wherein one of the OspC polypeptide is encoded by a nucleic acid comprising nucleotide 26 to about nucleotide 621 of an ospC gene from a *Borrelia burgdorferi sensu stricto* family selected from the group consisting of: A, B, I and K.

5. The method of claim 1, wherein one of the OspC polypeptides is encoded by a nucleic acid comprising nucleotide 53 to about nucleotide 570 of an ospC gene from a *Borrelia burgdorferi sensu stricto* family selected from the group consisting of: A, B, I and K.

6. The method of claim 1, wherein at least two of said OspC polypeptides are fused together in a single protein, encoded by a single nucleic acid, wherein polypeptides in said fusion protein are not found in the same configuration in a naturally occurring OspC protein.

7. The method of claim 1, wherein the ospC gene encoded the OspC polypeptides within a given OspC family are at least 98% identical at the nucleic acid level.

8. The method of claim 1, wherein *Borrelia burgdorferi sensu stricto* OspC family A comprises strains B31, CA4, HII, IPI, IP2, IP3, L5, PIF, Pka, Txgw and strains containing ospC allele OC1.

9. The method of claim 1, wherein *Borrelia burgdorferi sensu stricto* OspC family B comprises strains 35B808, 61 BV3, BUR, DK7, PB3, Z57 and strains containing ospC genes OC2 and OC3.

10. The method of claim 1, wherein *Borrelia burgdorferi sensu stricto* OspC family I comprises strains 297, HB19 and strains containing ospC gene OC10, wherein strain 297 is characterized by ospC of GenBank accession number L42893 (SEQ ID NO:85).

11. The method of claim 1, wherein *Borrelia burgdorferi sensu stricto* OspC family K comprises strains 272, 297, 28354, KIPP, MUL and strains containing ospC gene OC12 and OC13, wherein strain 297 is characterized by ospC of GenBank accession number U08284 (SEQ ID NO:86).

12. A method of detecting an immune response to Lyme Disease causing *Borrelia* in a host sample, comprising;

a) contacting the host sample with a composition comprising OspC polypeptides from Lyme disease causing strains of *Borrelia*, such that anti-OspC antibodies, if present in said sample bind to said OspC polypeptides; wherein said composition comprises one or more OspC polypeptides from at least two *Borrelia burgdorferi sensu stricto* OspC families selected from the group consisting of: A, B, I and K, excepting the combination consisting of two OspC proteins wherein one OspC proteins is from family A and the second OspC protein is from family I, and b) detecting antibodies that have bound said OspC peptides; thereby detecting an immune response to Lyme disease causing *Borrelia*.

13. The method of claim 12, wherein said OspC polypeptide comprises the OspC protein variable region.

14. The method of claim 12, wherein one of the OspC polypeptide is encoded by a nucleic acid comprising nucleotide 26 to about nucleotide 621 of an ospC gene from a *Borrelia burgdorferi sensu stricto* family selected from the group consisting of: A, B, I and K.

15. The method of claim 12, wherein one of the OspC polypeptides is encoded by a nucleic acid comprising nucleotide 53 to about nucleotide 570 of an ospC gene from a *Borrelia burgdorferi sensu stricto* family selected from the group consisting of: A, B, I and K.

16. The method of claim 12, wherein at least two of said OspC polypeptides are fused together in a single protein, encoded by a single nucleic acid, wherein polypeptides in said fusion protein are not found in the same configuration in a naturally occurring OspC protein.

17. The method of claim 12, wherein the ospC genes encoding the OspC polypeptides within a given OspC family are at least 98% identical at the nucleic acid level.

18. The method of claim 17, wherein *Borrelia burgdorferi sensu stricto* OspC family A comprises strains B31, CA4, HII, IPI, IP2, IP3, L5, PIF, Pka, Txgw and strains containing ospC allele OC1.

19. The method of claim 17, wherein *Borrelia burgdorferi sensu stricto* OspC family B comprises strains 35B808, 61 BV3, BUR, DK7, PB3, Z57 and strains containing ospC genes OC2 and OC3.

20. The method of claim 17, wherein *Borrelia burgdorferi sensu stricto* OspC family I comprises strains 297, HB19 and strains containing ospC gene OC10, wherein strain 297 is characterized by ospC of GenBank accession number L42893 (SEQ ID NO:85).

21. The method of claim 17, wherein *Borrelia burgdorferi sensu stricto* OspC family K comprises strains 272, 297, 28354, KIPP, MUL and strains containing ospC gene OC12 and OC13, wherein strain 297 is characterized by ospC of GenBank accession number U08284 (SEQ ID NO:86).

* * * * *

UNITED STATES PATENT AND TRADEMARK OFFICE
CERTIFICATE OF CORRECTION

PATENT NO.        : 7,582,304 B2
APPLICATION NO. : 11/371564
DATED              : September 1, 2009
INVENTOR(S)      : Dattwyler et al.

It is certified that error appears in the above-identified patent and that said Letters Patent is hereby corrected as shown below:

Column 197, line 26, delete "polypeptide" and insert -- polypetides --

Column 197, line 40, delete "gene encoded" and insert -- genes encoding --

Column 198, lines 18-19, delete "proteins" and insert -- protein --

Signed and Sealed this

Third Day of November, 2009

David J. Kappos
*Director of the United States Patent and Trademark Office*